US008932606B2

(12) United States Patent
Schoenbrunner et al.

(10) Patent No.: US 8,932,606 B2
(45) Date of Patent: Jan. 13, 2015

(54) CHIMERIC PESTIVIRUS WITH INSERTION IN 3' NONTRANSLATED REGION (3'NTR) WITH STABLE REPLICATION AND RNASE RESISTANCE

(75) Inventors: Erhard Schoenbrunner, Moraga, CA (US); Sven-Erik Behrens, Halle (DE)

(73) Assignee: Life Technologies Corporation, Carlsbad, CA (US)

( * ) Notice: Subject to any disclaimer, the term of this patent is extended or adjusted under 35 U.S.C. 154(b) by 382 days.

(21) Appl. No.: 13/131,027

(22) PCT Filed: Nov. 24, 2009

(86) PCT No.: PCT/US2009/065826

§ 371 (c)(1), (2), (4) Date: Sep. 8, 2011

(87) PCT Pub. No.: WO2010/060114

PCT Pub. Date: May 27, 2010

(65) Prior Publication Data

US 2011/0318813 A1 Dec. 29, 2011

Related U.S. Application Data

(63) Continuation of application No. 12/277,282, filed on Nov. 24, 2008, now abandoned.

(51) Int. Cl.

| | |
|---|---|
| ***A61K 39/12*** | (2006.01) |
| ***A61K 39/15*** | (2006.01) |
| ***A61K 39/193*** | (2006.01) |
| ***A61K 39/29*** | (2006.01) |
| ***C12N 7/00*** | (2006.01) |

(52) U.S. Cl.

CPC ........ *C12N 7/00* (2013.01); *C12N 2770/24211* (2013.01); *C12N 2770/24222* (2013.01); *C12N 2770/24311* (2013.01); *C12N 2770/24322* (2013.01)

USPC .................. 424/218.1; 424/225.1; 424/228.1

(58) Field of Classification Search

CPC ........... C12N 7/00; C12N 2770/24211; C12N 2770/24222; C12N 2770/24311; C12N 2770/24322

USPC ................................ 424/218.1, 225.1, 228.1

See application file for complete search history.

(56) References Cited

U.S. PATENT DOCUMENTS

| | | | |
|---|---|---|---|
| 5,677,124 | A | 10/1997 | DuBois et al. |
| 5,912,145 | A | 6/1999 | Stanley et al. |
| 5,919,625 | A | 7/1999 | DuBois et al. |
| 5,939,262 | A | 8/1999 | Pasloske et al. |
| 6,001,613 | A | 12/1999 | Donis et al. |
| 6,127,116 | A | 10/2000 | Rice et al. |
| 6,214,982 | B1 | 4/2001 | Pasloske et al. |
| 6,326,137 | B1 | 12/2001 | Hong et al. |
| 6,399,307 | B1 | 6/2002 | Pasloske et al. |
| 7,009,044 | B1 | 3/2006 | Nam et al. |
| 7,033,749 | B2 | 4/2006 | Pasloske et al. |
| 7,141,405 | B2 | 11/2006 | Martin et al. |
| 7,183,084 | B2 | 2/2007 | Jaeger |
| 7,192,745 | B2 | 3/2007 | Jaeger |
| 7,473,772 | B2 | 1/2009 | Martin et al. |
| 2006/0105365 | A1 | 5/2006 | Martin et al. |
| 2006/0257889 | A1 | 11/2006 | Pasloske et al. |
| 2010/0129902 | A1 | 5/2010 | Schoenbrunner et al. |

FOREIGN PATENT DOCUMENTS

| | | |
|---|---|---|
| EP | 0701627 | 1/1997 |
| EP | 0910643 | 8/2006 |
| WO | WO-94/28171 | 12/1994 |
| WO | WO-95/15974 | 6/1995 |
| WO | WO-98/00547 | 1/1998 |
| WO | WO-99/55366 | 11/1999 |
| WO | WO-00/75352 | 12/2000 |
| WO | WO-2007/002793 | 1/2007 |
| WO | WO-2010/060114 | 5/2010 |

OTHER PUBLICATIONS

Gorecki, D., 2001, Expert Opin. Emerging Drugs, 6(2): 187-198.*
Thomas et al., 2003, Nature Reviews/ Genetics, vol. 4, p. 346-358.*
Lebedeva et al., 2003, Seminars in Cancer Biology, vol. 12, p. 169-178.*
Kodama et al., 2006, Current Medicinal Chemistry, vol. 13, p. 2155-2161.*
"ISO Standard 17511", 2003.
"Molecular Diagnostic Methods for Infectious Disease, Approved Guideline", *2nd ed., Clinical and Laboratory Standards Institute*, vol. 26(8), 2006.
U.S. Appl. No. 12/277,282, "Office Action Mailed Apr. 5, 2010".
U.S. Appl. No. 12/277,282, "Office Action Mailed Jul. 30, 2010".
U.S. Appl. No. 12/277,282, "Office action mailed on Mar. 23, 2011".
U.S. Appl. No. 12/277,282, "Office Action Mailed on Jul. 20, 2011".
U.S. Appl. No. 12/277,282, "Response to Mar. 23, 2011 Final Office Action Filed May 9, 2011".
U.S. Appl. No. 12/277,282, "Response to Apr. 5, 2010 Office Action (Restriction Requirement) Filed Jun. 1, 2010".
U.S. Appl. No. 12/277,282, "Response to Jul. 20, 2011 Office Action Filed Nov. 14, 2011".
U.S. Appl. No. 12/277,282, "Response to Jul. 30, 2010 Non-final Office Action Filed Jan. 31, 2011".
Altmeyer, R., et al., "Attenuated Mengo virus as a vector for immunogenic human immunodeficiency virus type 1 glycoprotein 120", *PNAS*, vol. 91(21), 1994, 9775-9779.

(Continued)

*Primary Examiner* — Shin Lin Chen

(57) ABSTRACT

The construction of a chimeric Pestivirus by the identification of selected regions in the 3'NTR of the viral RNA genome is described where additional RNA sequences can be stably inserted. These sequence insertions in the viral RNA genome were stable in replication and capable of forming infectious, RNase resistant virus particles. This chimeric Pestivirus with a 3'NTR insertion can be utilized as a quality control material in analytical assays for RNA targets, including external, internal controls, quantitative standards in PCR and NAT nucleic acid assays.

8 Claims, 37 Drawing Sheets

(56) References Cited

OTHER PUBLICATIONS

Ansardi, D. C., et al., "Encapsidation and serial passage of a poliovirus replicon which expresses an inactive 2A proteinase", *J. Virol.*, vol. 69(2), 1995, 1359-1366.
Azrolan, N., et al., "A Solution Hybridization / RNase Protection Assay with Riboprobes to Determine Absolute Levels of apoB, A-I and E mRNA in Human Hepatoma Cell Lines", *J. Lipid. Res.*, vol. 31, 1990, 1141-1146.
Baroth, M., et al., "Stable recombinants of bovine viral diarrhea virus containing a hepatitis C virus insert", *J. Gen. Virol*, vol. advance e-pub,, 1/62010.
Becher, P., et al., "Complete Genomic Sequence of Border Disease Virus, a Pestivirus from Sheep", *J. Virol.*, vol. 72(6), 1998, 5165-5173.
Becher, P., et al., "Mutations in the 5' Nontranslated Region of Bovine Viral Diarrhea Virus Result in Altered Growth Characteristics", *J. Virol.*, vol. 74(17), 2000, 7884-7894.
Behrens, et al., "Cis- and Trans-acting Determinants of Flaviviridae Replication", *Molecular Biology of the Flavivirus: Horizon Bioscience*, 2006, 101-134.
Behrens, S. E., et al., "Characterization of an Autonomous Subgenomic Pestivirus RNA Replicon", *J. Virol.*, vol. 72(3), 1998, 2364-2372.
Choi, W. S., et al., "Expression of Human Immunodeficiency Virus Type 1 (HIV-1) gag, pol, and env Proteins from Chimeric HIV-1 Poliovirus Minireplicons", *J. Virology*, vol. 65(6), 1991, 2875-2883.
Deng, R., et al., "5' and 3; Untranslated Regions of Pestivirus Genome: Primary and Secondary Structure Analyses", *Nucleic Acids Research*, vol. 21(8), 1993, 1949-1957.
Derse, D., et al., "Construction of a recombinant bovine leukemia virus vector for analysis of virus infectivity", *J. Virol.*, vol. 64(1), 1990, 401-405.
Dichek, D., A. et al., "Characterization of Recombinant Plasminogen Activator Production by Primate Endothelial Cells Transduced with Retroviral Vectors", *Blood*, vol. 84, 1994, 504-516.
Donson, J., et al., "Systemic expression of a bacterial gene by a tobacco mosaic virus-based vector", *PNAS*, vol. 88(16), 1991, 7204-7208.
FDA, "Guidance for Industry in the Manufacture and Clinical Evaluation of In Vitro Tests to Detect Nucleic Acid Sequences of Human Immunodeficiency Viruses Types 1 and 2", *Section III G.*
Filocamo, G., et al., "Chimeric Sindbis viruses dependent on the NS3 protease of hepatitis C virus", *J. Virol.*, vol. 71(2), 1997, 1417-1427.
Frolov, et al., "cis-acting RNA elements required for replication of bovine viral diarrhea virus-hepatitis C virus 5' nontranslated region chimeras", *RNA*, 4, 1998, 1418-1435.
Frolov, Ilya, et al., "Alphavirus-based expression vectors: strategies and applications", *PNAS*, vol. 93(21), 1996, 11371-11377.
Gallie, D. R., et al., "In Vivo Uncoating and Efficient Expression of Foreign mRNAs Packaged in TMV-Like Particles", *Science*, vol. 236, May 1987, 1122-1124.
Giavedoni, L. D., et al., "Vaccinia virus recombinants expressing chimeric proteins of human immunodeficiency virus and gamma interferon are attenuated for nude mice", *PNAS*, vol. 89(8), 1992, 3409-3413.
Grassman, C., et al., "Hepatitis C Virus and the Related Bovine Viral Diarrhea Virus Considerably Differ in the Functional Organization of the 5' Non-translated Region: Implications for the Viral Life Cycle", *Virology*, vol. 15:333(2), 2005, 349-366.
Gritz, L., et al., "Generation of Hybrid Genes and Proteins by Vaccinia Virus-Mediated Recombination: Application to Human Immunodeficiency Virus Type 1 env", *J. Virology*, vol. 64(12), Dec. 1990, 5948-5957.
Hanecak, R., et al., "Antisense Oligonucleotide Inhibition of Hepatitis C Virus Gene Expression in Transformed Hepatocytes", *J. Virology*, vol. 70(8), Aug. 1996, 5203-5212.
Harrison, B. D., et al., "Milestones in the Research on Tobacco Mosaic Virus" *Phil. Trans. R. Soc.* London, B 354, 1999, 521-529.
Heidenreich, O, et al., "Chemically Modified RNA: Approaches and Applications" *FASEB J.*, vol. 7(1), Jan. 1993, 90-96.
Hwang, D-J, et al., "Expression of tobacco mosaic virus coat protein and assembly of pseudovirus particles in *Escherichia coli", PNAS*, vol. 91(19), 1994, 9067-9071.
Isken, O., et al., "Complex signals in the genomic 3' non-translated region of bovine viral diarrhea virus coordinate translation and replication of the viral RNA", *RNA*, vol. 10, 2004, 1637-1652.
Isken, O., et al., "Members of the NF90/NFAR Protein Group are Involved in the Life Cycle of a Positive-Strand RNA Virus", *EMBO J.*, vol. 22, 2003, 5655-5665.
Isken, O., et al., "Nuclear Factors are Involved in Hepatitis C Virus RNA Replication", *RNA*, vol. 13, 2007, 1675-1692.
Jupin, I., et al., "Direct recovery of in vitro transcripts in a protected form suitable for prolonged storage and shipment at ambient temperatures", *Nucl. Acids Res.*, vol. 17(2), 1989, 815.
Khromykh, Alexander A., et al., "Encapsidation of the Flavivirus Kunjin Replicon RNA by Using a Complementation System Providing Kunjin Virus Structural Proteins in trans", *J. Virol.*, vol. 72, Jul. 1998, 5967-5977.
Khromykh, Alexander A., et al., "trans-Complementation of Flavivirus RNA Polymerase Gene NS5 by Using Kunjin Virus Replicon-Expressing BHK Cells", *J. Virol.*, vol. 72, Sep. 1998, 7270-7279.
Kohara, Michinori, et al., "Expression and characterization of glycoprotein gp35 of hepatitis C virus using recombinant vaccinia virus", *J. Gen. Virol.*, vol. 73, Sep. 1992, 2313-2318.
Kumagai M., et al., "Rapid, high-level expression of biologically active alpha-trichosanthin in transfected plants by an RNA viral vector", *PNAS*, vol. 90(2), 1993, 427-430.
Lee, Haekyung, et al., "The C-Terminal Hydrophobic Domain of Hepatitis C Virus RNA Polymerase NS5B can be Replaced with a Heterologous Domain of Poliovirus Protein 3A", *J. Virol.*, vol. 80, Nov. 1, 2006, 11343-11354.
Lim, Francis, et al., "tations that increase the affinity of a translational repressor for RNA", *Nucl. Acids Res.*, vol. 22(18), 1994, 3748-3752.
Lindenbach, et al., "Flavivirdae: The Viruses and their Replication", *Fields Virology*, 5th ed., Knipe, et al., Lippincott, 2007, 1101-1152.
Lohmann, V., et al., "Replication of Subgenomic Hepatitis C Virus RNAs in Hepatoma Cell Line", *Science*, vol. 285(5424), 1999, 110-113.
Lu, H. H., et al., "Poliovirus chimeras replicating under the translational control of genetic elements of hepatitis C virus reveal unusual properties of the internal ribosomal entry site of hepatitis C virus", *PNAS*, vol. 93(4), 1996, 1412-1417.
Makoschey, et al., "Bovine Viral Diarrhea Virus with Deletions in the 5'-Nontranlated Region: Reduction of Replication in Calves and Induction of Protective Immunity", vol. 22, 2004, 3285-3294.
Mamounas, M., et al., "An infectious chimeric human immunodeficiency virus type 2 (HIV-2) expressing the HIV-1 principal neutralizing determinant", *J. Virol.* vol. 69(10), Oct. 1995, 6424-6429.
Meyers, G., et al., "Recovery of Cytopathogenic and Noncytopathogenic Bovine Viral Diarrhea Viruses from cDNA Contructs", *J. Virology*, vol. 70, 1996, 9603-9613.
Mivechi, Nahid F., et al., "Use of Polymerase Chain Reaction to Detect the Expression of the Mr 70,000 Heat Shock Genes in Control or Heat Shock Leukemic Cells as Correlated to Their Heat Response", *Cancer Res.*, vol. 50, May 15, 1990, 2877-2884.
Monroe, S. S., et al., "Sequence analysis of cDNA's derived from the RNA of Sindbis virions and of defective interfering particles", *J. Virol.*, vol. 41, Jan. 1982, 153-162.
Nolte, F. S., et al., "Clinical evaluation of two methods for genotyping Hepatitis C virus based on analysis of the 5' noncoding region", J. Clin. Microbiol., vol. 41, No. 4, Apr. 2003, 1558-1564.
Olkkonen, V. M., et al., "In vitro assembly of infectious nucleocapsids of bacteriophage phi 6: formation of a recombinant double-stranded RNA virus", *PNAS*, vol. 87(23), 1990, 9173-9177.
Onodera, S., et al., "Construction of a transducing virus from double-stranded RNA bacteriophage phi6: establishment of carrier states in host cells", *J. Virol.*, vol. 66, Jan. 1992, 190-196.
Page, K. A., et al., "Construction and use of a human immunodeficiency virus vector for analysis of virus infectivity", *J. Virol.*, vol. 64(11), Nov. 1990, 5270-5276.

(56) References Cited

OTHER PUBLICATIONS

Pal-Ghosh, R., et al., "A poliovirus minireplicon containing an inactive 2A proteinase is expressed in vaccinia virus-infected cells", *J. Virol.*, vol. 67(8), Aug. 1993, 4621-4629.
Pankraz, A., et al., "Essential and nonessential elements in the 3' nontranslated region of bovine viral diarrhea virus", *J. Virol*, vol. 79, No. 14, Jul. 2005, 9119-9127.
Pape, M. E., et al., "Molecular cloning, sequence, and expression of cynomolgus monkey cholesteryl ester transfer protein. Inverse correlation between hepatic cholesteryl ester transfer protein mRNA levels and plasma high density lipoprotein levels", *Arterioscler Thromb Vasc. Biol.*, vol. 11, 1991, 1759-1771.
Pape, M. E., et al., "mRNA Quantitation by a Simple and Sensitive RNAse Protection Assay", *GATA*, vol. 8(7), 1991, 206-213.
Pape, M. E., et al., "Select this articleAn improved method for precise quantitation of cellular and tissue apolipoprotein A-I mRNA levels by use of an internal standard", *J. Lipid Res.*, vol. 31(4), 1990, 727-733.
Pasloske, Britton L., et al., "Armored RNA Technology for Production of Ribonuclease-Resistant Viral RNA Controls and Standards", *J. Clin. Microbiol.*, vol. 36(12), Dec. 1998, 3590-3594.
PCT/US09/65826, "International Search Report Mailed on Oct. 3, 2010".
Perrault, J., et al., "Internal genome deletions in two distinct classes of defective interfering particles of vesicular stomatitis virus", *PNAS*, Vo. 76(12), 1979, 6191-6195.
Pickett, Gavin G., et al., "Encapsidation of heterologous RNAs by bacteriophage MS2 coat protein", *Nucl. Acids Res.*, vol. 21(19), 1993, 4621-4626.
Porter, D. C., et al., "Encapsidation of genetically engineered poliovirus minireplicons which express human immunodeficiency virus type 1 Gag an Pol proteins upon infection", *J. Virol.*, vol. 67, Jul. 1993, 3712-3719.
Puig, M., et al., "Detection of adenoviruses and enteroviruses in polluted waters by nested PCR amplification", *Appl. Environ. Microbiol.*, vol. 60, Aug. 1994, 2963-2970.
Qiao, X., et al., "Interference with bacteriophage phi 6 genomic RNA packaging by hairpin structures", *J. Virol.*, vol. 69, Sep. 1995, 5502-5505.
Qu, Lin, et al., "Isolation and Characterization of Noncytopathic Pestivirus Mutants Reveals a Role for Nonstructural Protein NS4B in Viral Cytopathogenicity", *J. Virol.*, vol. 75, Nov. 2001, 10651-10662.
Roth, W. K., et al., "Comparison of two quantitative hepatitis C virus reverse transcriptase PCR assays", *J. Clin. Microbiol.*, vol. 34(2), Feb. 1996, 261-264.
Ruster, B., et al., "Quantification of Hepatitis C Virus RNA by Competitive Reverse Transcription and Polymerase Chain Reaction Using a Modified Hepatitis C Virus RNA Transcript", Analytical Biochemistry, vol. 224(2), Jan. 1995, 597-600.
Seeger, et al., "Expression of infectious woodchuck hepatitis virus in murine and avian fibroblasts",*J. Virol.*, vol. 63, Nov. 1989, 4665-4669.
Shafer, G. E., et al., "Expression of a swine class II gene in murine bone marrow hematopoietic cells by retroviral-mediated gene transfer", *PNAS*, vol. 88(21), 1991, 9760-9764.
Shyamala, V., et al., "Detection, Validation and Quantification of West Nile Virus RNA by the Alternate NAT WNV Assay", *AABB Poster*, 2003.
Sleat, D. E., et al., "Packaging of Recombinant RNA Molecules into Pseudovirus Particles Directed by the Origin-of-Assembly Sequence from Tobacco Mosaic Virus RNA", *Virology*, vol. 155, 1986, 299-308.
Smith, A. D., et al., "Use of random systematic mutagenesis to generate viable human rhinovirus 14 chimeras displaying human immunodeficiency virus type 1 V3 loop sequences", *J. Virol.*, vol. 68, Jan. 1994, 575-579.
Stettler, P., et al., "Establishment and Application of Bicistronic Classical Swine Fever Virus Genomes for Foreign Gene Expression and Complementation of E2 Deletion Mutants" *Virus Research*, vol. 85, Feb. 2002, 173-185.
Tautz, N., et al., "Cytopathogenicity of a Pestivirus Correlates with a 27-Nucleotide Insertion", *J. Virology*, vol. 70(11), 1996, 7851-7858.
Tautz, N., et al., "Establishment and Characterization of Cytopathogenic and Noncytopathogenic Pestivirus Replicons", *J. Virol.*, vol. 73, Nov. 1999, 9422-9432.
Turner, D. R., et al., "Assembly of hybrid RNAs with tobacco mosaic virus coat protein: Evidence for incorporation of disks in 5'-elongation along the major RNA tail", *J. Mol. Biol.*, vol. 209(3), Oct. 5, 1989, 407-422.
Vassilev, V. B., et al., "Authentic and Chimeric Full-Length Genomic cDNA Clones of Bovine Viral Diarrhea Virus That Yield Infectious Transcripts", *J. Virology*, vol. 71, 1997, 471-478.
Vella, Cherelyn, et al., "Characterization and primary structure of a human immunodeficiency virus type 1 (HIV-1) neutralization domain as presented by a poliovirus type 1/HIV-1 chimera", *J. Gen. Virol.*, vol. 74, Dec. 1993, 2603-2607.
Vilcek, S., "Genetic variability of bovine viral diarrhoea virus sUbtypes at 3'-nontranslated region", *Virus Genes, Kluwer Academic Publishers*, vol. 34, No. 1, Aug. 18, 2006, 31-35.
Walkerpeach, Cindy R., et al., "Ribonuclease-resistant RNA Controls (Armored RNA) for Reverse Transcription-PCR, Branched DNA, and Genotyping Assays for Hepatitis C Virus", *Clinical Chemistry*, vol. 45, 1999, 2079-2085.
Wang, A. J. et al., "Quantitation of mRNA by the polymerase chain reaction", *PNAS*, vol. 86(24), 1989, 9717-9721.
Widjojoatmodjo, M., et al., "Classical Swine Fever Virus ErnsDeletion Mutants: trans-Complementation and Potential Use as Nontransmissible, Modified, Live-Attenuated Marker Vaccines", *J. Virol.*, vol. 74, Apr. 2000, 2973-2980.
Wilson, T. M., et al., "Strategies to protect crop plants against viruses: pathogen-derived resistance blossoms", *PNAS*, vol. 90(8), 1993, 3134-3141.
Yu, H., et al., "Sequence and Structural Elements at the 3' Terminus of Bovine Viral Diarrhea Virus Genomica RNA: Functional Role during RNA Replication", *J. Virology*, vol. 73(5), 1999, 3638-3648.
Zhang, Hong, et al., "Antisense Oligonucleotide Inhibition of Hepatitis C Virus (HCV) Gene Expression in Livers of Mice Infected with an HCV-Vaccinia Virus Recombinant", *Antimicrob. Agents Chemother.*, vol. 43, Feb. 1999, 347-353.
U.S. Appl. No. 12/277,282, "Final Office Action mailed Jan. 11, 2012."
Pankraz, A. et al., "A Single Point Mutation in Nonstructural Protein NS2 Of Bovine Viral Diarrhea Virus Results in Temperature-Sensitive Attenuation of Viral Cytopathogenicity", *Journal of Virology*, vol. 83 (23), Sep. 15, 2009, 1418-1435.
Sarnow, P. et al., "A poliovirus temperature-sensitive RNA synthesis mutant located in a noncoding region of the genome", *Proceedings of the National Academy of Sciences*, vol. 83, Feb. 1986, 571-575.

* cited by examiner

HCV GENOME

BVDV GENOME

*PESTIVIRUS*
RNA CHIMERA

3'NTR OF BVDV

SL<sub>stop</sub> — UGA pos.cons. BOX — PROPOSED INSERTION SITE — SLII →

```
BDV X818        TGAACCATAG  CTGAGCATTT  CATGACAACA  CGCCAAGGGC  CACTAAATTG  TATATATAAC  TGTGTAAATA   70
CSFV C-strain   TGAGC.GCGG  GTAACC.CGG  GATCTGAACC  CGCCAGTAGG  .ACCCTATTG  TAGATAAGAC  TAATTTTCTT   67
CSFV Alfort-T   TGAGC.ATGG  TTGGCC.CTT  GATCGGGCCC  TATCAGTAGA  .ACCCTATTG  TAAATAACAT  TAACTTATTA   67
BVDV-1 NADL     TGAGA.CAAA  ATGTATATAT  TGTAAATA.A  ATTAATCCAT  GTACATAGTG  TATATAAATA  TAGTTGGGAC   68
BVDV-1 Osloss   TGAA..ATAA  ATGTATATAT  TGTACATA.A  ATCTGTATAT  GTACATATTA  TATATAAACT  TAGTTGAGAT   67
BVDV-2 890      TGAATCTGCC  CAGAGAGTCG  TGCCCTCACT  CAAGGTGTCA  TTTGTAAATA  TGGTGAATAG  ACAGCTAAGA   70
                ***                                                 * *   *    *

BDV X818        TTTACCTATT  TATTTACTGT  TATTTATTTA  ATAGAGACAG  TGATATTTAT  TTAATAGCTT  ATCTATTTAT  140
CSFV C-strain   ..........  ..........  .TTTTTTCTT  TTTTATTTAT  TTAGATATTA  CTATTTATTT  ATTTATTTAT  116
CSFV Alfort-T   ..........  ..........  ..........  .....ATTAT  TTAGATACTA  TTATTTATTT  ATTTATTTAT  102
BVDV-1 NADL     ..........  ..........  ..........  ..........  CGTCCACCTC  AAGAAGACGA  CACGCCCAAC   98
BVDV-1 Osloss   ..........  ..........  ..........  ..........  ..........  ..........  ..........   67
BVDV-2 890      ..........  ..........  ..........  ..........  ..........  ..........  .TATATATTG   79

BDV X818        TTATTTGATG  GGATGTAGAT  GGCAACTAAC  TACCTCATAG  GACCACACTA  CACTCATTTT  TAAAACTACA  210
CSFV C-strain   TTATTGAATG  AGTAAGAACT  GGTA.TAAAC  TACCTCAAGT  TACCACACTA  CACTCATTTT  TA.....ACA  180
CSFV Alfort-T   TTATTGAATG  AGCAAGTACT  GGTA.CAAAC  TACCTCATGT  TACCACACTA  CACTCATTTT  A......ACA  165
BVDV-1 NADL     ACGCACAGCT  AAACAGTAGT  CAAGATTATC  TACCTCAAGA  TA..ACACTA  CATTTAATGC  AC.....ACA  161
BVDV-1 Osloss   ........TA  GTAGTG.ATA  TATAGTTATC  TAC.TCAAGT  AA..ACACTA  CACTCAATGC  AC.....ACA  120
BVDV-2 890      TAGTTGGATA  GTAATGTAGT  GATAGT.AGA  TACCCCGATT  TA..ACACTA  CCTCCAATGC  AC.....TAA  141
                                                *  *** *     * ******  *   * *          *

BDV X818        GCACTTTAGC  TGGAAGGGAA  AA.GCCTGAA  GTCCAGAGTT  GGATTAAGGA  AAAACCCTAA  CAGCCCC     276
CSFV C-strain   GCACTTTAGC  TGGAAGGAAA  AT.TCCTGAC  GTCCACAGTT  GGACTAAGGT  AATTT.CTAA  CGGCCC      244
CSFV Alfort-T   GCACTTTAGC  TGGAGGGAAA  AC..CCTGAC  GTCCACAGTT  GGACTAAGGT  AATTTCCTAA  CGGCCC      229
BVDV-1 NADL     GCACTTTAGC  TGTATGAGGA  TACGCCCGAC  GTCTATAGTT  GGACTAGGGA  AGACCTCTAA  CAGCCCCC    229
BVDV-1 Osloss   GCACTTTAGC  TGTATGAGGG  AACACCCGAC  GTCCATGGTT  GGACTAGGGA  AGACCCTTAA  CAGCCCCA    188
BVDV-2 890      GCACTTTAGC  TGTGTGAGGT  TA.ACTCGAC  GTCCATGGTT  GGACTAGAGG  ATGGCTCTAA  CGGTCCCCC   209
                **********  **    *        *  **  *** * ***  *** **  *  *       ***  * * ***
```

BORDER BETWEEN 3'V AND 3'C

LEGEND: * = CONSERVED NUCLEOTIDE

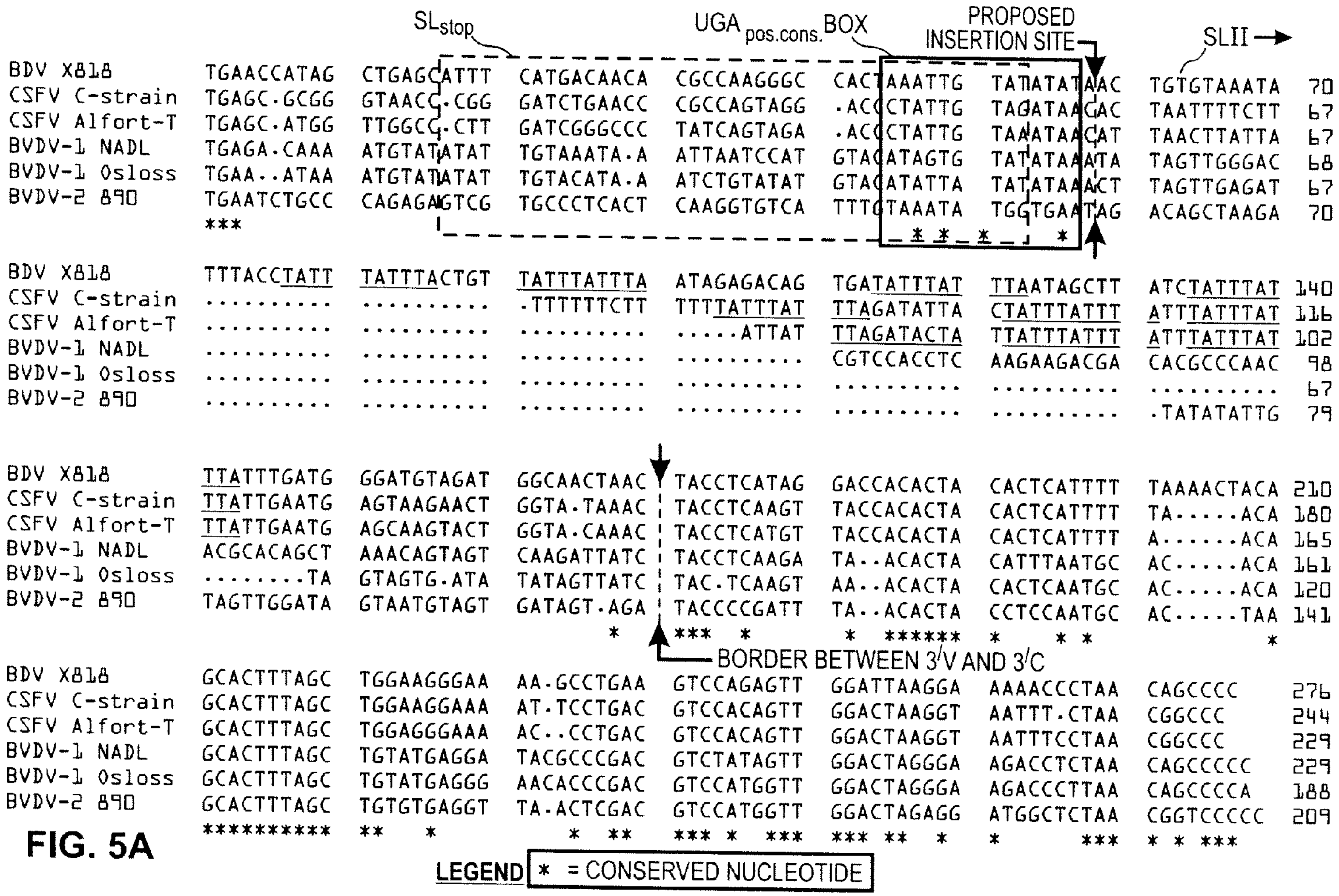

FIG. 5A

| VIRUS STRAIN | "UGA BOX"/POSITION | | | | | |
|---|---|---|---|---|---|---|
| BDV X818 | 46 | AAU | UGU | AUA | UAU | 57 |
| BDV A841/1 | 46 | GAU | UGU | AUA | UAA | 57 |
| CSFV C-strain | 43 | UAU | UGU | AGA | UAA | 54 |
| CSFV Alfort-T | 43 | UAU | UGU | AAA | UAA | 54 |
| BVDV-1 NADL | 44 | UAG | UGU | AUA | UAA | 55 |
| BVDV-1 Osloss | 43 | UAU | UAU | AUA | UAA | 54 |
| | 46 | UAU | UGU | ACA | UAA | 57 |
| BVDV-1 CP7 | 46 | UAU | UAU | GUU | UAA | 57 |
| | 19 | UAU | UGU | ACA | UAA | 30 |
| BVDV-2 890 | 46 | AAA | UAU | GGU | GAA | 57 |
| Singer | 43 | UAU | UGU | AUA | UAA | 54 |
| | 46 | UAU | UGU | AAA | UAA | 57 |

CONSENSUS SEQUENCE

| 1 | 2 | 3 | 4 | 5 | 6 | 7 | 8 | 9 | 10 | 11 | 12 |
|---|---|---|---|---|---|---|---|---|---|---|---|
| U | | U | | A | | A | U | A | U | | U |
| A | <u>A</u> | A | <u>U</u> | | <u>U</u> | | A | | | <u>A</u> | A |
| G | | G | | G | | G | G | U | G | | G |

FIG. 5B gtatacgaggttaggcaagttctcgtatacatattggacactctaaaataattaggcctagggga
caaaaatcctccttagcgaaggccgaaaagaggctaaccatgcccttagtaggactagcaaaataa
ggggggtagcaacagtggcgagttcgttggatggctgaagccctgagtacagggtagtcgtcagtg
gttcgacgctttggaggacaagcctcgagatgccacgtggacgagggcatgcccacagcacatctt
aacctggacaggggtcgttcaggtgaaaacggtttaaccaaccgctacgaatacagtctgatagga
tgctgcagaggcccactgtattgctactgaaaatctctgctgtacatggcacatggagttgatcac
aaatgaactttatacaaaacatacaaacaaaaacccgctggagtggaggaaccagtatacgacca
agctggtaaccctttgtttggagaaagaggagtgattcatccgcagtcaacgctaaaacttccaca
taaaagaggggagcgtgaagtccccaccaatctggcttctttaccaaaaagaggtgactgcaggtc
gggtaacagcaaggggcctgtgagtggaatctacttaaaaccagggccgttattctaccaagatta
taaaggacctgtctatcatagagccccattggagtttttgaggaggcgtctatgtgtgagacaac
taaaagaatagggagagtaactggtagtgacagcagattataccacatttacgtgtgtattgatgg
gtgcataatagtcaagagtgctacaaaagaccgccagaaagtactcaagtgggtccacaacaagct
aaactgccccctatgggtttcaagctgctccgacacaaaagatgaaggggtggtgaggaagaagca
acaaaagccagataggttggaaaaggggagaatgaagataacacctaaggagtcagagaaagacag
taagaccaagccgccagatgctacgatagtggtagatggagtcaagtatcaggtaaagaaaaaagg
aaaagtcaagagcaagaacacccaggacggcttataccacaacaaaaataaacctcaagagtcgcg
caagaaactagagaaagccctattggcctgggcaataatagccctggtttctttcaagtcacaat
gggagagaacataacgcaatggaacttacaagataatggaacggaaggcatacaacgagccatgtt
tcaaagaggagtgaatagaagtttacatgggatctggccagagaaaatctgtacaggtgttccttc
ccacctggccactgacacagaattgaaggcaattcatggtatgatggatgcaagtgagaagacaaa
ttatacgtgctgcagactccaacgccatgaatggaacaaacatggttggtgcaactggtacaacat
tgaaccttggatcctccttatgaataaaactcaggccaaccttactgagggtcagccactaaggga
gtgtgccgtcacatgccggtatgatcgagatagtgacctgaatgtagtaacacaagccagggatag
ccccacaccattaacaggttgcaagaaaggcaaaaactttcctttgcaggcatattggtacaagg
gccttgcaactttgaaatagccgtaagtgatgtgctgttcaaagagcatgattgcactagtgtgat
tcaagacacagctcactacctcgtagacgggatgaccaactccctagagagtgccaggcaagggac
cgcgaaactaacaacttggctgggcaggcagcttgggatactaggaaagaaactggaaaacaagag
taagacatggtttggggcatatgcagcctctccctattgtgaggtagaacggaagcttggttacat
ctggtatacaaagaattgcactccagcctgtttgcctaggaatacaaagatcatcggccccggtag
gtttgacaccaatgccgaggatggtaaaatactgcatgagatggggggtcacttgtcggaggtgct
actactctcagtggtagtgctgtccgatttcgctccagagacagccagtgtgatatacttgattct
tcatttctccatcccacaaggacacactgatatacaagattgtgacaaaaaccaactaaacctcac
cgtagaactcacaacagcagaagtaataccaggctcagtttggaacttgggtaaatatgtttgtgt
aagaccagattggtggccttatgagacagccacagtcctggtgattgaagaggtgggtcaagtaat
taaggttgtcttaagggcgttaaaagatctgacgcgcatttggaccgctgctacaaccactgcatt
cttggtttgtctggtgaaggtagtgagaggccaagtgttacaaggtatactgtggctgatgctcat
aacaggggcgcaagggtacccagactgcaaacccggcttttcatacgccatagccaaaaatgatga
gattggcccacttggagctacaggcctcaccactcagtggtacgaatactcggatgggatgcggct
gcaggactcagtagttgaagtttggtgtaaaaatggagagatcaaatatctaatcagatgcgggag
ggaagccaggtatctggctgttctacacacgagagccttgccgacatctgtagtatttgaaaaaat
ttttgatgggaaagaacaagaggacatagtagaaatggatgacaactttgaattcggtctttgccc
gtgtgatgctagacccttgataaggggaaaatttaatacaacacttctaaatgggccagccttcca
gatggtttgccctataggatggacagggactgtaagctgtacactggccaataaggatacgttagc
cacaatcgttgtgagaacgtataagagggtcaggccttttccatataggcaggactgtgtcaccca
gaaaaccatcggggaagacctctacgactgtgccttaggagggaattggacttgtgtgccgggga
tgcactacgatatgtagctgggcccgttgagtcttgtgagtggtgtggttacaagtttttaaaag
tgagggtctgccgcatttcccaatcggcaaatgcaggctgaagaatgagagtggctatagacaagt
ggatgagacttcttgcaacagaaacggcgtggctatagtgccatctggcacggtcaaatgcaagat
aggggacacggtggtgcaagtcattgcaatggatgataaactagggcctatgccttgcaaaccaca
tgaaatcatatccagtgaggggccagtggaaaagacggcatgcaccttcaactacacaagaacatt
aaaaaacaagtactttgagcccagggataactattttcaacaatacatgttaaagggggagtacca
atattggtttgacctagagatcactgaccaccaccgagattacttcgctgagtccctgttggtgat
agtagttgcactcctgggtggcaggtacgtgctttggctgctggtcacatacatgatcttatcaga
acagatggcctcgggtgtccagtatggggcaggtgaaatagtgatgatgggcaacttgttaacaca
tgacagtgttgaagtggtgacatatttcttactactatacctactactaagagaggaaaacaccaa
aaaatgggtcatacttatataccacatcatagtaatgcatcctctaaaatcggtgacggtgatatt
gctaatggttgggggatggcaaaggctgaaccaggtgcccaggggtacctagagcaggtagacct

FIG. 6A

```
tagttttacgatgattacgatcatcgtaataggtctggttatagctaggcgtgatcccactgtggt
gccactagtcactatagtcgcggcactgaagatcacaggactaggctttgggcccggagtggatgc
agctatggcagttctcaccttaaccctactgatgactagttatgtgacagactacttcaggtataa
aaggtggatacaatgtatcctcagcttagtagccggggtgttccttatccggaccctcaaacatct
aggtgaactcaaaacccctgagctgaccataccaaattggaggccactaaccttcatactattata
cctgacttcagcaacagttgttacaagatggaaaattgatatagctggcatattcctgcaaggggc
ccctatccttttgatgatcgccaccctatgggctgacttcttgactcttgttctgatcctacccac
ctacgaattagccaagctgtactacctaaagaacgtcaagactgacgtggagaagagttggctggg
ggggttagactacaggacaattgactctgtctatgatgtggatgaaagtggagaaggcgtgtacct
cttcccgtccagacagaagaaaaataagaatatcagcatactcttgcccctcatcagagctacgct
aataagttgtattagcagcaaatggcagatggtgtatatggcttacttaaccctggactttatgta
ctacatgcacagaaaggttattgaagagatatcagggagtaccaatgtgatgtctagagtgatagc
agcacttatagaattaaactggtccatggaagaagaagagagcaagggcttaaagaagtttttat
actatctggaaggttgaggaaccttataataaagcataaggttaggaaccagactgtggcaagctg
gtatggggaggaagaagtctacggcatgccaaaagtcgtaaccataataagggcctgcacgctaaa
caagaacaaacattgcataatatgcacagtatgtgaggctagaaagtggaagggaggcaactgccc
taaatgcggccgccacgggaagcccatcatttgtgggatgactctagcggattttgaagaaaggca
ctacaagagaatttttataagggaaggtaactttgaaggacccttcaggcaggaatacaatgggtt
tgtacaatacaccgctagggggcaattgttcctgagaaatttacccatattggcaaccaaagtaaa
aatgatcatggtaggcaacctaggagaggaaatcggtgatctagaacacctaggatggatcctaag
gggacctgccgtgtgcaagaaaataactgagcacgaaaaatgccatgtcaacatactggacaagct
gactgcgtttttggagttatgccaagagggactacaccaagggctccggtgagattcccaacagc
actactaaaggtaaggaggggattggaaaccggttgggcttacacgcatcaaggtggcataagctc
agtagaccatgtgaccgctggcaaggatctattggtttgtgacagtatgggtagaactagagtggt
ttgccaaagcaacaacaagttaactgatgagacagaatatggtgtcaagacggactccggatgtcc
agatggtgccagatgctatgtattaaacccagaggcagtaaatatatcagggtccaagggagctgt
cgtacacctccaaaaaacgggtggggaatttacatgtgttactgcatcaggtacaccggccttctt
cgacctgaaaatttgaaaggatggtcgggtctacccatatttgaagcctccagcggcagagtggt
tggcagagtcaaagtgggaaagaatgaggaatccaaacccacaaaattaatgagtggtatccaaac
tgtttctaaaaatacggccgatttaacagaaatggtcaagaagataaccagcatgaacagggggga
ctttaggcagataacccttgcaacaggggcagggaagaccactgagctcccaaaagcagtgataga
ggagataggacgacacaaacgggtactagtgctcataccattaagagcagcagctgagtcagtcta
tcaatacatgagattgaaacacccaagtatctcctttaacctgagaataggggacatgaaagaagg
ggatatggcaaccgggatcacctacgcctcatatggatattttgccaaatgccacaaccaaagct
cagagcagcaatgatagagtattcatacatatttctggatgagtatcactgcgctactcctgagca
gttggctgttataggaaaaattcacagattttctgagagcataagagtggttgccatgactgccac
cccagcagggtcagtaaccacaacagggcaaaaacacccaatagaagaattcatagcccctgaggt
gatgaaaggggaggaccttggaagccagttccttgacatagcggggttaaagatccctgtagagga
gatgaagggtaacatgttggttttcgtgcccacgaggaacatggcagttgaagtagccaagaaact
aaaagccaagggctacaactcagggtattactacagtggggaagacccagctaacttgagagtggt
aacatcacagtccccatacgtcgtggtagccactaatgccatcgagtcaggggtaacgctgccaga
tttagatacagttgttgacacaggtctgaaatgtgagaagagggtgagggtgtcttccaaaatacc
ctttatagtaacaggccttaagagaatggctgtcactgtgggcgaacaggctcagcggagaggcag
ggtaggtagagtgaaacccggtaggtattatagaagtcaggaaacagcaaccgggtcaaaggacta
ccactatgacttgttacaggcacagaggtacgggatcgaagatgggatcaacgtaacaaagtcctt
tagggagatgaattatgactggagcctgtatgaggaagacagcttgctgataacccagctggagat
actgaacaatctactcatctctgaagatttaccagcagctgttaaaaacatcatggcaagaactga
tcacccagagcctatccagcttgcatataacagttatgaggtccaagtccctgtgctgttcccaaa
aataaggaatggggaggtcacagacacttacgagaactactcattcctaaatgcaaggaaactagg
ggaagacgtgcccgtgtacgtttatgccaccgaagatgaagatctggctgtggaccttctaggctt
ggactggccagacccagggaatcagcaagtagtggagactgggaaggcactgaagcaagtggtagg
actgtcctctgccgaaaatgccttgctcatagccctatttgggtatgtaggataccaagccttgtc
aaaaagacacgtcccaatgatcacagacatatacactatagaagatcaaagactagaggacacaac
ccaccttcaatatgcgcccaatgccataagaactgaggggaaggagactgaactaaaggaattagc
agtgggtgacttggacaaaatcatgggttccatctcggactatgcatcagagggattgaatttcgt
aaggtcccaagcagaaaagatgagatctgcccccgctttcaaagaaaacgtggaagctgctaaagg
gtacgtccaaaagtttattgattctctcatagaaaataaagaaaccataatcagatatggcctgtg
gggaacacacacggcactctacaagagtattgccgcgagattgggtcatgaaactgcattcgctac
```

FIG. 6B actagtgataaagtggctggccttcgggggtgagtcggtgtcagaccacatgagacaagcagctgt
cgacctggttgtttattatgtgatcaataagccctccttcccaggggattctgaaacccaacagga
aggaaggcgattcgtcgccagcctgttcatctccgctttggcaacctacacatacaaaacttggaa
ttacaacaacctctccaaggtagtagaaccagccttagcatacctcccctatgctaccaatgcact
aaaaatgtttaccccgaccagactggagagcgtagttatacttagtaccacaatatacaaaactta
cctctcaataaggaagggaaagagtgatggactgttgggtacagggatcagtgcagcaatggagat
tctatcacagaacccagtgtcggtaggtatatctgtcatgctgggggtgggggcgattgccgcgca
caatgccattgagtctagtgaacaaaaaaggaccctgttgatgaaagtgtttgtaaaaaacttcct
ggaccaggcggcaacagatgagctggtaaaggaaaacccagagaaaataataatggccctatttga
agcagtccagacaattggcaaccccttgaggctcatatatcacctgtatggggtttactacaaagg
ctgggaagcaaaagaactatcagagagaacagcaggcaggaacctgttcaccttgataatgttcga
agccttcgaactactagggatggactctgaagggaagataaggaacctgtctgggaattatgtcct
ggatttgatctacagcctacataaacagataaatagaggcttgaaaaaaatagtcttggggtgggc
tcccgcaccatttagttgcgactggactcctagtgatgagagaattaggttacccacaaacaacta
tctaagagtagaaactaagtgtccatgtggctatgagatgaaagcactaaggaacgttggtggcag
tcttaccaaagtggaggagaaaggacctttctctgcaggaacaggcttggtagagggccggtcaa
ctatagagtcacaaagtactatgatgacaacctcaaagagataaaaccagttgctaaactagaagg
atttgtggatcactattacaaaggtgttacagcaaggatagattatggcagagggaaaatgctatt
agctactgataaatgggaggtggagcacggtgttgtcactaggttggcaaagagatataccggagt
tggattcaagggagcatacctgggtgatgaacccaaccaccgcgacctagtagaaagagactgtgc
aactataacaaaaaatacagtgcagtttttaaaaatgaagaaaggctgtgcatttacctatgactt
aaccctgtccaatttaaccaggttaattgaattggtacacaaaaataacctagaagagaaagacat
accagcagccacagtaacgacatggctggcttatacttttgtaaatgaagatattgggactataaa
accagtactaggagagagagtggtcaccgacccagtggtggatgttaacttacaaccagaagtaca
agtggatacatcagaggttgggatcactttagttggtagggcagccttaatgacgacaggtactac
acccgtagtcgaaaaaacagagcccaatgctgatggtggtccaagctccataaagattgggttgga
tgaaggaagatacccaggacctggactgcaagaccgcaccttgaccgatgaaatacattctaggga
tgaaaggccctttgttctagtcctgggctcaaaaaattctatgtcaaatagagctaaaactgctag
aaacatcaacttatacaaggggaataaccccagggagattagagatctgatggcacaggggcgtat
gctagttgtggccttaaaggattttaaccctgagttgtctgaactagttgatttcaaggggacttt
cttagacagggaagccttggaagctctcagcctggggcggccaaagtccaagcaggtgaccacagc
cacagttagggagttattagagcaggaggtacaagttgagatccccagttggtttggagcaggtga
tccagtcttcttggaagtgactttgaagggtgacagatatcacttagtaggagatgtagatagagt
gaaagatcaagcgaaggagcttggggccacggaccagacaagaatagtgaaggaagtgggtgcaag
aacctataccatgaagctgtctagttggtttcttcaggcaacaaataaacagatgagcttgacccc
tttatttgaggagctattgctacgttgccccccctaaaataaagagcaataaagggcacatggcatc
agcttaccaactagcacagggaaactgggagccccttgactgtggagttcacctgggcaccatacc
tgccaggagggtaaaaatccacccatatgaagcttacctgaaactgaaggatttattggaagaaga
agaaaagaaaccaaagtgtagagacacagtaataagagaacacaacaagtggatcctcaaaaaagt
gaggcaccagggtaatctcaatacaaagaaaatcctcaaccctggaaagctatcagaacagctaga
tagagaagggcataaaagaaacatttataacaatcagattggcaccataatgacggaagcaggaag
taggttggaaaaattaccagtcgtcagagcccaaactgacactaaaagcttccatgaggcaatcag
agataagatagacaagaatgaaaatcagcagagcccaggactgcatgataaattgttagagatctt
tcatacaatagcccaacccagcctaagacacacctacagtgacgtgacgtgggagcaacttgaggc
aggggttaatagaaagggggctgctggctttctagagaagaagaatgttggagaagtactggactc
agagaagcacctggtggaacaactgatcagagatttgaaaacaggaaggaagataagatattatga
gacagcaataccaaaaaatgagaagagagatgtcagtgatgattggcaatcaggggacttagtaga
tgagaagaaaccaagggtgattcaataccctgaagctaaaacaagactagccatcactaaagtaat
gtacaactgggtgaaacagcagcccgtcgtgatcccagggtatgaagggaagaccccattatttaa
cattttcaacaaggtgaggaaggaatgggatttgttcaatgaaccagtagctgtgagtttcgacac
taaggcttgggacacccaagtaactagtagagatctacggcttattggtgaaattcaaaaatatta

FIG.6C

```
ctacaggaaagagtggcacaaattcatcgataccattactgaccatatggtggaggtgcccgtcata
acggcagatggtgaggtatacataagaaatggacaaaggggtagtggccagccagacacaagtgcag
gcaatagcatgctaaacgtgttaacaatgatgtatgccttctgtgaaagtacgggggttccatacaa
gagtttcaatagggttgcaaggatccatgtctgtggggatgacggcttcctaataacagagaagggg
ctgggattaaagtttgccaacaatgggatgcaaattctgcacgaagcaggcaagcctcaaaagataa
ctgaggggaaagaatgaaagttgcctataggttcgaggacatagaattctgctctcatacaccagt
ccccgttaggtggtctgataacaccagcagttacatggccggcagagacactgccgttatattatca
aagatggcaacaagattggattcaagtggagaaggggtactatagcatatgaaaaagcagtggcct
ttagtttttgctgatgtactcctggaatcctcttgtgaggaggatctgtctactggtcctttcaca
gcagccagagacaactccatcaacccagaccacttactattataaaggagacccaataggagcctac
aaagatgtaataggtaagaatttgtgtgaattaaaaaggacgggttttgaaaaattggccaatttaa
acctaagcctgtccacgttaggaatctggtccaaacatacaagtaaaagaatcatccaagactgtgt
aaccatcgggaaagaggaaggcaattggctggtcaatgccgacaggttgatatctagcaaaactggc
catttgtacatacctgacaaaggttatacattacaagggaaacattatgaacaacttcaactgcagg
caagaactagcccagtcacgggagtagggacggagagatataaactaggccctatagtaaacctgct
gctgaggaggttgagagttctgcttatggcagctgtcggtgccagcagttgaaataatgtatgtata
tattgtatataaatctgtatttgtatatattatgtttaaatacgtattaattaatttagttgagatt
agtagtgatatatagttatctacctcaagctaacactacactcaatgcacacagcactttagctgta
tgagggtacacccgacgtccacggttggactagggaaaacccttaacagcccc
```

INTRODUCED SnaBI AND PacI SITES

CLaI AND (PART OF) SmaI SITES USED TO INTRODUCE THE INSERT

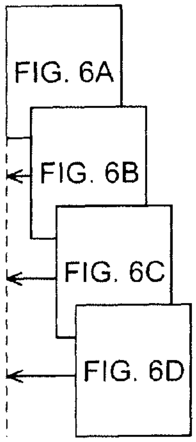

gtatacgaggttaggcaagttctcgtatacatattggacactctaaaaataattaggcctaggga
caaaaatcctccttagcgaaggccgaaaagaggctaaccatgcccttagtaggactagcaaaataa
ggggggtagcaacagtggcgagttcgttggatggctgaagccctgagtacagggtagtcgtcagtg
gttcgacgctttggaggacaagcctcgagatgccacgtggacgagggcatgcccacagcacatctt
aacctggacaggggtcgttcaggtgaaaacggtttaaccaaccgctacgaatacagtctgatagga
tgctgcagaggcccactgtattgctactgaaaatctctgctgtacatggcacatggagttgatcac
aaatgaacttttatacaaaacatacaaacaaaaacccgctggagtggaggaaccagtatacgacca
agctggtaaccctttgtttggagaaagaggagtgattcatccgcagtcaacgctaaaacttccaca
taaaagaggggagcgtgaagtccccaccaatctggcttctttaccaaaaagaggtgactgcaggtc
gggtaacagcaaggggcctgtgagtggaatctacttaaaaccagggccgttattctaccaagatta
taaaggacctgtctatcatagagccccattggagtttttgaggaggcgtctatgtgtgagacaac
taaaagaatagggagagtaactggtagtgacagcagattataccacatttacgtgtgtattgatgg
gtgcataatagtcaagagtgctacaaaagaccgccagaaagtactcaagtgggtccacaacaagct
aaactgccccctatgggtttcaagctgctccgacacaaaagatgaaggggtggtgaggaagaagca
acaaaagccagataggttggaaaaggggagaatgaagataacacctaaggagtcagagaaagacag
taagaccaagccgccagatgctacgatagtggtagatggagtcaagtatcaggtaaagaaaaaagg
aaaagtcaagagcaagaacacccaggacggcttataccacaacaaaaataaacctcaagagtcgcg
caagaaactagagaaagccctattggcctgggcaataatagccctggtttctttcaagtcacaat
gggagagaacataacgcaatggaacttacaagataatggaacggaaggcatacaacgagccatgtt
tcaaagaggagtgaatagaagtttacatgggatctggccagagaaaatctgtacaggtgttccttc
ccacctggccactgacacagaattgaaggcaattcatggtatgatggatgcaagtgagaagacaaa
ttatacgtgctgcagactccaacgccatgaatggaacaaacatggttggtgcaactggtacaacat
tgaaccttggatcctccttatgaataaaactcaggccaaccttactgagggtcagccactaaggga
gtgtgccgtcacatgccggtatgatcgagatagtgacctgaatgtagtaacacaagccagggatag
ccccacaccattaacaggttgcaagaaaggcaaaaacttttcctttgcaggcatattggtacaagg
gccttgcaactttgaaatagccgtaagtgatgtgctgttcaaagagcatgattgcactagtgtgat
tcaagacacagctcactacctcgtagacgggatgaccaactccctagagagtgccaggcaagggac
cgcgaaactaacaacttggctgggcaggcagcttgggatactaggaaagaaactggaaaacaagag
taagacatggtttggggcatatgcagcctctccctattgtgaggtagaacggaagcttggttacat
ctggtatacaaagaattgcactccagcctgtttgcctaggaatacaaagatcatcggccccggtag
gtttgacaccaatgccgaggatggtaaaatactgcatgagatggggggtcacttgtcggaggtgct
actactctcagtggtagtgctgtccgatttcgctccagagacagccagtgtgatatacttgattct
tcatttctccatcccacaaggacacactgatatacaagattgtgacaaaaaccaactaaacctcac
cgtagaactcacaacagcagaagtaataccaggctcagtttggaacttgggtaaatatgtttgtgt
aagaccagattggtggccttatgagacagccacagtcctggtgattgaagaggtgggtcaagtaat
taaggttgtcttaagggcgttaaaagatctgacgcgcatttggaccgctgctacaaccactgcatt
cttggtttgtctggtgaaggtagtgagaggccaagtgttacaaggtatactgtggctgatgctcat
aacaggggcgcaagggtacccagactgcaaacccggcttttcatacgccatagccaaaaatgatga
gattggcccacttggagctacaggcctcaccactcagtggtacgaatactcggatgggatgcggct
gcaggactcagtagttgaagtttggtgtaaaaatggagagatcaaatatctaatcagatgcgggag
ggaagccaggtatctggctgttctacacacgagagccttgccgacatctgtagtatttgaaaaaat
ttttgatgggaaagaacaagaggacatagtagaaatggatgacaactttgaattcggtctttgccc
gtgtgatgctagacccttgataaggggaaaatttaatacaacacttctaaatgggccagccttcca
gatggtttgccctataggatggacagggactgtaagctgtacactggccaataaggatacgttagc
cacaatcgttgtgagaacgtataagagggtcaggccttttccatataggcaggactgtgtcaccca
gaaaaccatcggggaagacctctacgactgtgccttaggagggaattggacttgtgtgccgggga
tgcactacgatatgtagctgggcccgttgagtcttgtgagtggtgtggttacaagtttttaaaaag
tgagggtctgccgcatttcccaatcggcaaatgcaggctgaagaatgagagtggctatagacaagt
ggatgagacttcttgcaacagaaacggcgtggctatagtgccatctggcacggtcaaatgcaagat
aggggacacggtggtgcaagtcattgcaatggatgataaactagggcctatgccttgcaaaccaca
tgaaatcatatccagtgaggggccagtggaaaagacggcatgcaccttcaactacacaagaacatt
aaaaaacaagtactttgagcccagggataactattttcaacaatacatgttaaagggggagtacca
atattggtttgacctagagatcactgaccaccaccgagattacttcgctgagtccctgttggtgat
agtagttgcactcctgggtggcaggtacgtgctttggctgctggtcacatacatgatcttatcaga
acagatggcctcgggtgtccagtatggggcaggtgaaatagtgatgatgggcaacttgttaacaca
tgacagtgttgaagtggtgacatatttcttactactatacctactactaagagaggaaaacaccaa
aaaatgggtcatacttatataccacatcatagtaatgcatcctctaaaatcggtgacggtgatatt
gctaatggttggggggatggcaaaggctgaaccaggtgcccaggggtacctagagcaggtagacct

FIG. 7A

```
tagttttacgatgattacgatcatcgtaataggtctggttatagctaggcgtgatcccactgtggt
gccactagtcactatagtcgcggcactgaagatcacaggactaggctttgggcccggagtggatgc
agctatggcagttctcaccttaaccctactgatgactagttatgtgacagactacttcaggtataa
aaggtggatacaatgtatcctcagcttagtagccggggtgttccttatccggaccctcaaacatct
aggtgaactcaaaacccctgagctgaccataccaaattggaggccactaaccttcatactattata
cctgacttcagcaacagttgttacaagatggaaaattgatatagctggcatattcctgcaaggggc
ccctatcctttgatgatcgccaccctatgggctgacttcttgactcttgttctgatcctacccac
ctacgaattagccaagctgtactacctaaagaacgtcaagactgacgtggagaagagttggctggg
ggggttagactacaggacaattgactctgtctatgatgtggatgaaagtggagaaggcgtgtacct
cttcccgtccagacagaagaaaaataagaatatcagcatactcttgcccctcatcagagctacgct
aataagttgtattagcagcaaatggcagatggtgtatatggcttacttaaccctggactttatgta
ctacatgcacagaaaggttattgaagagatatcagggagtaccaatgtgatgtctagagtgatagc
agcacttatagaattaaactggtccatggaagaagaagagagcaagggcttaaagaagtttttat
actatctggaaggttgaggaaccttataataaagcataaggttaggaaccagactgtggcaagctg
gtatggggaggaagaagtctacggcatgccaaaagtcgtaaccataataagggcctgcacgctaaa
caagaacaaacattgcataatatgcacagtatgtgaggctagaaagtggaagggaggcaactgccc
taaatgcggccgccacgggaagcccatcatttgtgggatgactctagcggattttgaagaaaggca
ctacaagagaatttttataagggaaggtaactttgaaggacccttcaggcaggaatacaatgggtt
tgtacaatacaccgctagggggcaattgttcctgagaaatttacccatattggcaaccaaagtaaa
aatgatcatggtaggcaacctaggagaggaaatcggtgatctagaacacctaggatggatcctaag
gggacctgccgtgtgcaagaaaataactgagcacgaaaaatgccatgtcaacatactggacaagct
gactgcgtttttttggagttatgccaagagggactacaccaagggctccggtgagattcccaacagc
actactaaaggtaaggaggggattggaaaccggttgggcttacacgcatcaaggtggcataagctc
agtagaccatgtgaccgctggcaaggatctattggtttgtgacagtatgggtagaactagagtggt
ttgccaaagcaacaacaagttaactgatgagacagaatatggtgtcaagacggactccggatgtcc
agatggtgccagatgctatgtattaaacccagaggcagtaaatatatcagggtccaagggagctgt
cgtacacctccaaaaaacgggtggggaatttacatgtgttactgcatcaggtacaccggccttctt
cgacctgaaaaatttgaaaggatggtcgggtctacccatatttgaagcctccagcggcagagtggt
tggcagagtcaaagtgggaaagaatgaggaatccaaacccacaaaattaatgagtggtatccaaac
tgtttctaaaaatacggccgatttaacagaaatggtcaagaagataaccagcatgaacaggggga
ctttaggcagataacccttgcaacaggggcagggaagaccactgagctcccaaaagcagtgataga
ggagataggacgacacaaacgggtactagtgctcataccattaagagcagcagctgagtcagtcta
tcaatacatgagattgaaacacccaagtatctcctttaacctgagaataggggacatgaaagaagg
ggatatggcaaccgggatcacctacgcctcatatggatatttttgccaaatgccacaaccaaagct
cagagcagcaatgatagagtattcatacatatttctggatgagtatcactgcgctactcctgagca
gttggctgttataggaaaaattcacagattttctgagagcataagagtggttgccatgactgccac
cccagcagggtcagtaaccacaacagggcaaaaacacccaatagaagaattcatagcccctgaggt
gatgaaaggggaggaccttggaagccagttccttgacatagcggggttaaagatccctgtagagga
gatgaagggtaacatgttggttttcgtgcccacgaggaacatggcagttgaagtagccaagaaact
aaaagccaagggctacaactcagggtattactacagtggggaagacccagctaacttgagagtggt
aacatcacagtccccatacgtcgtggtagccactaatgccatcgagtcaggggtaacgctgccaga
tttagatacagttgttgacacaggtctgaaatgtgagaagagggtgagggtgtcttccaaaatacc
ctttatagtaacaggccttaagagaatggctgtcactgtgggcgaacaggctcagcggagaggcag
ggtaggtagagtgaaacccggtaggtattatagaagtcaggaaacagcaaccgggtcaaaggacta
ccactatgacttgttacaggcacagaggtacgggatcgaagatgggatcaacgtaacaaagtcctt
tagggagatgaattatgactggagcctgtatgaggaagacagcttgctgataacccagctggagat
actgaacaatctactcatctctgaagatttaccagcagctgttaaaaacatcatggcaagaactga
tcacccagagcctatccagcttgcatataacagttatgaggtccaagtccctgtgctgttcccaaa
aataaggaatggggaggtcacagacacttacgagaactactcattcctaaatgcaaggaaactagg
ggaagacgtgcccgtgtacgtttatgccaccgaagatgaagatctggctgtggaccttctaggctt
ggactggccagacccagggaatcagcaagtagtggagactgggaaggcactgaagcaagtggtagg
actgtcctctgccgaaaatgccttgctcatagccctatttgggtatgtaggataccaagccttgtc
aaaaagacacgtcccaatgatcacagacatatacactatagaagatcaaagactagaggacacaac
ccaccttcaatatgcgcccaatgccataagaactgaggggaaggagactgaactaaaggaattagc
agtgggtgacttggacaaaatcatgggttccatctcggactatgcatcagagggattgaatttcgt
aaggtcccaagcagaaaagatgagatctgcccccgctttcaaagaaaacgtggaagctgctaaagg
gtacgtccaaaagtttattgattctctcatagaaaataaagaaaccataatcagatatggcctgtg
gggaacacacacggcactctacaagagtattgccgcgagattgggtcatgaaactgcattcgctac
```

FIG. 7B

```
actagtgataaagtggctggccttcgggggtgagtcggtgtcagaccacatgagacaagcagctgt
cgacctggttgtttattatgtgatcaataagccctccttcccaggggattctgaaacccaacagga
aggaaggcgattcgtcgccagcctgttcatctccgctttggcaacctacacatacaaaacttggaa
ttacaacaacctctccaaggtagtagaaccagccttagcatacctcccctatgctaccaatgcact
aaaaatgtttaccccgaccagactggagagcgtagttatacttagtaccacaatatacaaaactta
cctctcaataaggaagggaaagagtgatggactgttgggtacagggatcagtgcagcaatggagat
tctatcacagaacccagtgtcggtaggtatatctgtcatgctgggggtgggggcgattgccgcgca
caatgccattgagtctagtgaacaaaaaaggaccctgttgatgaaagtgtttgtaaaaaacttcct
ggaccaggcggcaacagatgagctggtaaaggaaaacccagagaaaataataatggccctatttga
agcagtccagacaattggcaaccccttgaggctcatatatcacctgtatggggtttactacaaagg
ctgggaagcaaaagaactatcagagagaacagcaggcaggaacctgttcaccttgataatgttcga
agccttcgaactactagggatggactctgaagggaagataaggaacctgtctgggaattatgtcct
ggatttgatctacagcctacataaacagataaatagaggcttgaaaaaaatagtcttggggtgggc
tcccgcaccatttagttgcgactggactcctagtgatgagagaattaggttacccacaaacaacta
tctaagagtagaaactaagtgtccatgtggctatgagatgaaagcactaaggaacgttggtggcag
tcttaccaaagtggaggagaaaggacctttttctctgcaggaacaggcttggtagagggccggtcaa
ctatagagtcacaaagtactatgatgacaacctcaaagagataaaaccagttgctaaactagaagg
atttgtggatcactattacaaaggtgttacagcaaggatagattatggcagagggaaaatgctatt
agctactgataaatgggaggtggagcacggtgttgtcactaggttggcaaagagatataccggagt
tggattcaagggagcatacctgggtgatgaacccaaccaccgcgacctagtagaaagagactgtgc
aactataacaaaaaatacagtgcagtttttaaaaatgaagaaaggctgtgcatttacctatgactt
aaccctgtccaatttaaccaggttaattgaattggtacacaaaaataacctagaagagaaagacat
accagcagccacagtaacgacatggctggcttatacttttgtaaatgaagatattgggactataaa
accagtactaggagagagagtggtcaccgacccagtggtggatgttaacttacaaccagaagtaca
agtggatacatcagaggttgggatcactttagttggtagggcagccttaatgacgacaggtactac
acccgtagtcgaaaaaacagagcccaatgctgatggtggtccaagctccataaagattgggttgga
tgaaggaagatacccaggacctggactgcaagaccgcaccttgaccgatgaaatacattctaggga
tgaaaggccctttgttctagtcctgggctcaaaaaattctatgtcaaatagagctaaaactgctag
aaacatcaacttatacaaggggaataaccccagggagattagagatctgatggcacaggggcgtat
gctagttgtggccttaaaggattttaaccctgagttgtctgaactagttgatttcaaggggacttt
cttagacagggaagccttggaagctctcagcctggggcggccaaagtccaagcaggtgaccacagc
cacagttagggagttattagagcaggaggtacaagttgagatccccagttggtttggagcaggtga
tccagtcttcttggaagtgactttgaagggtgacagatatcacttagtaggagatgtagatagagt
gaaagatcaagcgaaggagcttggggccacggaccagacaagaatagtgaaggaagtgggtgcaag
aacctataccatgaagctgtctagttggtttcttcaggcaacaaataaacagatgagcttgacccc
tttatttgaggagctattgctacgttgccccccctaaaataaagagcaataaagggcacatggcatc
agcttaccaactagcacagggaaactgggagccccttgactgtggagttcacctgggcaccatacc
tgccaggagggtaaaaatccacccatatgaagcttacctgaaactgaaggatttattggaagaaga
agaaaagaaaccaaagtgtagagacacagtaataagagaacacaacaagtggatcctcaaaaaagt
gaggcaccagggtaatctcaatacaaagaaaatcctcaaccctggaaagctatcagaacagctaga
tagagaagggcataaaagaaacatttataacaatcagattggcaccataatgacggaagcaggaag
taggttggaaaaattaccagtcgtcagagcccaaactgacactaaaagcttccatgaggcaatcag
agataagatagacaagaatgaaaatcagcagagcccaggactgcatgataaattgttagagatctt
tcatacaatagcccaacccagcctaagacacacctacagtgacgtgacgtgggagcaacttgaggc
aggggttaatagaaagggggctgctggctttctagagaagaagaatgttggagaagtactggactc
agagaagcacctggtggaacaactgatcagagatttgaaaacaggaaggaagataagatattatga
gacagcaataccaaaaaatgagaagagagatgtcagtgatgattggcaatcaggggacttagtaga
tgagaagaaaccaagggtgattcaataccctgaagctaaaacaagactagccatcactaaagtaat
gtacaactgggtgaaacagcagcccgtcgtgatcccagggtatgaagggaagaccccattatttaa
cattttcaacaaggtgaggaaggaatgggatttgttcaatgaaccagtagctgtgagtttcgacac
taaggcttgggacacccaagtaactagtagagatctacggcttattggtgaaattcaaaaatatta
```

FIG.7C

```
ctacaggaaagagtggcacaaattcatcgataccattactgaccatatggtggaggtgcccgtcat
aacggcagatggtgaggtatacataagaaatggacaaaggggtagtggccagccagacacaagtgc
aggcaatagcatgctaaacgtgttaacaatgatgtatgccttctgtgaaagtacggggttccata
caagagtttcaatagggttgcaaggatccatgtctgtggggatgacggcttcctaataacagagaa
ggggctgggattaaagtttgccaacaatgggatgcaaattctgcacgaagcaggcaagcctcaaaa
gataactgaggggaaagaatgaaagttgcctataggttcgaggacatagaattctgctctcatac
accagtccccgttaggtggtctgataacaccagcagttacatggccggcagagacactgccgttat
attatcaaagatggcaacaagattggattcaagtggagaaaggggtactatagcatatgaaaagc
agtggcctttagtttttgctgatgtactcctggaatcctcttgtgaggaggatctgtctactggt
cctttcacagcagccagagacaactccatcaacccagaccacttactattataaaggagacccaat
aggagcctacaaagatgtaataggtaagaatttgtgtgaattaaaaggacgggttttgaaaatt
ggccaatttaaacctaagcctgtccacgttaggaatctggtccaaacatacaagtaaaagaatcat
ccaagactgtgtaaccatcgggaaagaggaaggcaattggctggtcaatgccgacaggttgatatc
tagcaaaactggccatttgtacatacctgacaaaggttatacattacaagggaaacattatgaaca
acttcaactgcaggcaagaactagcccagtcacgggagtagggacggagagatataaactaggccc
tatagtaaacctgctgctgaggaggttgagagttctgcttatggcagctgtcggtgccagcagttg
aaataatgtatgtatatattgtatataaatctgtatttgtatatattatgtttaaatacgtagcca
gcccccgattgggggcgacactccaccatagatcactcccctgtgaggaactactgtcttcacgca
gaaagcgtctagccatggcgttagtatgagtgtcgtgcagcctccaggaccccccctctcgggaga
gccatagtggtctgcggaaccggtgagtacaccggaattgccaggacgaccgggtcctttcttgga
tcaacccgctcaatgcctggagatttgggcgtgcccccgcgagactgctagccgagtagtgttggg
tcgcgaaaggccttgtggtactgcctgatagggtgcttgcgagtgcctcgggaggtctcgtagacc
gtgcaccttaattaataatttagttgagattagtagtgatatatagttatctacctcaagctaaca
ctacactcaatgcacacagcactttagctgtatgagggtacacccgacgtccacggttggactagg
gaaaacccttaacagcccc
```

SnaBI SITE AND PacI SITES

CLaI AND (PART OF) SmaI SITES USED TO INTRODUCE THE INSERT

NUCLEOTIDE EXCHANGES (C WAS CHANGED INTO T) IN THE HCV 5′NTR TO REMOVE TWO INTERNAL SmaI SITES

SnaBI SITE AND PacI SITES

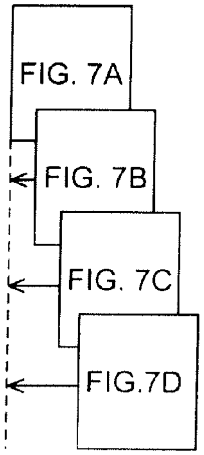

UGA-BOX UGA-BOX

TGAAATAATGTATGTATATATTGTATATAAATCTGTATTTGTATATATTATGTTTAAATTTAGTTGAGATTAGTAGTGAT
ATATAGTTATCTACCTCAAGCTAACACTACACTCAATGCACACAGCACTTTAGCTGTATGAGGGTACACCCG
ACGTCCACGGTTGGACTAGGGAAAACCCTTAACAGCCCC

FIG.8A

3'NTR OF BVDV-non-CP7

UGA-BOX UGA-BOX

TGAAATAATGTATGTATATATTGTATATAAATCTGTATTTGTATATATTATGTTTAAATACGTATTAATTAATTTAGTTGA
GATTAGTAGTGATATATAGTTATCTACCTCAAGCTAACACTACACTCAATGCACACAGCACTTTAGCTGTATGA
GGGTACACCCGACGTCCACGGTTGGACTAGGGAAAACCCTTAACAGCCCC

FIG. 8B

3'NTR OF BVDV-non-CP7 + CLONING SITE CHIMERA (SnaBI/PacI insert)

LEGEND

DOUBLE OVERSCORE = SNaBI
DOUBLE UNDERSCORE = PacI
UNDERSCORE = PSEUDO-STOP CODONS
ITALICS = *ADDITIONAL AND SPECIFICALLY CHANGED SEQUENCES*

UGA-BOX

UGA-BOX

TGAAATAATGTATGTATATATTGTATATAAATCTGTATTTGTATATATTATGTTTAAATACGTAGCCAGCCCCCGATT
GGGGGCGACACTCCACCATAGATCACTCCCCTGTGAGGAACTACTGTCTTCACGCAGAAAGCGTCTAGCC
ATGGCGTTAGTATGAGTGTCGTGCAGCCTCCAGGACCCCCCTC*T*CGGGAGAGCCATAGTGGTCTGCGGA
ACCGGTGAGTACACCGGAATTGCCAGGACGACCGGGTCCTTTCTTGGATCAACCCGCTCAATGCCTGGAG
ATTTGGGCGTGCCCCCGCGAGACTGCTAGCCGAGTAGTGTTGGGTCGCGAAAGGCCTTGTGGTACTGCCTG
ATAGGGTGCTTGCGAGTGCC*T*CGGGAGGTCTCGTAGACCGTGCACCTTAATTAA*TAA*TTTAGTTGAGATTAGTA
GTGATATATAGTTATCTACCTCAAGCTAACACTACACTCAATGCACACAGCACTTTAGCTGTATGAGGGTACA
CCCGACGTCCACGGTTGGACTAGGGAAAACCCTTAACAGCCCC

5'NTRHCV INSERT

LEGEND
DOUBLE OVERSCORE = SNaBI
DOUBLE UNDERSCORE = PacI
UNDERSCORE = PSEUDO-STOP CODONS
ITALICS = *ADDITIONAL AND SPECIFICALLY CHANGED SEQUENCES*

FIG. 8C

3'NTR OF BVDV-non-CP7-HCV 5'NTR CHIMERA

◇ BVDV-NON-CP7

○ BVDV-NON-CP7-HCV 5′NTR CHIMERA

TITER/ML (LOG 10)

0 1 2 3 4 5 6 7 8 9 10

10 20 30 40 50 60 70

TIME (H)

GROWTH CURVE

BVDV-NON-CP7

BVDV-NON-CP7-HCV 5′NTR CHIMERA

TITER/ML (LOG 10)

0 1 2 3 4 5 6 7 8 9 10

12 18 24 36 48 72

TIME (H)

GROWTH

BamHI SITE

GGATCCGCTGTCGGTGCCAGCAGTTGAAATAATGTATGTATATATTGTATATAAATCTGTATTTGTATATATTATGTTTA
AATACGTAGCCAGCCCCC*T**ATTGGGGGCGACACTCCACCATAGATCACTCCCCTGTGAGGAACTACTGTCTTCACGCAGA*
*AAGCGTCTAGCCATGGCGTTAGTATGAGTGTCGTGCAGCCTCCAGGACCCCCCCTCTCGGGAGAGCCATAGTGGTCTGCG*
*GAACCGGTGAGTACACCGGAATTGCCAGGACGACCGGGTCCTTTCTTGGATCAACCCGCTCAATGCCTGGAGATTTGGGC*
*GTGCCCCCGCGAGACTGCTAGCCGAGTAGTGTTGGGTCGCGAAAGGCCTTGTGGTACTGCCTGATAGGGTGCTTGCGAGT*
*GCCTCGGGAGGTCTCGTAGACCGTGCACC*TTAATTAATAATTTAGTTGAGATTAGTAGTGATATATAGTTATCTACCTCA
AGCTAACACTACACTCAATGCACACAGCACTTTAGCTG*TCTAGA*

XBaI SITE

FIG. 11A

G⟶T EXCHANGE IN HCV INSERT
CLONE 1, SEQUENCED: (FORWARD AND REVERSE SEQUENCES WERE IDENTICAL;
PCR FRAGMENT WAS CLONED BAMHI/XBAI)
*ITALICS* = HCV INSERT

BamHI SITE

*GGATCC*GCTGTCGGTGCCAGCAGTTGAAATAATGTATGTATATATTGTATATAAATCTGTATTTGTATATATT

ATGTTTAAATACGTA*GCCAGCCCCCGATTGGGGGCGACACTCCACCATAGATCACTCCCCTGTGAGGA*

*ACTACTGTCTTCACGCAGAAAGCGTCTAGCCATGGCGTTAGTATGAGTGTCGTGCAGCCTCCAGGACC*

*CCCCCTCTCGGGAGAGCCATAGTGGTCTGCGGAACCGGTGAGTACACCGGAATTGCCAGGACGACC*

*GGGTCCTTTCTTGGATCAACCCGCTCAATGCCTGGAGATTTGGGCGTGCCCCCGCGAGACTGCTAGC*

*CGAGTAGTGTTGGGTCGCGAAAGGCCTTGTGGTACTGTTCTGATAGGGTGCTTGCGAGTGCCTCGGGA*

*GGTCTCGTAGACCGTGCACC*TTAATTAATAATTTAGTTGAGATTAGTAGTGATATATAGTTATCTACCTCAA

GCTAACACTACACTCAATGCACACAGCACTTTAGCTG*TCTAGA*

XBaI SITE

FIG. 11B

C⟶T EXCHANGE IN HCV INSERT

CLONE 2, SEQUENCED: (FORWARD AND REVERSE SEQUENCES ARE IDENTICAL;
PCR FRAGMENT WAS CLONED BAMHI/XBAI)

*ITALICS* = HCV INSERT

BamHI SITE

*GGATCC*GCTGTCGGTGCCAGCAGTTGAAATAATGTATGTATATATTGTATATAAATCTGTATTTGTATATATT
ATGTTTAAATACGTA*GCCAGCCCCCGATTGGGGGCGACACTCCACCATAGATCACTCCCCTGTGAGGA*
*ACTACTGTCTTCACGCAGAAAGCGTCTAGCCATGGCGTTAGTATGAGTGTCGTGCAGCCTCCAGGACC*
*CCCCCTCTCGGGAGAGCCATAGTGGTCTGCGGAACCGGTGAGTACACCGGAATTGCCAGGACGACC*
*GGGTCCTTTCTTGGATCAACCCGCTCAATGCCTGGAGATTTGGGCGTGCCCCCGCGAGACTGCTAGC*
*CGAGTAGTGTTGGGTCGCGAAAGGCCTTGTGGTACTGCCTGATAGGGTGCTTGCGAGTGCCTCGGGA*
*GGTCTCGTAGACCGTGCACC*TTAATTAATAATTTAGTTGAGATTAGTAGTGATATATAGTTATCTACCTCAA
GCCAACACTACACTCAATGCACACAGCACTTTAGCTG*TCTAGA*

XBaI SITE

FIG. 11C

T→C EXCHANGE IN BVDV SEQUENCE
CLONE 3, SEQUENCED: (FORWARD AND REVERSE SEQUENCES ARE IDENTICAL; PCR FRAGMENT WAS CLONED BamHI/XbaI)
*ITALICS* = HCV INSERT

BamHI SITE

*GGATCC*GCTGTCGGTGCCAGCAGTTGAAATAATGTATGTATATATTGTATATAAATCTGTATTTGTATATATT
ATGTTTAAATACGTA*GCCAGCCCCCGATTGGGGGCGACACTCCACCATAGATCACTCCCCTGTGAGGA*
*ACTACTGTCTTCACGCAGAAAGCGTCTAGCCATGGCGTTAGTATGAGTGTCGTGCAGCCTCCAGGACC*
*CCCCCTCTCGGGAGAGCCATAGTGGTCTGCGGAACCGGTGAGTACACCGGAATTGCCAGGACGACC*
*GGGTCCTTTCTTGGATCAACCCGCTCAATGCCTGGAGATTTGGGCGTGCCCCCGCGAGACTGCTAGC*
*CGAGTAGTGTTGGGTCGCGAAAGGCCTTGTGGTACTGCCTGATAGGGTGCTTGCGAGTGCCTCGGGA*
*GGTCTCGTAGACCGTGCACC*TTAATTAATAATTTAGTTGAGATTAGTAGTGATATATAGTTATCTACCTCAA
GCTAACACTACACTCAATGCACACAGCACTTTAGCTG*TCTAGA*

XBal SITE

FIG. 11D

NO CHANGES

CLONE 4, SEQUENCED: (FORWARD AND REVERSE SEQUENCES ARE IDENTICAL; PCR FRAGMENT WAS CLONED BamHI/Xbal)

*ITALICS* = HCV INSERT

BamHI SITE

*GGATCC*GCTGTCG_TGCCAGCAGTTGAAATAATGTATGTATATATTGTATATAAATCTGTATTTGTATATATT
ATGTTTAAATACGTAGCCAGCCCCCGATTGGGGGCGACACTCCACCATAGATCACTCCCCTGTGAGGA
ACTACTGTCTTCACGCAGAAAGCGTCTAGCCATGGCGTTAGTATGAGTGTCGTGCAGCCTCCAGGACC
CCCCCTCTCGGGAGAGCCATAGTGGTCTGCGGAACCGGTGAGTACACCGGAATTGCCAGGACGACC
GGGTCCTTTCTTGGATCAACCCGCTCAATGCCTGGAGATTTGGGCGTGCCCCCGCGAGACTGCTAGC
CGAGTAGTGTTGGGTCGCGAAAGGCCTTGTGGTACTGCCTGATAGGGTGCTTGCGAGTGCCTCGGGA
GGTCTCGTAGACCGTGCACCTTAATTAATAATTTAGTTGAGATTAGTAGTGATATATAGTTATCTACCTCAA
GCTAACACTACACTCAATGCACACAGCACTTTAGCTG*TCTAGA*

XBal SITE

FIG. 11E

G DELETED IN BVDV SEQUENCE
CLONE 5, SEQUENCED: (FORWARD AND REVERSE SEQUENCES ARE IDENTICAL;
PCR FRAGMENT WAS CLONED BamHI/Xbal)
*ITALICS* = HCV INSERT

HCV VS. BVDV-NON-CP7-HCV 5'NTR CHIMERA
AS CALIBRATORS

WNV ASSAY WITH A BVDV-NON-CP7-HCV 5'NTR CHIMERA QS

GCTAATAATAACAGCCCCCTGATGGGGGCGACACTCCACCATGA
ATCACTCCCCTGTGAGGAACTACTGTCTTCACGCAGAAAGCGTC
TAGCCATGGCGTTAGTATGAGTGTCGTACAGCCTCCAGGACCCC
CCCTCTCGGGAGAGCCATAGTGGTCTGCGGAACCGGTGAGTACA
CCGGAATTGCCAGGACGACCGGGTCCTTTCTTGGATAAAACCCG
CTCAATGCCTGGAGATTTGGGCGTGCCCCCGCAAGACTGCTGGC
CGAGTAGTGTTGGGTCGCGAAAGGCCTTGTGGTACTGCCTGATA
GGGTGCTTGCGAGTGCCTCGGGAGGTCTCGTAGACCGTGCACC

FIG. 14A

HCV subtype 1a 5'NTR sequence

ACTAATAATAACCGCCCCTAATAGGGGCGACACTCCGCCATGAA
TCACTCCCCTGTGAGGAACTACTGTCTTCACGCAGAAAGCGTCT
AGCCATGGCGTTAGTATGAGTGTCGTACAGCCTCCAGGCCCCCC
CCTCTCGGGAGAGCCATAGTGGTCTGCGGAACCGGTGAGTACAC
CGGAATTGCCGGGAAGACCGGGTCCTTTCTTGGATAAACCCGCT
CTATGCCCGGCCATTTGGGCGTGCCCCCGCAAGACTGCTAGCCG
AGTAGCGTTGGGTTGCGAAAGGCCTTGTGGTACTGCCTGATAGG
GTGCTTGCGAGTGCCTCGGGAGGTCTCGTAGACCGTGCACC

FIG. 14B

HCV subtype 2a 5'NTR sequence

ACTAATAATAACTGCCTCTTACGAGGCGACACTCCACCATGGAT
CACTCCCCTGTGAGGAACTTCTGTCTTCACGCGGAAAGCGCCTA
GCCATGGCGTTAGTACGAGTGTCGTGCAGCCTCCAGGCCCCCCC
CTCTCGGGAGAGCCATAGTGGTCTGCGGAACCGGTGAGTACACC
GGAATCGCTGGGGTGACCGGGTCCTTTCTTGGAACAACCCGCTC
AATACCCAGAAATTTGGGCGTGCCCCCGCGAGATCACTAGCCGA
GTAGTGTTGGGTCGCGAAAGGCCTTGTGGTACTGCCTGATAGGG
TGCTTGCGAGTGCCTCGGGAGGTCTCGTAGACCGTGCAAC

FIG. 14C

HCV subtype 3a 5'NTR sequence

TTTAATAATAAGGGGGCGACACTCCACCATAGATCACTCCCCTG
TGAGGTACTACTGTCTTCACGCAGAAAGCGTCTAGCCATGGCAG
TTAGTATAGAGTGTCGTACAGCCTCCAGGACCCCCCCTCTCGGG
AGAGCCATAGTGGTCTGCGGAACCGGTGAGTACACCGGAATCGC
CAGGACGACCGGGTCCTTTCTTGGATAAACCCGCTCCATGCCTG
GAAATTTGGGCGTGCCCCCGCAAGACTGCTAAGCGAGTAGTGTT
GGGTCGCGAAAGGCCTTGTGGTACTGCCTGATAAGGTGCTTGCG
AGTCGCCGGGGAGGTACTCGTAGACCTGTGCACC

FIG. 14D

HCV subtype 4a 5'NTR sequence

ATTAATAATAAGATCACTCCCCTGTGAGGAACTACTGTCTTCAC
GCAGAAAGCGTCTAGCCATGGCGTTAGTATGAGTGTCGAACAGC
CTCCAGGACCCCCCCTCTCGGGAGAGCCATAGTGGTCTGCGGAA
CCGGTGAGTACACCGGAATTGCCGGGATGACCGGGTCCTTTCTT
GGATAAACCCGCTCAATGCCCGGAGATTTGGGCGTGCCCCCGCG
AGACTGCTAGCCGAGTAGTGTTGGGTCGCGAAAGGCCTTGTGGT
ACTGCCTGATAGGGTGCTTGCGAGTGCCTCGGGAGGTCTCGTAG
ACCGTGCACC

FIG. 14E

HCV subtype 5a 5’NTR sequence

GCTAATAATAACAGCCCCTAATGGGGCGACACTCCACCATGATC
ACTCCCCTGTGAGGAACTACTGTCTTCACGCAGAAAGCGTCTAG
CCATGGCGTTAGTATGAGTGTCGTGCAGCCTCCAGGATCCCCCC
TCTCGGGAGAGCCATAGTGGTCTGCGGAACCGGTGAGTTCACCG
GAATTGCCAGGACGACCGGGTCCTTTCTTGGATCAAACCCGCTC
AATGCCTGGAGATTTGGGCGTGCCCCCGCGAGACTGCTAGCCGA
GTAGTGTTGGGTCGCGAAAGGCCTTGTGGTACTGCCTGATAGGG
TGCTTGCGAGTGCCTCGGGAGGTCTCGTAGACCGTGCATC

FIG. 14F

HCV subtype 6p 5'NTR sequence

GATAATAATAAATCACTCCCCTGCGAGGAACCACTGTCCTCACG
CAGAAAGCGTCTAGCCATGACGTTAGTATGAGTGTCGTACAGCC
TCCAGGACCCCCCCTCTCGGGAGAGCCATAGTGGTCTGCGGAAC
CGGTGAGTACACCGGAATTGCCGGGAAGACTGGGTCCTTTCTTG
GATCAACCCACTCTATGCCCGGAGATTTGGGCGTGCCCCCGCGA
GACTGCTAGCCGAGTAGTGTTGGGTCGCGAAAGGCCTTGTGGTA
CTGCCTGATAGGGTGCTTGCGAGTGCCTCGGGAGGTCTCGTAGA
CCGTGCACC

FIG. 14G

HCV subtype 7a 5'NTR sequence

GATAATAATAAATCACTCCCCTGCGAGGAACCACTGTCCTCACG
CAGAAAGCGTCTAGCCATGACGTTAGTATGAGTGTCGTACAGCC
TCCAGGACCCCCCCTCTCGGGAGAGCCATAGTGGTCTGCGGAAC
CGGTGAGTACACCGGAATTGCCGGGAAGACTGGGTCCTTTCTTG
GATCAACCCACTCTATGCCCGGAGATTTGGGCGTGCCCCCGCGA
GACTGCTAGCCGAGTAGTGTTGGGTCGCGAAAGGCCTTGTGGTA
CTGCCTGATAGGGTGCTTGCGAGTGCCTCGGGAGGTCTCGTAGA
CCGTGCACC

FIG. 15

*Encephalomyocarditis* IRES - EGFP ORF insert (1325 bp)

Genomic Organization of chimeric BVDV-ECMV IRES- EGFP virus

MDBK cells infected with chimeric BVDV-ECMV IRES-EGFP virus and nuclei stained with DAPI MDBK cells infected with chimeric BVDV-ECMV IRES-EGFP virus and stained with antibody against BVDV NS3 protein EGFP fluorescence obtained from MDBK cells infected with chimeric BVDV-ECMV IRES-EGFP virus.

CHIMERIC PESTIVIRUS WITH INSERTION IN 3' NONTRANSLATED REGION (3'NTR) WITH STABLE REPLICATION AND RNASE RESISTANCE

CROSS-REFERENCE TO RELATED APPLICATIONS

This application is a 371 US national phase application of International Application No. PCT/US2009/065826 filed Nov. 24, 2009, which is a continuation application of U.S. application Ser. No. 12/277,282 filed Nov. 24, 2008, which disclosures are herein incorporated by reference in their entirety.

BACKGROUND OF THE INVENTION

An RNA virus has RNA (ribonucleic acid) as its genetic material, and infects host cells from bacteria, plants or animals, such as livestock and humans. The major criteria of how RNA viruses are classified are the sense and organization of the viral genome that determines the mode of viral RNA replication, including whether the viral RNA genome has positive (message) or negative sense, whether it is single or double stranded, and whether it is non-segmented or segmented.

Regulatory agencies often require that assays for detection of nucleic acids utilize quality control materials, including standards, calibrators and controls (Molecular Diagnostic Methods for Infectious Diseases; Approved Guideline, 2nd ed., Clinical and Laboratory Standards Institute, vol 26 (8), 2006). Quality control materials insure optimum performance and reliability of test results, including nucleic acid test (NAT) assays. Laboratories are required to demonstrate that assays for detection of viral RNA function properly as intended and are not affected by inhibition or other forms of interference. Controls for qualitative assays provide assurance of true negative and positive results while minimizing the chance for false positive and false negative results. In quantitative assays, controls ensure accuracy of results.

Ideally, the quality control material is as similar as possible in structure and morphology to the target analyte so both behave the same when tested. If controls, calibrators or standards behave like a patient sample on different diagnostic systems, they are considered "commutable" amongst these systems. Commutability is a key property of quality control materials that is especially important for calibrators and standards. The quality control material, however, should still be able to generate a signal that is distinguishable from that of the target analyte. Typically, viral RNA assays may have external run controls (positive or negative control) (EC), various types of internal controls (IC), or internal quantification or quantitation standards (QS), as well as calibrators. Internal and external control concepts are further described in CLSI Guideline MM3-A2 and U.S. Pat. No. 7,183,084 B2 and U.S. Pat. No. 7,192,745.

While PCR and other NAT techniques can test both DNA and RNA, there are technical challenges especially with quality control for RNA assays: 1) RNA is generally more labile than DNA, presenting additional technical difficulties for analytical RNA assays as compared to DNA assays. Naked RNA is sensitive to degradation through RNases, ubiquitously present RNA digesting enzymes. RNases can be found almost everywhere in the environment, however, they are especially prevalent in animal cells and fluids. To fully quality control all steps of an RNA assay, it is best to protect the RNA of the quality control material from potential degradation. An intact naturally occurring RNA virus, which does protect its RNA inside the virus, may be used as a calibrator or external positive run control, as long as its RNA sequence contains the primer and probe regions of the target virus. It may not be combined, however, with the test sample to be used as an internal control or quantitative standard, because it would cause a false positive signal.

It is also desirable that a RNA quality control material should be capable of monitoring the entire diagnostic process and serve as a "full process control", including nucleic acid isolation, reverse transcription, amplification and detection. The use of materials potentially infectious for humans is not desirable in a diagnostic kit due to safety concerns and shipping regulations. Internal Quality Standards (IQS) like Internal Controls (IC) and internal Quantification or Quantitation standards (QS) materials often can not be obtained from naturally occurring sources. The term "QS" is used in the literature as abbreviation for Quantification Standard, Quantitation Standard, internal Quantification Standard or internal Quantitation Standard, essentially all describing the same type of standard (see Clinical and Laboratory Standards Institute, CLSI Guideline MM3-A2 for details of QS use). This is particularly true for any IQS used as a "competitive" control, which utilizes the same primer sequence as the target RNA, but can be distinguished by a probe sequence different from the target sequence. Such IQS materials usually need to be artificially created. RNA itself is not as amenable to recombinant genetic engineering as DNA and usually requires a DNA intermediate. While it is known to transcribe RNA sequences from recombinant DNA sequences, it is difficult to package and protect these RNA transcript sequences from degradation by RNases.

One approach to solve the issues of RNA instability for quality control materials for RNA viral testing has been the use of RNase-resistant RNA recombinant RNA packaged in MS2 bacteriophage and having a single strand of MS2 RNA containing a recombinant heterologous RNA encapsidated by MS2 bacteriophage proteins to form a pseudo-viral particle. This approach has several disadvantages for use as a quality control material in analytical assays. Ideally, quality control materials should react like the tested analyte in an assay in order to monitor meaningfully all aspects of the procedure. However, the use of a bacteriophage as infected host is very different from that of many animal RNA viruses, e.g. HCV or HIV. A bacteriophage, which infects bacteria, is genetically distant to animal or other eukaryotic viruses. MS2 bacteriophage is not detergent sensitive, because it has a protein coat instead of a lipid bilayer. Many diagnostically relevant enveloped viruses causing harm to humans and livestock (e.g. HIV, Pestiviruses, West Nile Virus (WNV) or HCV) possess detergent sensitive outer envelopes. Because the armored RNA protein coat is very different biochemically from the lipid envelope of these animal viruses, the MS2 bacteriophage particles may behave differently from the targeted animal viral particles in analytical assays.

Recovery efficiency of RNA with the most commonly used silica based sample preparation methods is to a certain degree dependent on the length of the RNA. Most human RNA viruses, such as HCV, HIV or WNV, have about three times longer RNA genomes than armored RNA. Chimeric RNA viruses that are similar in structure to the virus being tested would be an ideal quality control material for RNA assays if they were genetically stable and could be grown in culture. In this method, a region of a targeted virus is inserted into the genome of another virus to form a chimeric virus. By testing for the inserted target region, the chimeric virus can function as a quality control material.

In designing a stable viral chimera, it is important to identify specific points of insertion in the compact viral genome that does not interfere with the viability of the virus. It is known that the choice of the specific target regions to be inserted, as well as the site for the insertion, can dramatically affect chimeric RNA viral functions, especially RNA replication, packaging of the RNA genome, virion stability, and virus infectivity. If the chimeric viral RNA replicates improperly, spontaneous sequence changes, such as deletions or frameshifts, may occur during replication in the RNA sequence of the virus chimera to form useless sequence revertants or pseudo-revertants. The ultimate genomic sequence of the revertant virus is unpredictable and may exclude part or parts of the applied insert. Unstable chimeric RNA virus, therefore, is usually not useful as a quality control material in an analytical RNA assay.

Examples of positive-strand ssRNA chimeras are known that utilize the 5' nontranslated region (5'NTR) and the open reading frame (ORF). Martin disclosed chimeric GBV-B/HCV (U.S. Pat. No. 7,141,405; US2006/0160067; US2006/0105365). Ilya et al. disclosed chimeric Eastern Equine Encephalitis virus and Sindbis virus (WO 2007/002793). Hong et al. describe HCV/BVDV chimeric constructs where the $N^{pro}$ protease gene is replaced (U.S. Pat. No. 6,326,137). Nam et al. disclosed HCV/BVDV constructs involving exchange of structural genes, especially E1, E2 or C. (U.S. Pat. No. 7,009,044). Rice and Kolykhalov (U.S. Pat. No. 6,127,116) disclosed that functional HCV clones can be used for the assay of HCV by constructing chimeric viruses using components of the IRES, proteases, RNA helicase, polymerase, or 3'NTR to create chimeric derivatives of BVDV whose productive replication is dependent on one or more of these HCV elements. None of these examples, however, disclosed stable Pestivirus RNA chimeras with insertion within specific regions of the 3'NTR.

Rice et al. disclosed a concept of constructing BVDV chimeras with inserted sequences from HCV (WO 99/55366; see also Frolov et al., 1998, RNA 4, 1418-1435). No data were given, however, that showed their chimeric constructs involving the 3'NTR were genetically stable. In Example 5 (WO 99/55366), Rice et al described a tandem 3'NTR construct where an HCV 3'NTR insert was placed downstream of the ORF and immediately followed by the intact 3'NTR of BVDV (FIG. 19). Rice et al. reported this 3'NTR HCV-BVDV tandem construct replicated poorly and revertants formed, which showed deletions when sequenced (FIG. 20). Significantly, Rice et al placed the HCV 3'NTR insert precisely downstream of the stop codon of the ORF of BVDV, not within the 3'NTR of BVDV. Rice et al., therefore, did not construct a replication competent BVDV chimera with insertion within the 3'NTR that was genetically stable and could be grown in culture.

Stettler et al. constructed a chimeric Pestivirus by insertion of foreign gene sequences within the 3'NTR at a site locate 11 nucleotides downstream of the reading frame of classical swine fever virus (CSFV) (Stettler et al., 202). The chimeric CSFV had normal wild type growth characteristics, were infections, and were stable through five passages. Stability and strength of expression of the IRES-EGFP insert are undetermined because Stettler et al. reported only a faint green fluorescence and no data disclosed the sequencing of the chimeric recombinant.

Recently, progress has been made in the development of (copy) cDNA clones of full-length BVDV genomes. These so-called "infectious BVDV cDNA clones" allow the in vitro transcription of infectious BVDV RNA genomes (Meyers, et al., J. Virology, 1996, 70: 8606-8613, erratum in J. Virol. 1997, 7 (2): 1735; Vassilev, et al., J. Virology, 1997, 71: 471-478; U.S. Pat. No. 6,001,613).

SUMMARY OF THE INVENTION

A quality control material for in vitro diagnostic assays preferably resembles the targeted animal or human RNA virus more than a bacteriophage derived pseudo-viral particle, is structurally and morphologically similar to the target RNA virus and thus behaves more like e.g. HCV, West Nile Virus (WNV) or HIV viruses. The 3'NTR of the genomic RNA of a Flaviviridae member, the Pestivirus BVDV, contains a region where a heterologous RNA sequence can be inserted to generate stable viral RNA chimeras and stable chimeric virus particles. Similar to the wild-type BVDV virus particles, the chimeric virus particles with a heterologous insertion in the 3'NTR of the viral RNA genome after the SL strap stem loop are sequence stable, replication-competent, resistant to RNases, and infectious.

Useful and stable Pestivirus RNA chimeras are constructed from an understanding of the viral RNA genome to identify areas within the 3'NTR for stable insertion of heterologous sequences. Defined areas within the 3'NTR of the genomic RNA, particularly downstream of the 5' UGA box, of a Flaviviridae member, the Pestivirus BVDV, is used to create a stable chimeric virus, that is useful in an analytical viral assay. A stable chimeric Pestivirus can be utilized as a viral quality control material that is similar in genomic composition and virion composition to the RNA virus being tested.

The detailed "signal" function of the different elements of the 3'NTR of Pestivirus genomic RNA is used to generate a stable replication-competent BVDV chimera containing a site-specific heterologous sequence within the 3'NTR of the genomic RNA. The heterologous insertion is preferably made within the 3'NTR variable region (3'V) after the $SL_{stop}$ stem loop, and most preferably, the insertion is made in a defined sequence region located downstream of the $UGA_{pos.cons}$ box (Isken et al., 2004). This insertion site is located downstream of the region that was experimentally shown with the BVDV DI9c replicon RNA (Isken et al., 2004) to form the $SL_{stop}$ (SLIII) structure and that is proposed by RNA folding programs such as mfold 3-1 (http://www.bioinfospi.edu/~zukerm/export/) to form $SL_{stop}$ (SLIII) with the genomic RNA of all other Pestivirus members. The insertion site is located upstream of the region that was experimentally shown with the BVDV DI9c replicon RNA to form the SLII structure and that is proposed by the RNA folding program mfold 3-1 to fold SLII with the genomic RNA of all other Pestivirus members. (Grassmann, C., Yu, H., Isken, O., and Behrens, S.-E. (2005). Hepatitis C virus and the related bovine viral diarrhea virus considerably differ in the functional organization of the 5' non-translated region: implications for the viral life cycle. Virology 333: 349-366.; Isken, O., Grassmann, C. W., Sarisky, R. T., Kann, M., Zhang, S., Grosse, F., Kao, P. N., and Behrens, S.-E. (2003). Members of the NF90/NFAR protein group are involved in the life cycle of a positive-strand RNA virus. EMBO J. 22: 5655-5665.; Isken, O., Grassmann, C. W., Yu, H., and Behrens, S.-E. (2004). Complex signals in the genomic 3' non-translated region of bovine viral diarrhea virus coordinate translation and replication of the viral RNA. RNA 10: 1637-52.; Isken, O., Baroth, M., Grassmann, C. W., Weinlich, S., Ostareck, D. H., Ostareck-Lederer, A. and Behrens, S.-E. (2007). Nuclear factors are involved in hepatitis C virus RNA replication. RNA 13: 1675-1692.)

The location of the $UGA_{pos.cons.}$ box is conserved in the genomes of all Pestivirus 3'NTRs (Becher, et al., J. Virology, 1998, 72 (6): 5165-73.; Isken, et al., 2003; Isken, et al., 2004).

Given the general structural alignment of the $UGA_{pos.cons.}$ box, the stem-loop structures $SL_{stop}$ (SLIII), SLII and SLI, and other structural elements within the 3'NTR of Pestivirus, the construction of chimeric virus is not only applicable to the Pestivirus BVDV but to all Pestivirus members.

BRIEF DESCRIPTION OF THE FIGURES AND TABLES

FIG. 1 shows a comparison of the genomic organization of Hepacivirus HCV and Pestivirus BVDV viruses. The 5' NTR (IBES) and 3'NTRs are indicated as single lines, and the open reading frame (ORF) for the viral polyprotein is schematized as boxes, with the different viral proteins indicated within the boxes. The enzymatic activities that proteolytically mature the viral polyprotein are designated as autoprotease (A); cellular signalase (closed oval), and viral protease (arrow).

FIG. 2 is a schematic diagram of the secondary structures of the HCV and BVDV NTRs flanking the ORF, which is shown as a box. The area of the HCV 5'NTR is enclosed with a long-dashed line, and the area of the BVDV 3'NTR is indicated with a dotted line. An arrow indicates that the HCV 5'NTR was inserted within the region of the 3'NTR of BVDV.

FIG. 3 shows a schematic of the secondary structure of the 3'NTR of Pestivirus BVDV (SEQ ID NO: 19) and of proposed functions of this region during viral replication. The sequence (taken from the BVDV replicon construct DI9c; Behrens et al., 1998; Behrens, S.-E., Grassmann, C. W., Thiel, H.-J., Meyers, G., and Tautz, N. 1998 Characterization of an autonomous RNA replicon of a Pestivirus. J. Virol. 72: 2364-2372) reads 5' to 3' in direction. The UGA translational stop codon and the so-called "pseudo-stop codons" are boxed with a thin line, and the UGA boxes found in this isolate are boxed with a heavy line. The stem-loop structures, which were determined experimentally, are labeled SLstop, SLII and SLI (Isken et al., 2004, Yu et al., 1999; Yu, H., Grassmann, C. W., and Behrens, S.-E. 1999 Sequence and structural elements at the 3' terminus of the bovine viral diarrhea virus: functional role during RNA replication. J. Virol. 73: 3638-3648). The 3' variable (V) region and the 3' constant (C) region are indicated; the border is indicated by an arrow (according to sequence alignments by Deng and Brock, 1993 (Deng R, Brock K V. Nucleic Acids Res. 1993 April 25:21(8):1949-57). A translating ribosome is indicated by a double structure at the 5' end of the 3'NTR, indicating that ribosomes terminate at the position of the translation termination codon. The following double line indicates that the 3'V region is involved in efficient termination of translation at the translational stop codon (Isken et al., 2004). The NFAR protein binding site is indicated by a group of circles, and the site where the viral replication complex presumably forms is indicated by a large oval (Isken et al., 2004. The heterologous RNA sequence may be inserted within the 3'NTR. A preferred site of insertion of the HCV 5'NTR within the 3'NTR is indicated by a thick arrow.

FIG. 4 is a schematic diagram of the 3'NTR of Pestivirus BVDV (SEQ ID NO: 19). As in FIG. 3, the sequence and secondary structure information are derived from the BVDV D19c replicon (Behrens et al., 1998; Yu et al., 1999). The 3' variable [3'V (1-90 nt)] and the 3' constant [3'C regions (91-192 nt)] are indicated. The stem-loop structures: SLSTOP, SLII and SLI are labeled. The UGA translational stop codon and the pseudo-stop codons are boxed. The UGA box motifs within the 3'V are shown boxed with a heavy line, including the 5'UGA box, the UGApos.cons. box and the 3'UGA-like box (Isken et al., 2003; Isken et al., 2004). A preferred site of insertion of the HCV 5'NTR within the 3'NTR is indicated by a thick arrow.

FIG. 5A shows a schematic sequence alignment of the 3'NTRs of various Pestivirus strains, including BDV X818 (SEQ ID NO: 13), CSFV C-strain (SEQ ID NO: 14), CSFV Alfort-T (SEQ ID NO: 15), BVDV type 1 NADL (SEQ ID NO: 16), BVDV type 1 Osloss (SEQ ID NO: 17) and BVDV type 2 890 (SEQ ID NO: 18). For all these Pestivirus strains, the positions that form the stem-loop structures SLstop (SLIII) and SLII are indicated. Nucleotides that are 100% conserved between the different strains are indicated with an asterisk (*). The UGApos.cons. box is boxed. A thin arrow indicates a preferred site between the SLstop (SLIII) and SLII stem-loop structures for the insertion of heterologous RNA sequence within the 3'NTR. A thick arrow indicates the border between the 3'V and 3'C regions within the 3'NTRs (Deng and Brock, 1993). FIG. 5B shows a sequence alignment of UGA box sequences in the 3'NTRs of various Pestivirus strains (SEQ ID NOS: 20-31) (Isken et al., 2003). 100% conserved nucleotides are boxed. The consensus sequence for the twelve nucleotides from this sequence alignment of the UGA boxes is indicated.

FIG. 6 shows the cDNA sequence of the BVDV-non-CP7-HCV 5'NTR chimera (SEQ ID NO: 3) with the restriction endonuclease sites for ClaI, part of SmaI, SnaBI and PacI indicated. The nucleotide exchanges (c changed into t) are also indicated.

FIG. 7 shows the cDNA sequence of the BVDV-non-CP7+ cloning site chimera (SEQ ID NO: 4) with the restriction endonuclease sites for ClaI, part of SmaI, SnaBI and PacI indicated.

FIG. 8 shows the sequence compositions of the 3'NTR for: (A) Pestivirus BVDV-non-CP7 (SEQ ID NO: 5), (B) the BVDV-non-CP7+ cloning site chimera (SEQ ID NO: 6), and (C) BVDV-non-CP7-HCV 5'NTR chimera (SEQ ID NO: 7). Provided are the sequences of the 3' non-translated regions (3'NTRs) of: the BVDV non-CP7 cDNA (starting material; wild type) (FIG. 8A), the BVDV non-CP7 cDNA+ cloning site chimera (FIG. 8B), which is a recombinant cDNA containing the inserted SnaBI and PacI restriction sites at pos 12134-12148), and) the recombinant cDNA of the Pestivirus BVDV-non-CP7-HCV 5'NTR chimera (FIG. 8C) containing the inserted HCV 5'NTR (HCV sequence subtype Ib (Lohmann et al., Science 1999 July 2: 285 (5424): 110-3) plus SnaBI and PacI sites inserted at pos. 12134-12492. Note that two SmaI sites in the HCV insert were inactivated by two site-directed nucleotide exchanges (c to t exchanges at positions 12269 and 12456 of the BVDV-non-CP7-HCV 5'NTR chimera sequence; see SEQ ID NO: 2 for the cDNA of HCV 5'NTR). This was done to enable linearization of the chimeric BVDV cDNA construct by a single SmaI site at the 3'-end of the cDNA for run-off in vitro transcription by SP6 RNA polymerase. The translation stop codon (tga) is boxed; pseudo-stop codons are underlined; restriction endonuclease sites are bracketed, the restriction endonuclease sites SnaBI (tacgta) and PacI (ttaattaa) are indicated; the UGA-box motif sequences are shown in bold and boxed with dashed lines; the 5'NTR HCV insert is shown in a large boxed region. Sites that were added or modified, such as the taa site following the Pac site, are indicated in italics.

Figure 9:
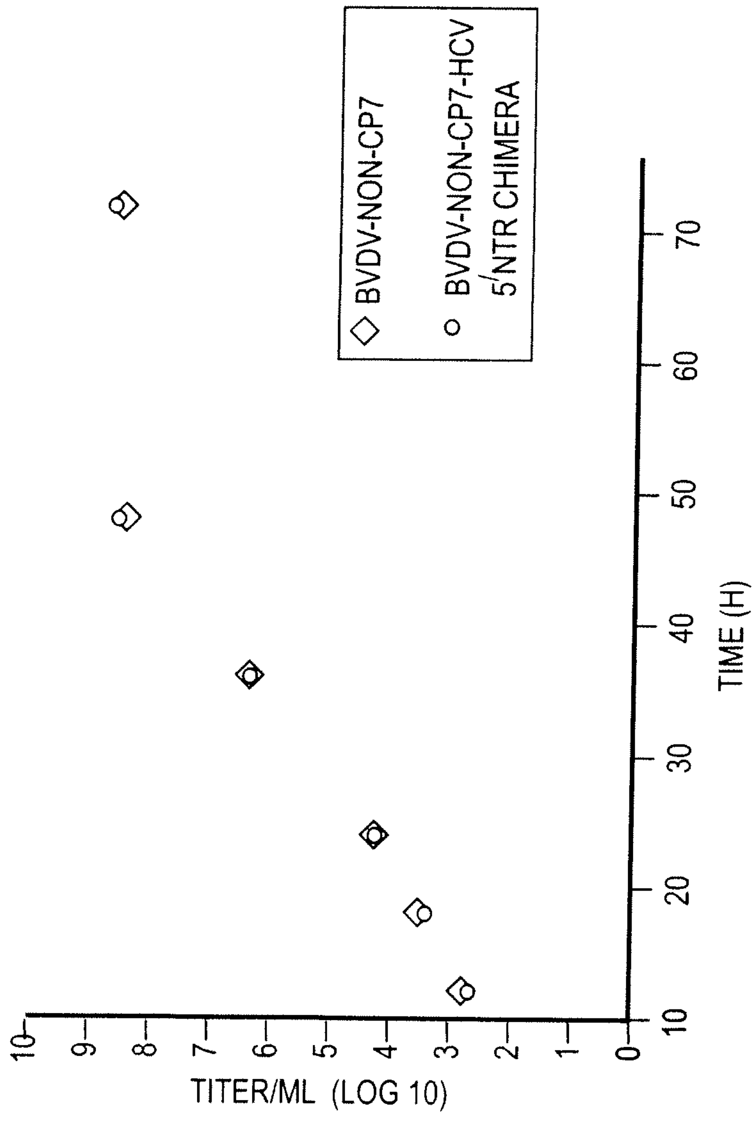

FIG. 9 shows growth curves obtained for the BVDV-non-CP7 (open diamonds) and the BVDV-non-CP7-HCV 5'NTR chimera (open circles).

Figure 10:
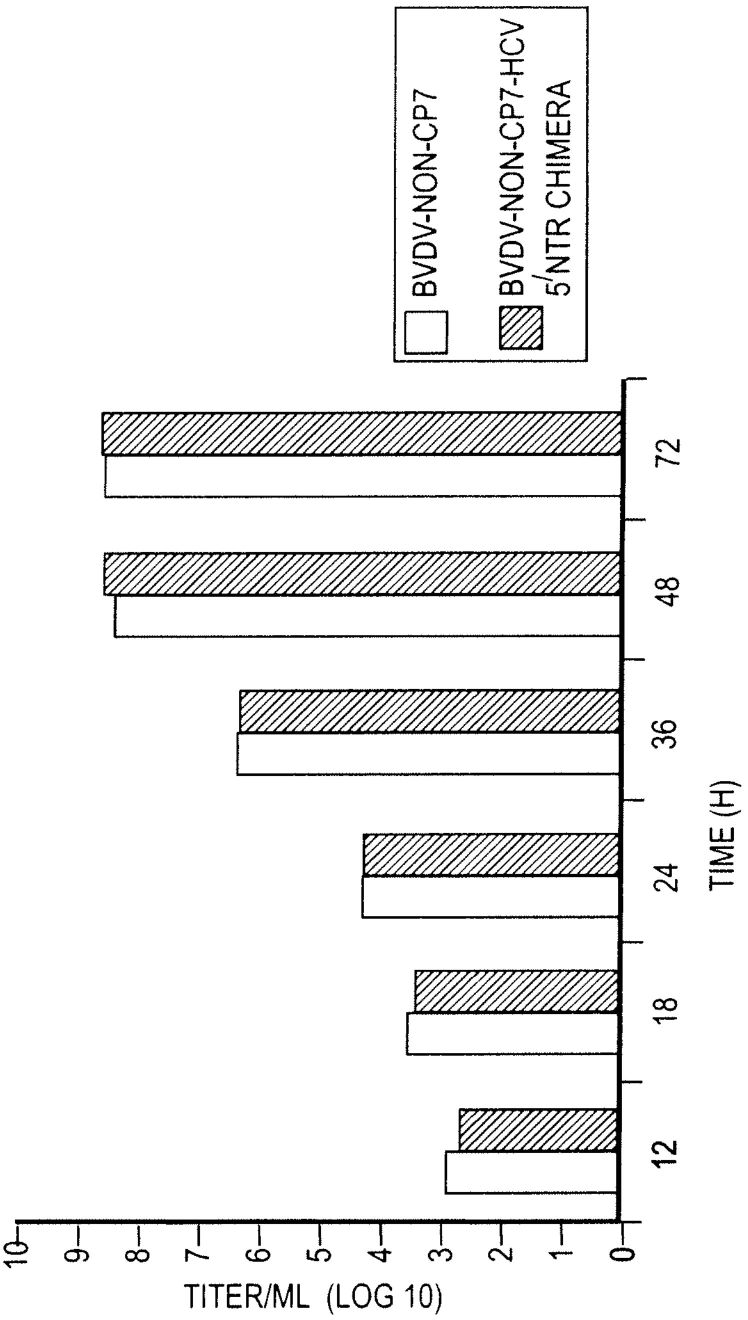

FIG. 10 shows growth curve data in bar graph format for the BVDV-non-CP7 (open bar) and the BVDV-nonCP7-HCV-5'NTR chimera (cross-hatched bar).

FIG. 11 shows sequence information obtained for five viral isolates following seven passages of re-infections. Following RT-PCR of total viral RNA isolated from infected cells after seven (7) passages of re-infections, the PCR fragment was cloned using BamHI and XbaI. Five clones were sequenced. The details of the sequence changes observed in these five clones are shown in FIGS. 11A-11E (SEQ ID NOS: 8-12, respectively).

Figure 12:
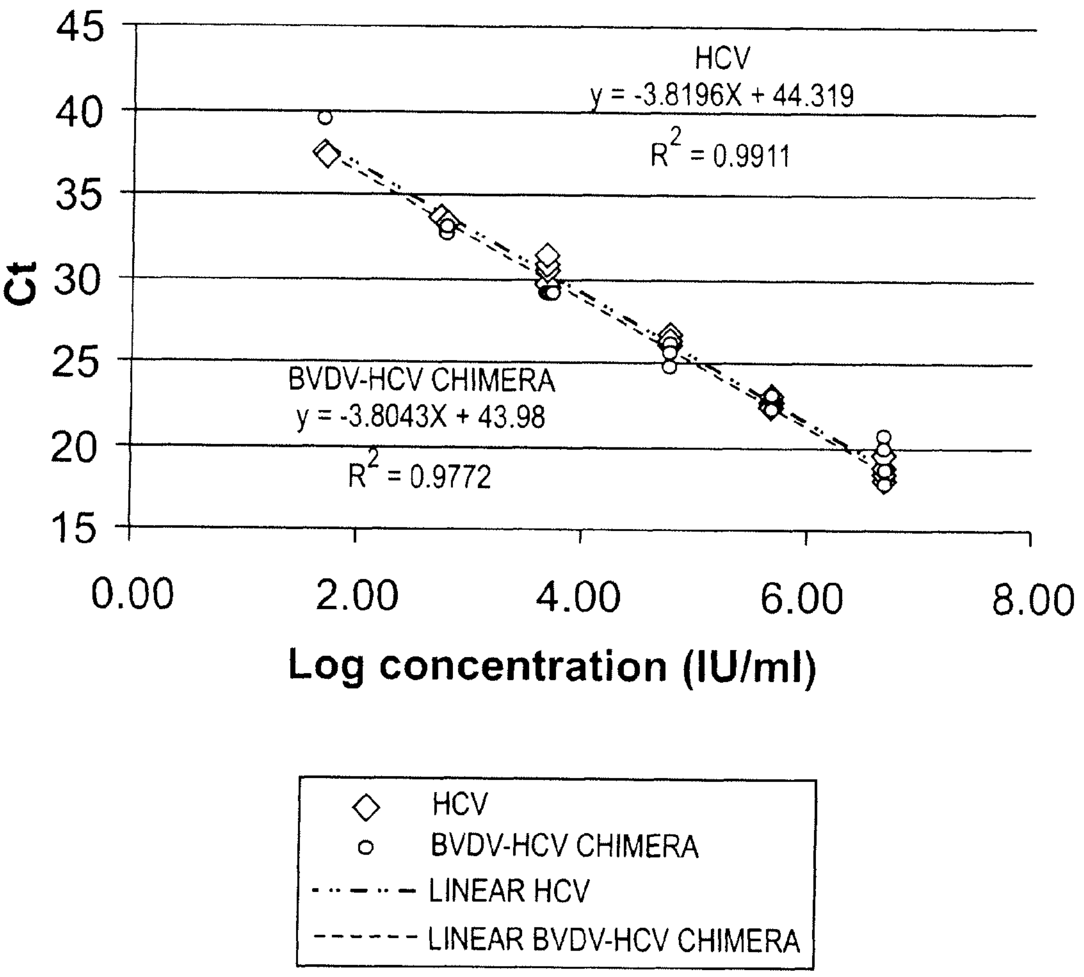

FIG. 12 shows the signals obtained for the use of Pestivirus BVDV-non-CP7-HCV 5'NTR chimera and a known HCV control as a calibrator. The measured Ct values for both calibration panels were plotted against the log of the expected international units (IU). The equations of the linear regression fit lines were equivalent within the measurement error: y=−3.80 x+44.0 for HCV-BVDV; y=−3.82x+44.3 for OptiQuant HCV.

Figure 13:
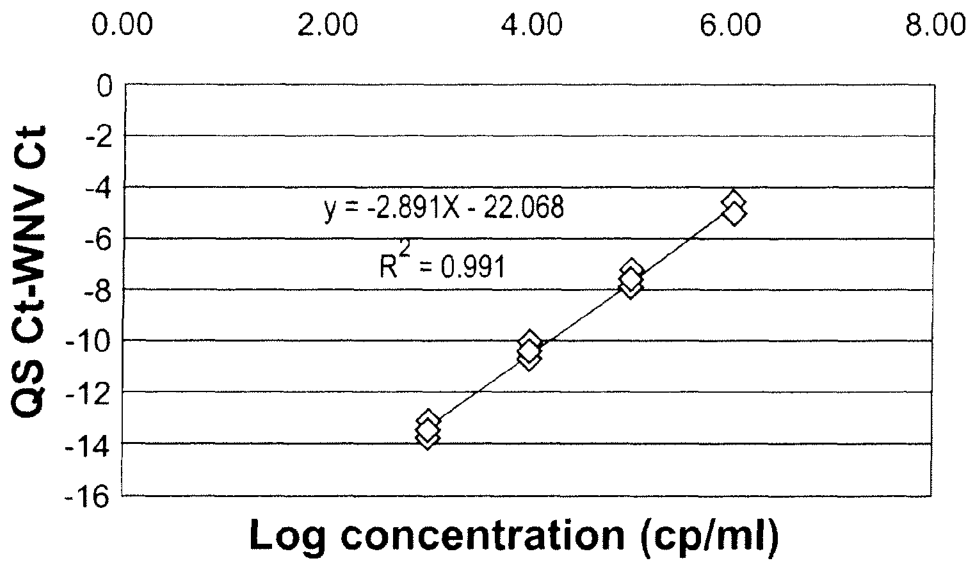

FIG. 13 shows the results of linear regression analysis of a West Nile Virus (WNV assay) with HCV-BVDV chimeric RNA as an internal quantification standard (QS). A slope of 2.891 and a coefficient of determination of 0.996 was obtained.

FIGS. 14A-14G show the HCV subtype 5'NTR sequences that were inserted into the BVDV 3'NTR: FIG. 14A, HCV subtype 1a (SEQ ID NO: 13); FIG. 14B, HCV subtype 2a (SEQ ID NO: 14); FIG. 14C, HCV subtype 3a (SEQ ID NO: 15); FIG. 14D, HCV subtype 4a (SEQ ID NO: 16); FIG. 14E, HCV subtype 5a (SEQ ID NO: 17); FIG. 14F, HCV subtype 6p (SEQ ID NO: 18), and FIG. 14G, HCV subtype 7a (SEQ ID NO: 19).

FIG. 15 shows the sequence for the Encephalomyocarditis (ECMV) IRES-EGFP open reading frame insert of 1325 bp (SEQ ID NO: 20) that was introduced into BVDV 3'NTR.

Figure 16:
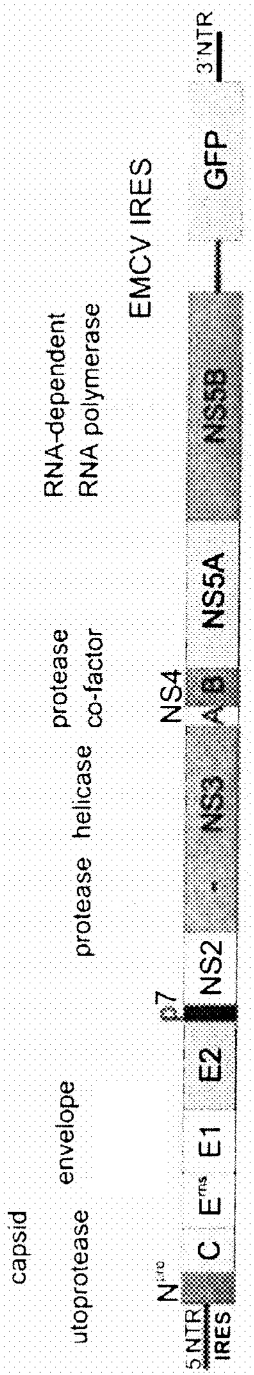

FIG. 16 shows the genomic organization of the chimeric BVDV-ECMV IRES-EGFP virus.

Figure 17A:
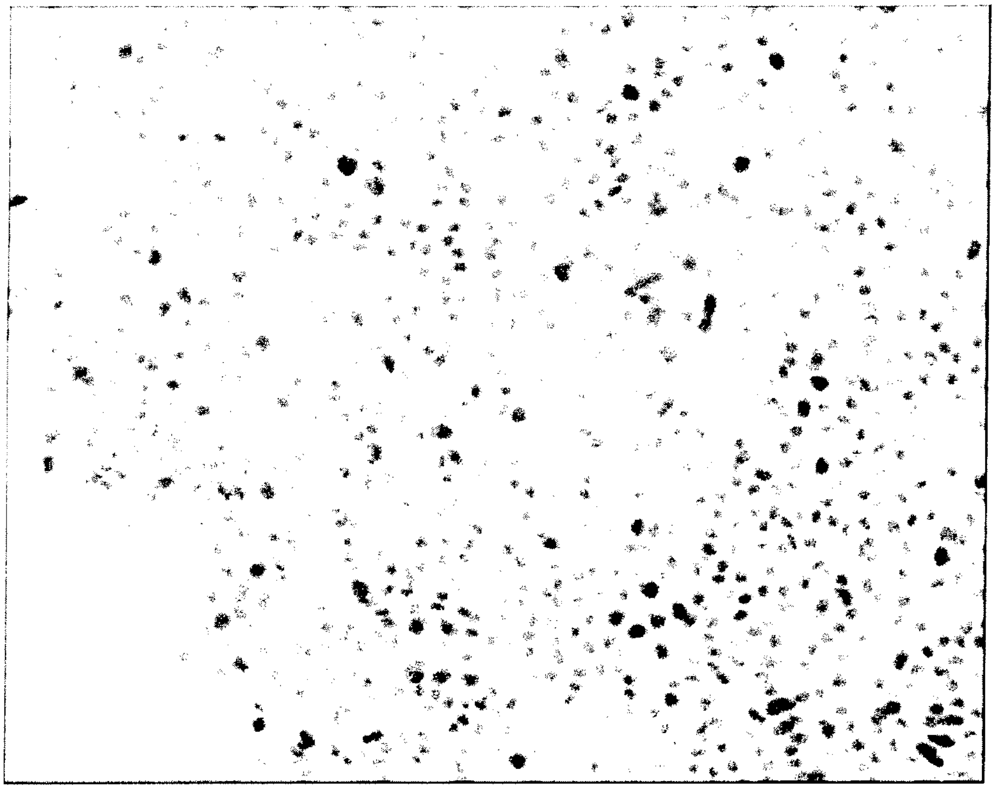
Figure 17B:
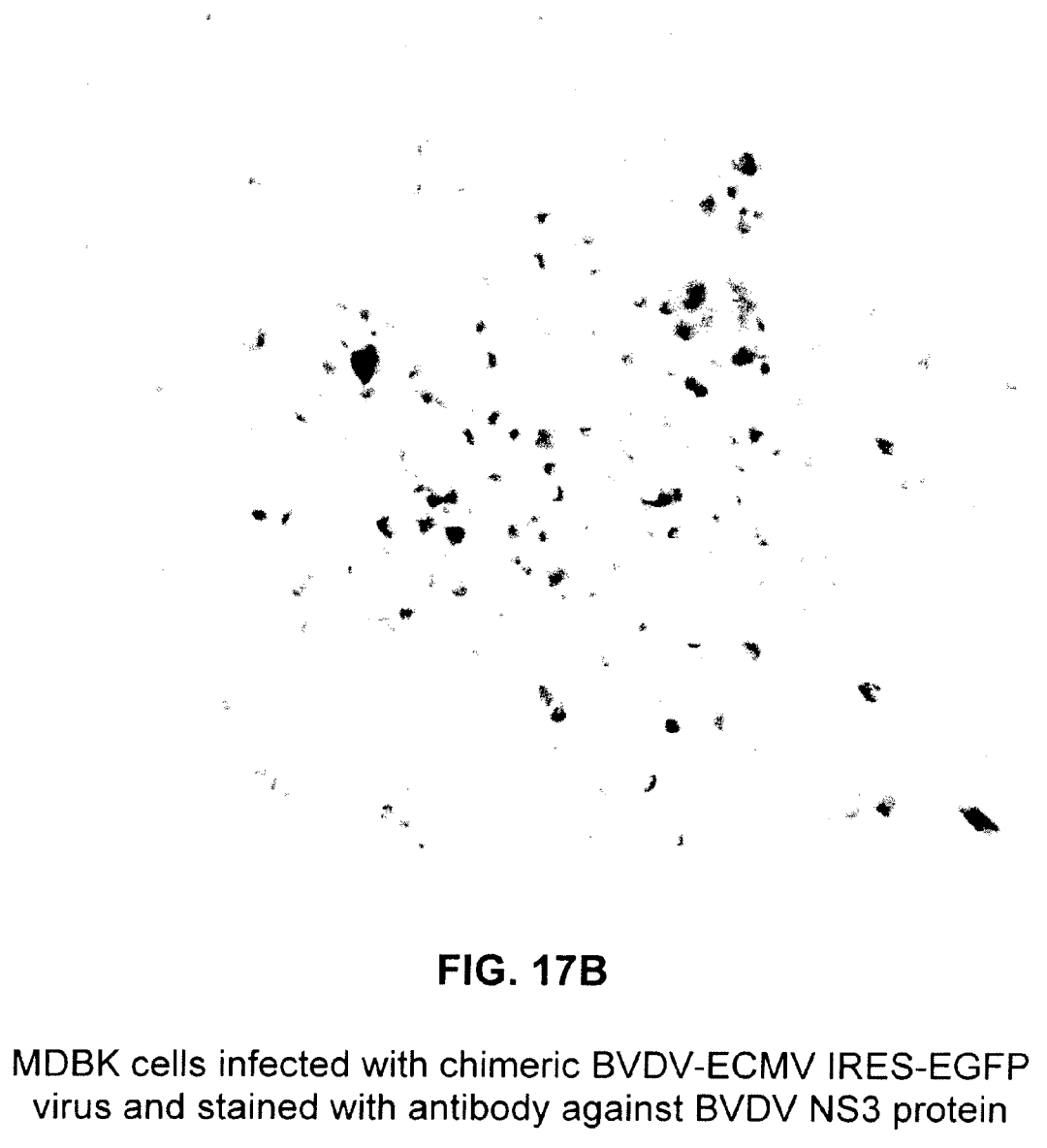
Figure 17C:
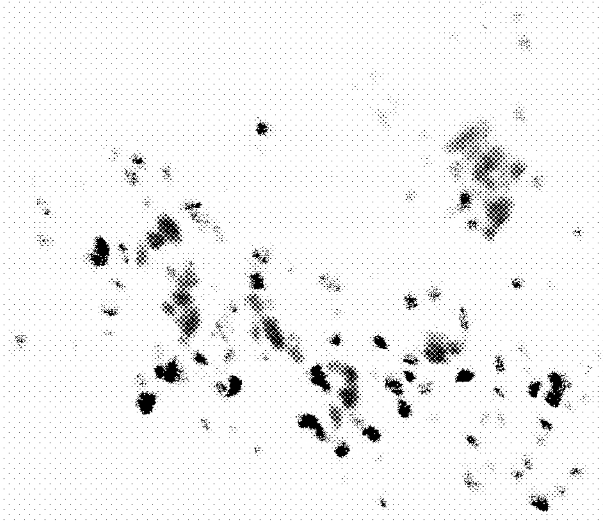

FIGS. 17A-17C shows the histological results obtained for MDBK cells infected with the chimeric BVDV-ECMV IRES-EGFP virus. FIG. 17A shows nuclei of infected MDBK cells stained with DAPI stain (light and dark gray areas); FIG. 17B shows infected MDBK cells stained with antibody against BVDV NS3 protein (light and dark gray areas); and FIG. 17C shows the clearly detectable EGFP fluorescence obtained from infected MDBK cells indicating high levels of expression of the inserted heterologous EGFP gene in the MDBK cells (green fluorescence shown in black and white as light and dark gray areas).

Table 1 shows virus titers obtained for BVDV-non-CP7 and BVDV-non-CP7+ cloning site chimera at three days post infection (1st re-infection).

Table 2 shows virus titers obtained for BVDV-non-CP7 and the BVDV-non-CP7-HCV 5'NTR chimera at three days post transfection of viral RNA into MDBK cells. Moreover, virus titers are shown at three days post infection of MDBK cells measured in the course of several re-infection experiments with virus-containing supernatant as indicated. Up to seven re-infection experiments were performed.

Table 3 shows the data for growth curves shown in FIGS. 10 and 11.

Table 4 shows the non-infectivity data obtained for the BVDV-non-CP7-HCV-5'NTR chimera at various times and at three different temperatures of treatment with indicated concentrations of β-propiolactone. Immunofluorescence data (IF) measuring viral replication are indicated as +(viral replication detectable) and −(no viral replication detectable due to inactivation by the indicated concentration of β-propiolactone).

Table 5 shows the determination of the titer of the HCV signal of a Pestivirus BVDV-non-CP7-HCV 5'NTR chimera culture. Positive HCV signal was obtained using real-time PCR amplification for two Pestivirus RNA chimeras (BVDV-nonCP7-HCV 5'NTR, K4 and K8) and an HCV control. K4 and K8 Pestivirus RNA chimeras both showed an early Ct high titer HCV signal, indicating successful integration of the HCV 5'NTR into BVDV.

Table 6 shows the HCV signal obtained using real-time PCR amplification for two Pestivirus RNA chimeras and an HCV control with and without reverse transcriptase (RT) Results of a reverse transcriptase (RT) based PCR demonstrated that Pestivirus RNA chimera HCV signal was derived from RNA, not DNA.

Table 7 shows the resistance of the Pestivirus chimera BVDV-non-CP7-HCV 5'NTR to ribonuclease (RNase) digestion. Ct values are shown for two Pestivirus RNA chimeras and an HCV control without RNase treatment, and when RNase was present before or after extraction.

DETAILED DESCRIPTION OF THE INVENTION

RNA viruses are prevalent human and animal pathogens. Analytical NAT assays have been developed to allow detection of RNA viruses in infected individuals. A large group of RNA viruses are the positive-strand ssRNA viruses (Baltimore Group IV), which have their viral genome directly utilized as an mRNA. Positive-strand ssRNA viruses include many families of viruses that severely impact health and function in livestock and humans, such as the common cold virus (Rhinovirus), Poliovirus, the Hepatitis A and C viruses, the Dengue and Yellow fever viruses, and the SARS virus. Currently, safe and reliable analytical assays for the detection of RNA viruses are needed, including quality control materials for these assays.

The family Flaviviridae in Group IV includes three known genera, two of which affect humans. The genus *Flavivirus* includes, for example, Yellow fever virus, West Nile virus, Dengue fever virus, St. Louis encephalitis virus, Tick-borne encephalitis virus, and Japanese encephalitis virus. The genus Hepacivirus includes the Hepatitis C viruses (HCVs). The third genus Pestivirus affects livestock, and includes Classical Swine Fever Virus (CSFV), Border Disease Virus (BDV) and Bovine Viral Diarrhea Virus (BVDV). While each Flaviviridae member has a definitive host (cell) tropism and disease specifics, each also shares a significant degree of structural relatedness for the family Flaviviridae. In particular, each such member has a similar virus morphology and high degree of conservation of the genomic organization.

Recognition of the genomic structural similarities within the Flaviviridae family has allowed the opportunity of cross-utilization of intact Flaviviridae viral genomes for research and medical diagnosis purposes. For example, BVDV has been widely accepted as a surrogate virus for HCV inactivation studies. HCV infects humans, but, so far, only certain genomic subtypes or hybrid forms of these subtypes grow well in cell culture. The genome structure of BVDV, however, is generally similar to that of HCV, and BVDV does not infect humans. The use of a genome of a surrogate virus as quality control (QC) material in analytical assays, however, is not always applicable. Quality control materials for diagnostic RNA nucleic acid tests (target or signal amplification based) are often based on purified "naked" RNA or surrogate materials like Armored RNA. It would be preferable to have a quality control material that is as similar as possible to the target analyte so that all steps of the analytical process are mimicked as closely as possible.

The genome of the members of the Flaviviridae family is a single stranded, non-segmented RNA ranging in length from about 10 kb to 16 kb. The viral RNA contains a long open reading frame (ORF) encoding at least three major viral structural proteins and at least six non-structural proteins. The ORF is flanked by 5' and 3'-nontranslated regions (5'NTR and 3'NTR) that range in length from about 100 to several hundred nucleotides (Lindenbach et al., Flaviviridae: the viruses and their Replication, in Fields virology, 5th ed., Knipe et al., eds., Lippincott, 2007, p 1101-52).

There is complexity in the functions of the Flaviviridae RNA. The viral RNA genome interacts with the host cell translation machinery to serve as a messenger RNA for the translation of viral proteins, as well as functioning as a template for viral RNA replication. Both the 5'NTR and 3'NTR are rich in defined RNA structure motifs known to be important for both the viral RNA translation and viral RNA replication functions (Lindenbach et al., see above). Along both processes, the NTRs are believed to functionally interact with each other as well as with host-cell encoded regulatory factors, such as the NFAR proteins (Isken et al., 2003; 2004; 2007). The 3'NTR of Flaviviridae is generally composed of a variable (less conserved) region (3'V) and a constant (conserved) region (3'C) (Deng and Brock, 1993). With different members of each Flaviviridae genus, the 3'C was shown to contain RNA elements that are essential for viral RNA replication while parts of the 3'V region were indicated to be dispensable for replication (reviewed by Isken and Behrens, 2006, in Molecular Biology of the Flavivirus; Horizonbioscience, p 101-134). Detailed investigations of the 3'V region of the BVDV genome revealed that 3'V, as a whole, is not dispensable for viral replication and that it acts as an important modulator of the viral translation and replication process (Isken et al., 2003; Isken et al. 2004).

The 3'NTRs of pestiviruses have a length of approximately 190-230 nucleotides and display a high degree of similarity between the different virus members. The 3'V portion of the Pestivirus 3'NTR has defined recognizable regions. Structurally, while there is sequence heterogeneity between different Pestivirus strains, the pestiviral 3'V region generally forms two thermodynamically unstable stem-loop structures, termed $SL_{stop}$ (also SLIII) and SLII. It also contains at least one copy of a 12 nucleotide consensus sequence designated as a UGA box motif (Isken et al 2003; 2004; Pankratz et al., 2005, J Virol. 79:9119-27). Further, there is conservation within the pestiviral (and all Flaviviridae) 3'V regarding the presence of so-called pseudo-stop codons. The pseudo-stop codons are nucleotide triplets in the 3'V region of the 3'NTR that resemble translational stop codons, which are present 'in frame' (following the translational triplet code) with the viral open reading frame. Mutational and structural analysis showed that the integrity of the 3'V region and the presence of UGA boxes and pseudo-stop codons are important for the binding of the NFAR host proteins and for accurate termination of translation of the viral RNA, respectively. In summary, these factors were demonstrated to represent essential determinants of the viral RNA replication process (Isken et al, 2003; Isken et al., 2004).

The structurally complex and conserved 5'NTR and 3'NTR of Flaviviridae present target regions that may be utilized for the detection of these RNA viruses in analytical assays. This is particularly true for analytical methods based on target amplification, such as polymerase chain reaction (PCR) or transcript mediated amplification (TMA). The 5' NTR of the genus *Flavivirus* has here been commonly used as a target sequence for assays like HCV (Nolte F S, Green A M, Fiebelkorn K R, Caliendo A M, Sturchio C, Grunwald A, Healy M. Clinical evaluation of two methods for genotyping hepatitis C virus based on analysis of the 5' noncoding region. J Clin Microbiol. 2003 April; 41(4):1558-64.) or West Nile virus (WNV). (Detection, Validation and Quantification of West Nile Virus RNA by the Alternative NAT WNV Assay V. Shyamala, S. Pichuantes, B. Jaitner, D. Madriaga, P. Arcangel, J. Cottrell, S. Nguyen, H. Huang, A. Medina-Selby, D. Coit, C. McCoin, D. Chien, B. Phelps. AABB Poster 2003 (http://www.chiron.com/docs/library/posters/aabb2003posters/aabb2003posters_5.pdf)

The detection of Group IV animal viruses uses known nucleic acid amplification techniques, such as polymerase chain reaction (PCR), Nucleic Acid Sequence Based Amplification (NASBA), Transcription-Mediated Amplification (TMA), other nucleic acid amplification technologies. Also signal amplification technologies like bDNA, can be used in medical research and in clinical diagnosis. Modern NAT testing allows sensitive detection of small amounts of RNA from viruses, bacteria and other cells or tissues. NAT testing usually consist of a series of sequential steps: sample preparation (purification and concentration of RNA), amplification (e.g. by PCR or TMA) and detection (e.g. by using signal generating fluorescence probes, bound free separation and detection of amplicon or gel band analysis). In the case of RNA, an additional reverse transcription step converting RNA into cDNA is required before amplification. Meaningful quality control of NAT assays requires monitoring of every step of this process. Typically, external and internal controls are used for quality control of NAT assays.

Described herein are the formation of stable virus chimeras by insertion of donor heterologous sequences into selected regions within the 3' nontranslated region (3'NTR) of the RNA genome of the Flaviviridae Pestivirus. The chimeric RNA genomes of the resulting Flaviviridae Pestivirus are sequence stable, replication competent, infectious and the genome encoded and assembled chimeric virus particles are RNase resistant.

The heterologous insert is located within the Pestivirus 3'NTR. Preferably, the insertion is downstream of the 5' UGA box within the 3' variable region (3'V) of the 3'NTR. Most preferably, the heterologous insert of the chimera is located between two stem-loop structures ($SL_{STOP}$ and SLII) within the 5'-terminal portion of the 3'NTR of the Pestivirus RNA. The 3'NTR of the Pestivirus chimera viral RNA contains pseudo stop-codons. The 3'NTR of the Pestivirus chimera viral RNA contains binding sites for the NF/NFAR proteins. The 3'NTR of the Pestivirus chimera viral RNA contains at least one UGA box motif, preferably the $UGA_{pos.cons.}$ motif.

These Pestivirus chimeras may be utilized as quality control materials in analytical RNA assays, including use as external positive controls (EC or PC), internal quality standards (IQS), internal controls (IC), internal quantification standards (QS), parallel complementary controls (PCC), calibrators, standards and in validation and verification panels. IC and QS are also referred to as IQS, since they can be the same substance. A difference between IC and QS is the way the signal generated by the substance is analyzed. The invention is useful for any detection assays including but not limited to target amplification technologies (e.g., PCR, TMA, NASBA, etc.) and signal amplification technologies (e.g., bDNA, etc.).

The same Pestivirus chimera can be used as EC, PC, calibrator or standard. This includes but is not limited to: standards traceable to an SI unit (e.g. mol), international standards, national standards (e.g. those provided by national measurement standards laboratories which establish standards for a country or organization like NIST in the USA or PTB (Physikalisch Technische Bundesantalt) in Germany) reference standards, certified reference materials, certified reference standards, JCTLM (Joint Committee for Traceability in Laboratory Medicine) approved materials, higher order reference materials and WHO standards (e.g. a WHO standard for HCV NAT assays). This substance contains target analyte sequences An RNA assay using e.g. a Pestivirus Chimera positive control and a Pestivirus Chimera QS would require two different chimeras. The inserted sequence would be different for the PC control material and QS control material.

An external control (EC), e.g. a positive control (PC), utilizes a composition that is the same or very similar to the target analyte sequence, but is assayed separately in an independent reaction from the target analyte sample. The EC or PC quality controls the same sequence as the target. In PCR, NASBA, TMA or other amplification technologies, an amplification product is formed identical or similar to the target, and the measurement signal generated is identical to the target signal. The external run control's purpose is to verify the EC test results fall within a predetermined acceptance criteria. The EC or PC are an integral part of a nucleic acid detection system (e.g. a PCR based diagnostic system) quality control and can be supplied as part of a reagent kit. See e.g. package insert for Roche COBAS AmpliPrep/COBAS TaqMan HIV-1 Test, Roche COBAS AmpliPrep/COBAS TaqMan HCV Test, ABBOTT RealTime HIV-1 test (69-6672/R1) or ABBOTT RealTime HCV test (69-6675/R1). These type of controls are, however, not necessarily part of a kit and can also be supplied as independent external run controls (e.g. OptiQual controls by AcroMetrix). Substances useful as external run control can also be used as calibrators for quantitative assays. While positive and negative controls indicate the general performance of the assay and allow a decision on reliability, calibrators help to measure the correct quantity of an analyte (e.g. the amount of HIV-1 in a patient's blood). Control and calibrator concepts for NAT assays are well known and have been described in e.g. ISO standard 17511:2003 and Section III G. of FDA's (1999) "Guidance for Industry In the Manufacture and Clinical Evaluation of In Vitro Tests to Detect Nucleic Acid Sequences of Human Immunodeficiency Viruses Types 1 and 2" and CLSI Guideline MM3-A2 Section 11.4

Internal Quality Standards like Internal Controls (IC) and internal Quantification Standards (QS) are used as follows according to the Clinical and Laboratory Standards Institute, CLSI Guideline MM3-A2, Section 7: "Inhibition of a nucleic acid test results from the presence of substances that lead to a failure to achieve a positive signal. Interference of a nucleic acid test results in a reduction in assay performance leading to a false-negative or false-positive result. Inhibitors of amplification can be detected by the use of internal control templates, also referred to as recovery templates, or simply, internal controls. The control template can be added to the sample either prior to, or after sample preparation. If it is added prior to sample preparation, it can also serve as a control for the nucleic acid extraction." Due to its resistance to RNase degradation this invention can be added prior to sample preparation and serve as a control for the nucleic acid extraction. It could be even useful as a full process control including even earlier steps than sample preparation like sample collection and sample transport. The same guideline specifies a number of different control types useful for "Detection of Inhibitors and Interfering Substances" (Section 7.1, CLSI Guideline MM3-A2). A RNA virus chimera described in this invention can be used to provide the substances useful to serve as the internal controls described in the guideline. These controls are known in the art also as "unmodified target controls" (section 7.1.1, CLSI Guideline MM3-A2), "modified target controls" (section 7.1.2) and "Heterologous Internal Controls" (section 7.1.3, CLSI Guideline MM3-A2).

Internal quality standards (IQS) like IC or QS, are assayed simultaneously in the same reaction vessel as the target analyte. A negative patient result (e.g. for HIV or HCV) is only reported as "negative" or as "target not detected" if the IC or QS result falls within an acceptable range. In case the IQS results falls outside of the acceptance range the result is considered invalid and the sample should be retested.

An internal quantification standard (QS) is a type of IQS that allows precise quantification of the target analyte even in the presence of inhibitors. Both QS and Internal control (IC) generate signals distinguishable from the target signal. In the case of PCR, the amplification product and the generated signal are different and distinguishable from the target signal. IC and QS are used to detect and compensate (QS) for inhibition. They help to distinguish between a true negative and a false negative result. QS and IC sequences are often synthetic materials since they are usually designed to be different from the target, however, they should still behave like the target analyte (e.g. a virus) and go through the entire diagnostic process from sample preparation to detection. Ideally an IQS would in addition also monitor sample collection and transport.

U.S. Pat. No. 7,183,084 B2 and U.S. Pat. No. 7,192,745 describe a specialized type of internal quality control. The parallel complementary control (PCC) has the same thermodynamic properties as the target amplicon and therefore behaves in PCR like the target nucleic acid. The parallel complementary control provides one component to ensure an IQS behaves like the target analyte, however as a piece of naked RNA it would not be resistant to degradation by RNases when added into e.g. human plasma. To fully achieve that the PCC behaves like the target analyte during sample preparation, it needs to be encapsulated in a particle that behaves like the target analyte and can be added to the patient sample without being degraded. This invention is useful to provide RNase resistant parallel complementary internal controls formulated in a patient sample like matrix.

The chimeric RNA genome of the chimeric Pestivirus is useful to provide the RNA based internal controls and quantification standards described in U.S. Pat. No. 7,192,745.

This invention can further be used as a standard for the quantification of RNA as described in U.S. Pat. No. 7,183,084 B2 and further provide an RNase resistant form of a parallel complementary QS as described in U.S. Pat. No. 7,192,745.

Quantification Standards are commonly used in commercial NAT assay kits. Two examples are the Roche COBAS AmpliPrep/COBAS TaqMan HIV-1 Test kit or Roche COBAS AmpliPrep/COBAS TaqMan HCV Test kit. The QS material is described in the Roche COBAS AmpliPrep/COBAS TaqMan HIV-1 Test (P/N: 03542998 190) package insert (May/2007 Doc Rev. 1.0) as "HIV-1 QS (HIV-1 Quantification Standard). An HCV QS is used with the Roche COBAS AmpliPrep/COBAS TaqMan HCV Test and described in the package insert.

Two different Pestivirus chimeras could be used as a RNase resistant QS (Chimera Roche-1) and a positive control and a calibrator material (Chimera Roche-2) for the Roche COBAS AmpliPrep/COBAS TaqMan HIV-1 Test. Chimera Roche-2 would contain a heterologous HIV sequence detectable by the assay. Two additional chimeras would be required for the same purpose for the Roche COBAS AmpliPrep/COBAS TaqMan HCV Test kit (Chimera Roche-3 as HCV PC and Chimera Roche-4 as HCV QS).

Internal Controls are commonly used in commercial NAT assay kits. The Pestivirus chimeras could serve as an internal control (IC) for the detection of inhibition as used in the ABBOTT RealTime HIV-1 test kit (69-6672/R1) or ABBOTT RealTime HCV test kit (69-6675/R1). The Abbott Internal Controls are described in the package insert under "Reagents" List No. 2G31Y for the HIV-1 test and List No. 4J86Y for the HCV test. The IC target sequence for both tests was derived from the hydroxypyruvate reductase gene from Cucurbita pepo and delivered as an Armored RNA particle in negative human plasma. A Pestivirus RNA chimera could be used to provide the same sequence from the hydroxypyruvate reductase gene from Cucurbita pepo. A Pestivirus RNA chimera based internal control would mimic the target analyte better than Armored RNA, because it resembles HIV and HCV more than the MS2 bacteriophage.

A Pestivirus chimera could be used as a RNase resistant IC (Chimera Abbott-1) and a separate Pestivirus-HIV Chimera could be provided to serve as low and high positive control in the Abbott RealTime HIV-1 Control Kit (List No. 2G31-80) (Chimera Abbott-2). Chimera Abbott-2 could also be used as calibrator material in the Abbott realTime HIV-1 Calibrator Kit (List No. 2G31-70). One additional Pestivirus-HCV chimera (Chimera Abbott-3) would be required for controls and calibrators of the ABBOTT RealTime HCV test. Unlike the Roche TaqMan assays, which use separate Quantification Standards sequences for their HIV and HCV assay, the Abbott realTime PCR assays, use a common IC sequence for their HIV-1 and HCV assays.

The Pestivirus chimeras can be used as IC, QS, positive control and calibrator in commercial RNA NAT assays. For example, the chimeric RNA genome of the chimeric Pestivirus can be used as Positive control and calibrator in commercial RNA NAT assays. A second chimera would be required to serve as IC or QS. These controls can be packaged together or separate from the other required reagents. The materials can be lot specific or lot independent.

Figure 1A:
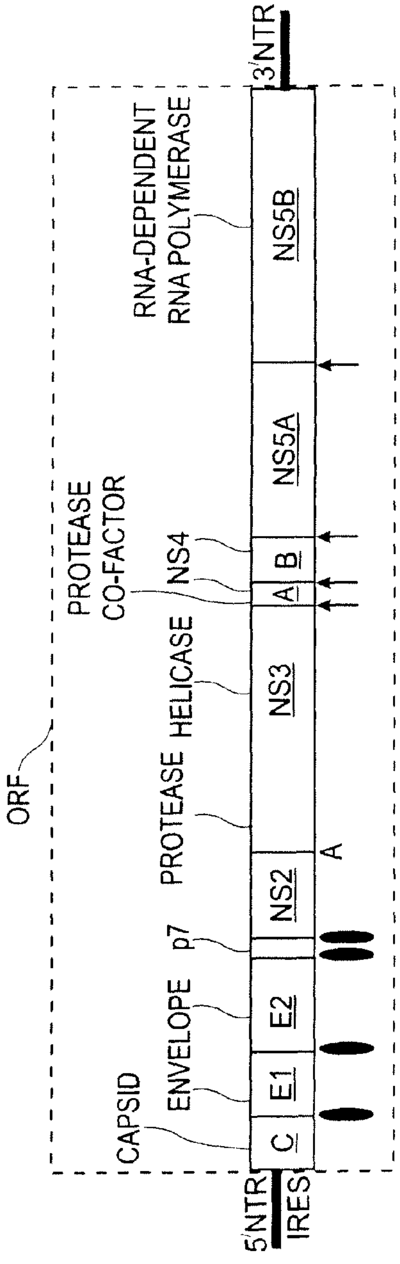
Figure 1B:
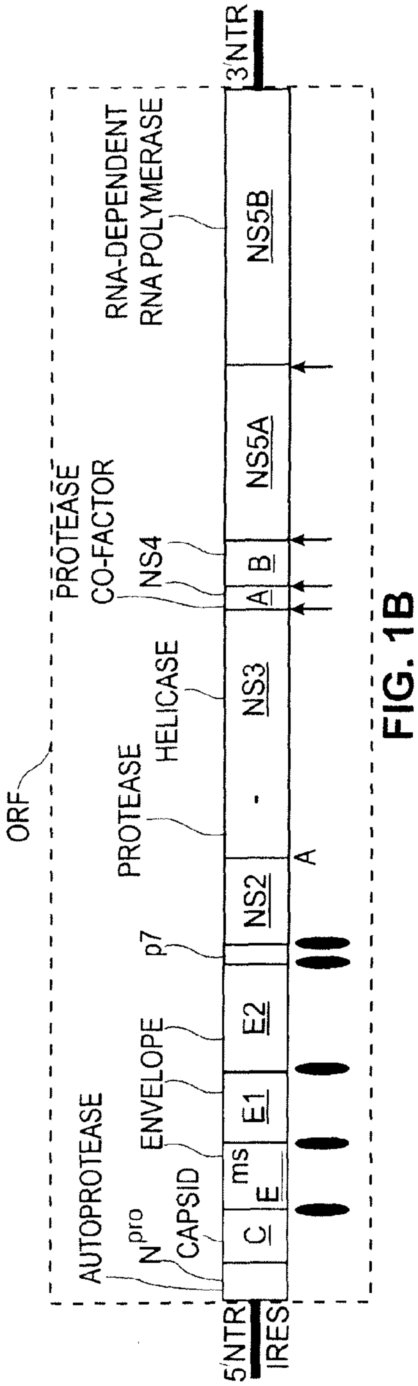

FIG. 1 shows a schematic alignment of the genomes of the Pestivirus BVDV virus and the Hepacivirus HCV virus. BVDV and HCV display a similar genomic organization. Both viral RNAs contain a long open reading frame (ORF; indicated as box) that is flanked by nontranslated regions (NTRs) at the 5' and 3' ends (single lines). The BVDV and HCV 5'NTRs contain internal ribosomal entry sites (IRES) that mediate translation of a viral polyprotein. Inspection of FIG. 1 shows that both viral RNAs encode a similar polyprotein (C, E1, E2, p'7, NS2, NS3, NS4A, NS4B, NS5A, NS5B-COOH) that is co- and post-translationally processed by cellular and viral proteases to give rise to structural (C, E1, E2, p'7) and nonstructural (NS2-NS5B) viral proteins (Lindenbach et al., 2007). The BVDV genome contains an additional nonstructural protein, the autoprotease $N^{PRO}$ and an additional envelope protein, $E^{RNS}$. The BVDV genome has a length of approximately 13 kb, while the HCV genome has a genome size of ca. 10 kb.

Figure 2:
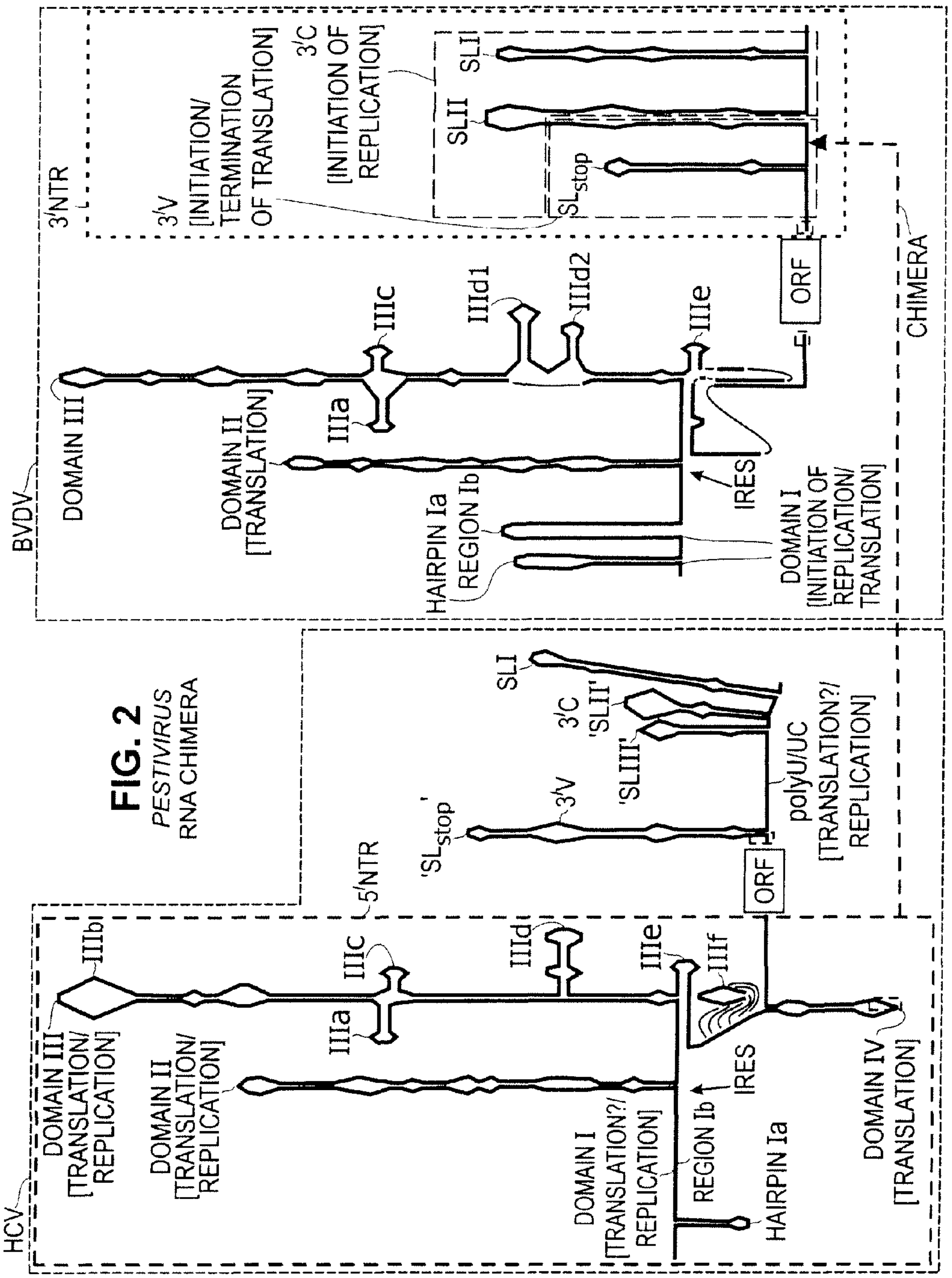

FIG. 2 shows in diagram form the strategy for the insertion of a heterologous sequence (HCV 5'NTR, amplicon) within the 3'NTR of the Pestivirus BVDV. FIG. 2 shows the insertion within the 3'NTR into a region between the two stem-loop structures $SL_{STOOP}$ and SLII. This region was rather tolerant to the insertion of a variable sequence. However, the HCV 5'NTR should not be able to re-initiate translation as this would interfere with the initiation of replication at the immediate 3'end. For that purpose, sequence elements in the BVDV 3'NTR that ensure immediate translation termination are left intact (Isken et al., 2004) The 5'NTR region of the HCV is circled in FIG. 2, and an arrow indicates the insertion of this sequence within the 3'NTR of Pestivirus BVDV. The structure of the stem-loops found in the 5'NTR and the 3'NTR of the HCV and the BVDV viruses is indicated. The known functions of the different regions of the viral NTRs during translation and RNA replication are indicated (Grassmann et al., 2005). The open reading frame (ORF) is shown as a box.

Figure 3:
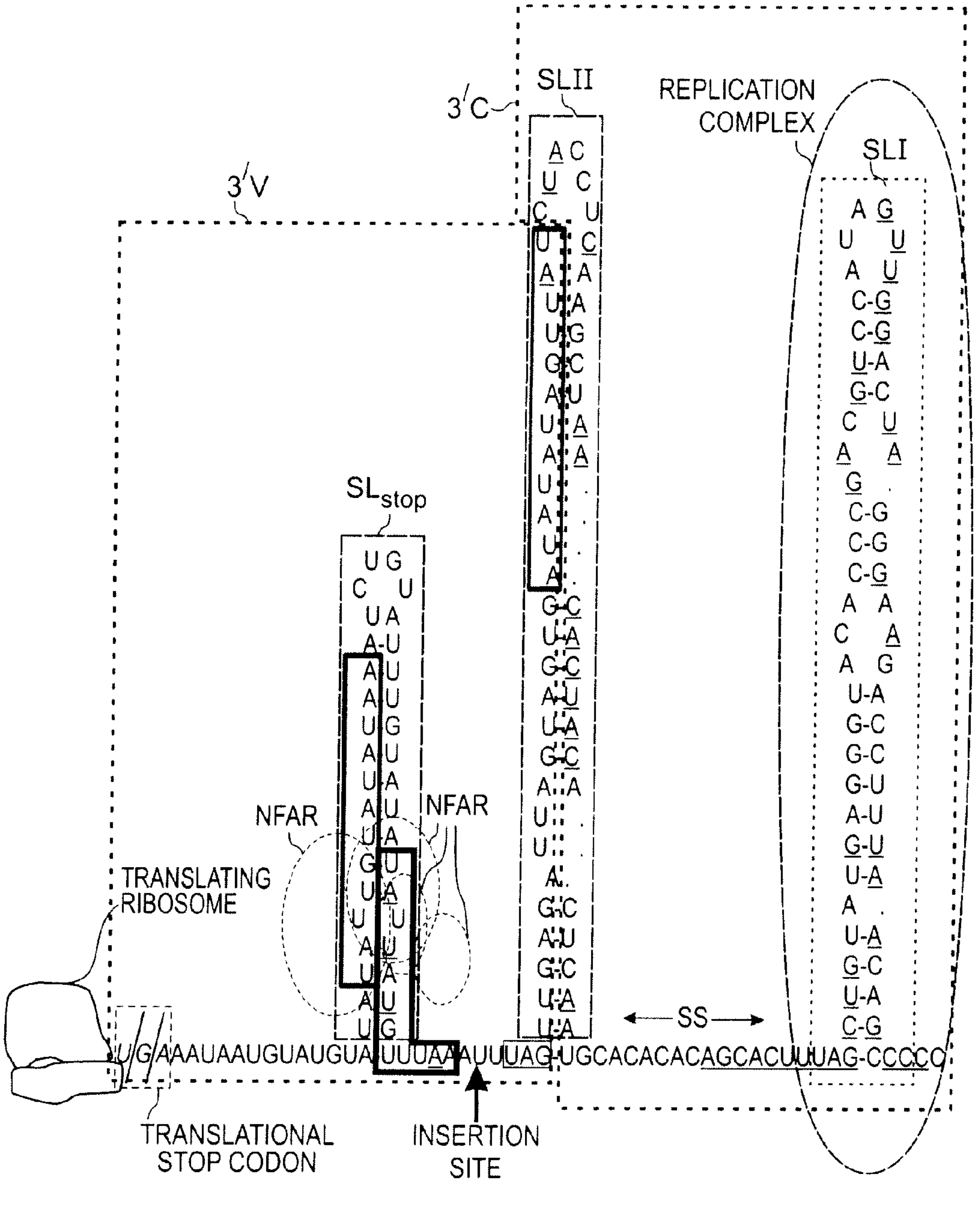

FIG. 3 shows a diagrammatic model of the structure and functions of the Pestivirus BVDV 3'NTR (Yu, et al., 1999; Isken et al., 2004). A representative sequence of the 3'NTR from BVDV (BVDV replicon D19c, which is highly homologous to the 3'NTR of BVDV non-CP7; Behrens et al., J. Virol., 1998) is shown. The variable region (3'V) is involved in the coordination of translation and RNA replication by efficiently terminating translation. For this activity, binding of NFAR proteins to the 3'V region involving the UGA boxes is needed. The 3' variable region (3'V) and the 3' constant region (3'C) are each shown boxed with dashed lines. The 3'V represents the sequence following the translational stop codon (shown boxed; a stopping ribosome is schematized by a double structure); the border between the 3'V and the following 3'C region is indicated by juxtaposition of the dashed line boxes near the top of SLII. The constant region (3'C) is shown as the remainder of the 3'NTR. The 3'C is the region where the replication complex assembles, which is indicated by a large oval. The functional interactions of the 3'NTR are indicated diagrammatically for: the translating ribosome (double structure), the NFAR proteins (collection of circles), and the replication complex (large oval). SS indicates a highly conserved intervening region located between SLII and SLI. The large arrow indicates an insertion site for the heterologous RNA sequence for the formation of a stable and functional Pestivirus RNA chimera.

Figure 4:
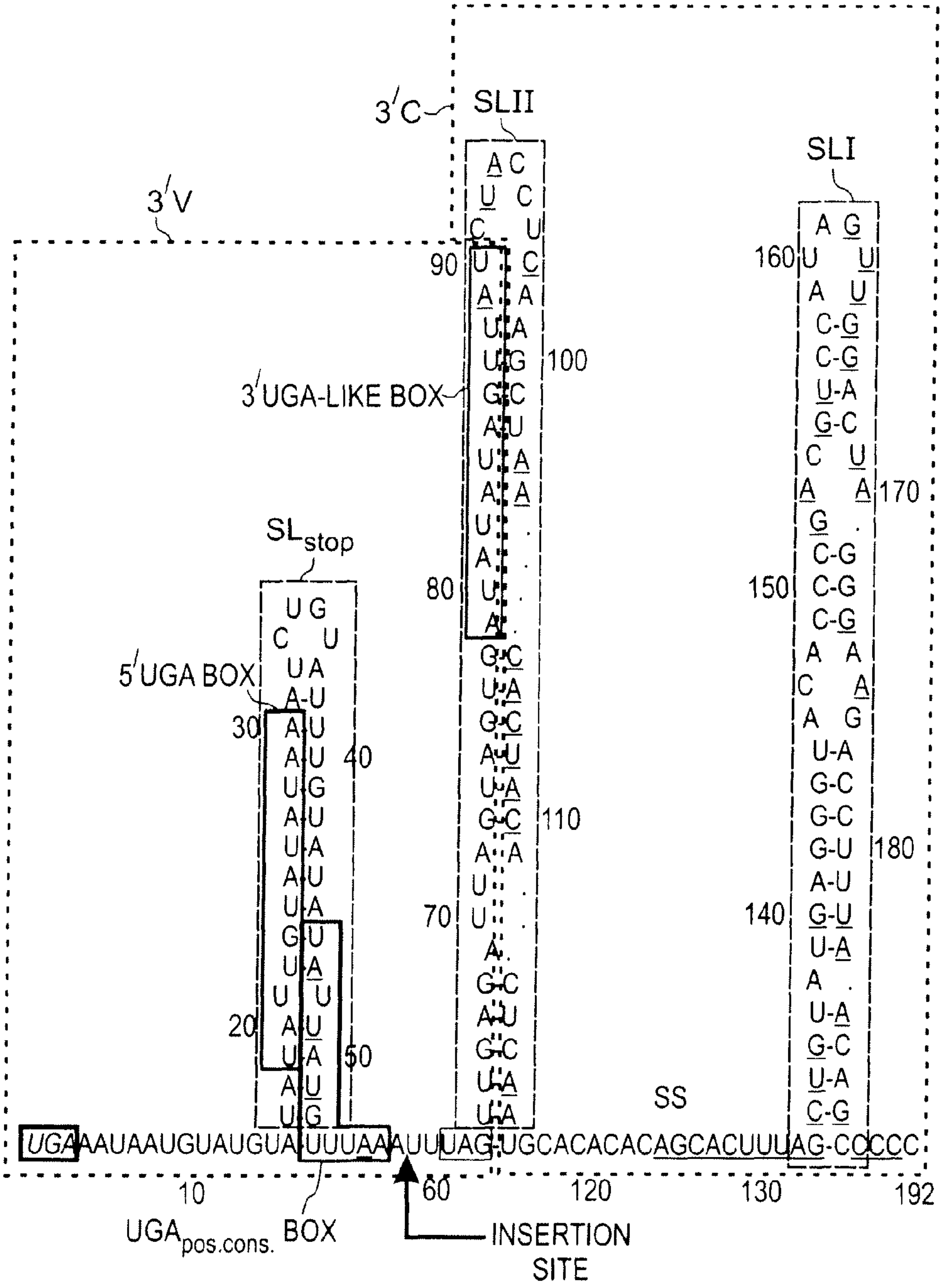

FIG. 4 discloses a more detailed diagram of the 3'NTR sequence of Pestivirus BVDV-D19c, which is highly homologous to the 3'NTR of BVDV non-CP7 showing the 3'V and the 3'C regions. As in FIG. 3, the 3'V and the 3'C regions are indicated with dashed-line boxes. The 3'V region contains the $SL_{STOP}$ (SLIII) stem-loop and a portion of the SLII stem-loop, which ends after the end of the 3'UGA-like box and is marked by a juxtaposition of the dashed line boxes (at nucleotide 90; Deng and Brock, 1993). In FIG. 4, the 3'V region contained UGA box motifs, including: the 5'UGA box (nucleotides 19-30), the $UGA_{pos.cons.}$ box (nucleotides 46-57) and the 3'UGA-like box (nucleotides 79-90). As in FIG. 3, the large arrow indicates a preferred insertion site immediately following the $SL_{STOP}$ (SLIII) where a heterologous RNA sequence may be inserted for the formation of a stable and functional Pestivirus RNA chimera.

Referring to FIG. 4, separate structures within the 3'NTR of BVDV are identified. Downstream (3' direction) of the UGA stop codon is a discrete sequence of approximately 12 nucleotides that separates the stop codon from the beginning of the $SL_{STOP}$ stem loop structure. Minor variations in the length of this discrete sequence are possible (See FIG. 5A).

An insertion site is located within or downstream (3' direction) of the beginning of the 5' UGA box. Preferably, the insertion site is downstream of the 5' UGA box and upstream (5' direction) of the 3' UGA-like box in the SLII stem-loop. More preferably, the insertion site is between the $SL_{STOP}$ and the SL II stem-loops, or between the $UGA_{pos.cons.}$ box and the beginning (the most 5' aspect) of the SLII stem-loop. Most preferably, the insertion site is before, within or immediately after the AUU codon located 3' of the $UGA_{pos.cons.}$ box and before the UAG codon at the beginning of the SLII stem-loop. As shown by the arrow in FIG. 4, an insertion site described in the Examples below was between the first and second nucleotide position of the AUU codon, or between the AAA and UUU sequences between the $SL_{STOP}$ and SLII stem-loops, respectively.

Accordingly, the insertion site is also downstream of the beginning of the 5' UGA box, downstream of the end of the 5'

UGA box, and preferably downstream of the 5' of the end $UGA_{pos.cons.}$ box, the insertion site is also defined as within the 3' NTR, within the 3' constant region, or upstream of the 3' or 5' end of the 3' UGA-like box.

FIG. 5A shows an alignment of the 3'NTR for various strains of Pestivirus. On the left is an alignment of the 3'NTRs of different Pestivirus strains (Becher et al. J. Virol. 1998 72: 5165-5173). The sequences forming $SL_{STOP}$ (SLIII) and SLII are indicated. With all of the different Pestivirus strains, the predictions of the structural similarity of SLII and SLstop (SLIII) are analogous. The boxed area indicates the position of the $UGA_{pos.cons.}$ box, which is located within the 3'V region and contains four nucleotides that are 100% conserved between all known Pestivirus strains (marked by asterisks). A thick arrow indicates the proposed border of the 3'V and 3'C regions of the 3'NTR of all these Pestivirus strains (Deng and Brock, 1993). The $UGA_{pos.cons.}$ box has been found to be present at nearly identical positions in all pestiviral genomes, i.e. about 39-42 residues downstream of the ORF (Isken, 2003). The arrow indicates a preferred site where the heterologous insert was introduced into BVDV-non-CP7. FIG. 5B details the consensus sequence and conserved positions of the UGA box sequences of different Pestivirus strains (Isken et al., 2003). Given the analogous structural similarity of the stem-loop structures within the 3'V and the consensus of sequences within the $UGA_{pos.cons.}$ box, the 3'NTR, therefore, may be commonly used for insertion of a heterologous sequence with all Pestivirus. The site immediately following the $UGA_{pos.cons}$. box is an example of a preferred site for all Pestivirus strains for insertion of a heterologous RNA sequence. The procedure described for the construction of a 3'NTR viral chimera can be used with all Pestivirus to create functional chimeric viruses that may be, for example, used as standards and controls for analytical assays.

EXAMPLE 1

Construction of BVDV-non-CP7 cDNA and Generation of Infectious Non-Cytopathic Viral RNA A modified cDNA of BVDV (type-1) strain CP7 was generated as a starting material for all subsequent procedures (Becher et al., 2000 J. Virol. 74: 7884-7894). The modification was performed such that the CP7 insert (Tautz et al., J Virol. 1996 November; 70(11):7851-8) was removed to create a cDNA containing plasmid that encoded a BVDV "non-CP7" RNA biotype (M. Behrens, unpublished data). A similar construct was published earlier by Makoschey et al., (Vaccine, 2004, Sep. 3; 22(25-26):3285-94.) The complete sequence of the cDNA for the BVDV-non-CP7 is given as SEQ ID NO: 1.

The plasmid encoding the BVDV-non-CP7 cDNA was linearized by restriction digestion with the restriction endonuclease SmaI. In vitro transcripts were generated by run-off transcription using SP6 RNA polymerase. The viral RNA was generated by in vitro transcription using SP6 RNA polymerase. The in vitro generated BVDV-non-CP7 RNAs were transfected into Marbin Darby Bovine Kidney (MDBK) cells using standard protocols. Three (3) days post transfection, the cell culture supernatant was collected and used to either titrate the contained infectious virus particles or to re-infect other MDBK cells. Three days after re-infection, virus titers were determined and the cells examined for a cytopathic effect using standard procedures (Tautz et al., J. Virology, 1996, 70 (11):7851-8). Thus, the non-cytopathic nature of the generated virus was confirmed. The titrations revealed that $5\times10^6$ to $5\times10^7$ infectious virus particles were detectable per ml of cell culture supernatant (see also Table 1 and Table 2, data for BVDV-non-CP7).

EXAMPLE 2

Generation of Chimeric BVDV-non-CP7 cDNAs

The plasmid including the BVDV-non-CP7 cDNA (SEQ ID NO: 1) was then used to introduce the HCV 5'NTR sequence (HCV Con1 cDNA; Lohmann et al., 1999) within the BVDV 3'NTR to obtain a functional chimeric viral sequence (BVDV-non-CP7-HCV 5'NTR).

For that purpose, a synthetic DNA fragment was generated commercially. This DNA fragment corresponded to the ClaI (initiating at pos. 11047 of the BVDV-non-CP7 cDNA sequence)/SmaI (initiating at pos.12264 of BVDV-non-CP7 cDNA sequence) fragment of the BVDV-non-CP7 cDNA (SEQ ID NO:1), but also included an HCV 5'NTR insert (Con 1 subtype 1b isolate; Lohmann et al., 1999, Science. July 2: 285 (5424): 110-3) flanked by two restriction sites (SnaBI and PacI) and an additional TAA trinucleotide. The cDNA sequence of the HCV 5'NTR is given in SEQ ID NO: 2. This heterologous insert was positioned such that in corresponding RNA transcripts it was located between the $UGA_{pos.cons.}$ box and the SLIT stem-loop structure in the 3'V of the BVDV non-CP7 3'NTR (see FIGS. 3 and 4 for diagram of a preferred insertion site).

Using standard recombinant cloning techniques, the respective ClaI/SmaI fragment was cloned into the BVDV-non-CP7 cDNA (SEQ ID NO:1) containing plasmid that was cut with the same restriction sites. Performing several independent ligations and screening of several hundred clones yielded recombinant plasmids encoding the chimeric cDNA. The resultant chimeric cDNA clone was termed BVDV-non-CP7-HCV 5'NTR cDNA (SEQ ID NO: 3). It thus encoded a heterologous sequence at position 12134, i.e., essentially two novel restriction sites and the HCV 5'NTR (SEQ ID NO: 2) placed within the sequence encoding the BVDV 3'NTR to yield the BVDV-non-CP7-HCV 5'NTR chimera (SEQ ID NO: 3, FIG. 6). Note that the introduced HCV 5'NTR sequence was modified at two single nucleotide positions to remove internal SmaI sites (c→t at position 12269 and c→t at pos. 12456 of the BVDV-non-CP7-HCV 5' NTR cDNA). These nucleotide exchanges were necessary to allow linearization of the BVDV-non-CP7-HCV 5' NTR cDNA encoding plasmid by SmaI for run off transcription by SP6 RNA polymerase to generate viral RNA molecules that ended with the correct 3' terminus. FIG. 6 shows the cDNA sequence of the BVDV-non-CP7-HCV 5'NTR chimera with the restriction endonuclease sites indicated for ClaI, part of SmaI, SnaBI and PacI. The nucleotide exchanges (c changed into t) are also indicated.

Applying the same strategy, an insert encoding two restriction sites, SnaBI and PacI) was introduced into the BVDV-non-CP7 cDNA containing plasmid (SEQ ID NO: 1) at the same position (insertion at position 12134). This construct was termed BVDV-non-CP7+ cloning site, and the cDNA sequence is given in SEQ ID NO: 4. FIG. 7 shows the cDNA sequence of the BVDV-non-CP7+ cloning site chimera with the restriction endonuclease sites indicated for ClaI, part of SmaI, for SnaBI and PacI.

The correctness of the respective inserts was verified by restriction analysis of the cDNA encoding plasmids and sequencing as shown in FIG. 8. FIG. 8 shows sequence details of the 3'NTR region for the construction of the Pestivirus chimera sequences (given as DNA sequence). FIG. 8 (A+B)

shows a comparison of the cDNA sequences of the 3'NTR of the BVDV-non-CP7+ cloning site chimera and the sequence of the 3'NTR of BVDV-non-CP7.) FIG. 8 (A+C) shows a comparison of the sequence of the 3' NTR of the BVDV-non-CP7-HCV5'NTR chimera and the sequence of the 3'NTR of BVDV-non-CP7.

In FIG. 8, the translational stop-codon (tga) at the end of the open reading frame (ORF) is boxed, and pseudo-stop codons are underlined. Additional and specifically changed sequences (taa) are shown in italics. The SnaBI restriction site (tacgta) and the PacI restriction site (ttaattaa) are shown in brackets. The 5'UGA box (tattgtatataa) (SEQ ID NO: 32) and the UGApos.cons. box (tattatgtttaa) (SEQ ID NO: 33) are indicated by the small dashed-line boxes. FIG. 8A shows the 3' NTR of BVDV-non-CP7 (SEQ ID NO: 5), which corresponds to that for the wild type starting material. (As noted above, the complete sequence of the BVDV-non-CP7 is given as SEQ ID NO: 1). FIG. 8B shows the 3' NTR of the BVDV-non-CP7+ cloning site chimera, which has the SnaBI/PacI restriction endonuclease cloning site insert (SEQ ID NO: 6). (As noted above, the complete sequence of the BVDV-non-CP7+ cloning site is given in SEQ ID NO: 4, FIG. 7.) FIG. 8C shows the sequence of the 3'NTR region for the BVDV-non-CP7-HCV 5'NTR chimera (SEQ ID NO: 7). The sequence of the HCV 5'NTR insert (SEQ ID NO. 2) is indicated by the large, dashed-line box. (As noted above, the complete sequence of the BVDV-non-CP7-HCV-5'NTR chimera is given as SEQ ID NO: 3, FIG. 6.)

EXAMPLE 3

Stability of the cDNA Plasmid Constructs of the Newly-Generated Pestivirus BVDV Chimeras Several individually isolated cDNA plasmids encoding either BVDV-non-CP7 (:: 1), the BVDV-non-CP7+ cloning site chimera (SEQ ID NO: 4), or the BVDV-non-CP7-HCV 5'NTR chimera (SEQ ID NO: 3) were grown in *E. coli*. The plasmids were prepared using standard procedures and the authenticity of the inserts was verified by DNA sequencing. The overall stabilities of the plasmids through several passages in *E. coli* were verified by performing restriction analysis using multiple restriction enzymes and sequencing.

EXAMPLE 4

The Pestivirus BVDV Chimeric RNAs are Replication Competent and Generate Infectious Virus Particles at Similar Titers as the Original BVDV-non-CP7 RNA The plasmids encoding the chimeric cDNAs were linearized with the restriction endonuclease SmaI. In vitro transcription was performed with SP6 RNA polymerase using standard protocols. The viral RNA then was transfected into Marbin Darby bovine kidney cells (MDBK) using standard procedures. Three (3) days post transfection, the virus titer contained in the cell culture supernatant was measured by a standard titration protocol. The transfection supernatant was then used to re-infect cells and to re-harvest and re-titrate virus at 3 day intervals. As shown in Table 1, the virus titers obtained after the initial transfection and re-infection were found to be similar with experiments that were performed with the RNAs of BVDV-non-CP7 and two BVDV-non-CP7+ cloning site chimeras (K17 and K25), respectively.

TABLE 1

Virus titers for BVDV-non-CP7 and BVDV-non-CP7 + cloning site chimera after transfection and 1st re-infection.

| | BVDV-non-CP7 | BVDV-non-CP7 + cloning site chimera, K17 | BVDV-non-CP7 + cloning site chimera, K25 | Days post infection |
|---|---|---|---|---|
| Titer (/ml) | 6.30E+05 | 9.40E+06 | 1.30E+06 | 3 (1st re-infection) |

As shown in Table 2 (line 1) similar virus titers to those found in Table 1 were also obtained with transfection and first re-infection experiments when the BVDV-non-CP7 and the BVDV-non-CP7-HCV 5'NTR chimera were tested, respectively. As also shown in Table 2, similar virus titers were found throughout subsequent re-infection experiments (up to 7 re-infection passages) for the BVDV-non-CP7 and the BVDV-non-CP7-HCV 5'NTR chimera, respectively

TABLE 2

Virus titers at various times post-infection for BVDV-non-CP7 and BVDV-non-CP7-HCV 5'NTR chimera Titer (/ml)

| BVDV-non-CP7 | BVDV-nonCP7-HCV 5'NTR chimera | Days post trasfection | Days post infection |
|---|---|---|---|
| 1.20E+06 | 5.10E+06 | 3 | |
| 2.10E+07 | 1.30E+07 | | 3 (1st re-infection) |
| 2.20E+05 | 4.90E+05 | | 3 (2nd re-infection) |
| 1.70E+06 | 6.10E+06 | | 3 (3rd re-infection) |
| 4.30E+06 | 3.20E+07 | | 3 (4th re-infection) |
| 7.40E+07 | 9.30E+07 | | 3 (7th re-infection) [1] |

[1] Titrations of 5th and 6th re-infections were not performed

To test for viral protein synthesis, cells that were infected with virus (see above) were investigated by immunofluorescence (IF) to detect newly synthesized NS3 protein. IF-detectable synthesis of NS3 protein unambiguously indicated RNA replication. Protein synthesis that occurred by translation of the viral RNA within the cell was not detectable. In other words, only if the RNA amplified would sufficient protein be synthesized and thus become detectable by IF testing (Behrens et al., 1998; J Virol. 1998 March; 72(3):2364-72). We detected NS3 synthesis with both chimeras (BVDV-nonCP7+ cloning site and BVDV-nonCP7-HCV 5'NTR), as well as with the BVDV-non-CP7 throughout all of the performed transfection/infection experiments that are shown in Tables 1 and 2. In sum, these results showed that following transfection of the RNAs into host cells, the Pestivirus chimeras BVDV-non-CP7+ cloning sites and BVDV-non-CP7-HCV 5'NTR showed identical rates of viral protein synthesis and of infectious viral particle formation.

EXAMPLE 5

Growth of BVDV-non-CP7 and the BVDV-non-CP7-HCV 5'NTR Chimera

The growth characteristics of the BVDV-non-CP7-HCV 5'NTR chimera was compared with that of the BVDV-non-CP7. As shown in FIGS. 9 and 10, the growth behavior of the newly generated BVDV-non-CP7-HCV 5'NTR chimera (measured by one-step growth curves over a 72 hour time period) was indistinguishable from that obtained for the BVDV-non-CP7. The data for FIGS. 9 and 10 is given in Table 3.

TABLE 3

Growth curve data for BVDV-non-CP7 and BVDV-non-CP7-HCV 5'NTR chimera (see FIGS. 9 and 10)

| | Titer/ml | |
|---|---|---|
| TIME (hr) | BVDV-non-CP7 | BVDV-non-CP7-HCV 5'NTR chimera |
| 12 | 7.50E+02 | 4.50E+02 |
| 18 | 3.70E+03 | 2.50E+03 |
| 24 | 1.90E+04 | 1.90E+04 |
| 36 | 2.30E+06 | 2.20E+06 |
| 48 | 3.00E+08 | 4.00E+08 |
| 72 | 4.00E+08 | 5.00E+08 |

EXAMPLE 6

Long Term Stability of the Pestivirus BVDV-non-CP7-HCV 5'NTR Chimera (7 Passages)

The Pestivirus BVDV-non-CP7-HCV 5' NTR chimera was passaged (performing subsequent re-infection experiments) for up to seven times (several weeks), without loss of titer (see Table 2; see Example 4). As shown in Table 2, measuring the virus titers after seven passages revealed no significant differences in the titer of the BVDV-non-CP7-HCV 5'NTR chimera with respect to the titer of BVDV-non-CP7 (commonly, average titers of $5\times10^7$/ml cell culture supernatant were measured). These findings allowed stable manufacturing of larger amounts (>1 liter) of virus in culture.

To determine the stability of the genomic sequence of the BVDV non-CP7-HCV 5'NTR chimera, after three passages as well as after seven passages, total viral RNA was isolated from the infected cells (using a standard procedure; Behrens et al., 1998; J Virol. 1998 March; 72(3):2364-72.) and the BVDV 3'NTR amplified by RT-PCR. After cloning of the PCR fragments (cloning site BamHI, XbaI), five different clones were sequenced. The clones generated from the $3^{rd}$ passage showed no nucleotide exchanges (data not shown). The clones generated from the $7^{th}$ passage showed very few changes: Two of five clones that were obtained after the $7^{th}$ passage displayed one nucleotide exchange within the HCV insert, while two clones showed mutations within the genomic BVDV sequence, and one clone showed no changes. FIG. 11 shows the sequence details for these five clones obtained after the $7^{th}$ passage: clone 1 (FIG. 11A) (SEQ ID NO: 8) had a g -t exchange in the HCV insert; clone 2 (FIG. 11B) (SEQ ID NO: 9) had a c-t exchange in the HCV insert; clone 3 (FIG. 11C) (SEQ ID NO: 10) had a t-c exchange in the BVDV sequence; clone 4 (FIG. 11D) (SEQ ID NO: 11) had no sequence changes, and clone 5 (FIG. 11E) (SEQ ID NO: 12) had g deleted in the BVDV sequence. The HCV insert in the BVDV non-CP7-HCV 5'NTR chimera, therefore, had approximately the same stability as the surrounding genomic BVDV sequence.

EXAMPLE 7

Inactivation of the Pestivirus BVDV Chimera with β-propiolactone

Inactivation experiments of the BVDV-non-CP7-HCV 5'NTR virus particles were performed. The culture supernatant of BVDV-non-CP7-HCV 5'NTR infected MDBK cells (7th re-infection, virus titer approximately $1\times10^8$ per ml) was incubated with various concentrations of β-propiolactone for various times at three different temperatures (4° C., 25° C. and 37° C.) as indicated in Table 4. The β-propiolactone is a protein-modifying agent known to react with amides of the $NH_3$ group of lysine or arginine. Following incubation, the culture supernatants were titrated and tested by immunofluoresence (IF, see Example 4) to detect viral RNA replication, and thus detection of infectious virus for the cultured cells. The data obtained are shown in Table 4. When infectious virus was detectable throughout several titrations (12×1:5 steps), it was scored as (+)-IF. When no infectious virus was detectable throughout several titrations (12×1:5 steps), it was scored (−)-IF. As shown below, when the culture supernatant was incubated at 0.03% β-propiolactone at 37° C. for 120 min, the Pestivirus chimeric virus was inactivated, while there was no toxicity for the cultured cells.

TABLE 4

Determination of inactivation of Pestivirus BVDV-non-CP7-HCV 5'NTR chimera.

| | | β-propiolactone Concentration | | | | |
|---|---|---|---|---|---|---|
| TIME | ° C. | 0.01% | 0.03% | 0.05% | 0.1% | 0.3% |
| 60 min | 4° C. | IF+ | IF+ | IF+ | nd | nd |
| 120 min | 4° C. | IF+ | IF+ | IF-[2] | nd | nd |
| 240 min | 4° C. | IF+ | IF-[1] | IF-[2] | nd | nd |
| 15 min | 25° C. | IF+ | IF-[1] | IF-[1] | nd | nd |
| 30 min | 25° C. | IF+ | IF-[1] | IF-[1] | nd | nd |
| 60 min | 25° C. | nd | nd | nd | IF-[2] | IF-[3] |
| 120 min | 25° C. | IF+ | IF-[1] | IF-[1] | nd | nd |
| 180 min | 25° C. | IF+ | IF-[1] | IF-[1] | nd | nd |
| 15 min | 37° C. | IF+ | IF-[1] | IF-[1] | nd | nd |
| 30 min | 37° C. | IF+ | IF-[1] | IF-[1] | nd | nd |
| 120 min | 37° C. | IF+ | **IF-** | IF-[1] | nd | nd |

Legend:
[1]Initial dilution toxic for cells;
[2]Initial dilution and 1:5 dilution toxic for cells;
[3]Initial dilution, 1:5 dilution, and 1:25 dilution toxic for cells. In bold, optimal inactivation condition.

EXAMPLE 8

Testing of HCV-BVDV Chimera for Positive HCV Signal in Real-Time PCR and Estimation of Titer Two DNA plasmid BVDV chimera clones (K4 and K8) expected to contain the HCV 5'NTR sequence were transcribed into full length viral RNA. MDBK cells were transfected with viral RNA and cultured. The cells produced infectious viral particles, which were subsequently harvested and tested for containing the expected HCV 5'NTR RNA sequence (see Example 3).

Viral RNA was extracted from clone K4 and K8 supernatant, as well as a HCV control, using the QIAamp Virus MinElute Kit (QIAGEN). Reverse transcription real time PCR was performed using the Roche TaqMan HCV ASR. K4 and K8 BVDV-HCV chimeras showed high titer HCV signals indicating successful integration of the 5'NTR into BVDV (Table 5). Based on the observed Ct values it was estimated both chimeras produced a signal equivalent to about 300 million HCV IU/mL. One IU has previously been estimated to be roughly equivalent to 2.63 viral particles. The estimated titer of 7.8E+08 virus particles/mL is higher than the observed 9.30E+07 infectious particles/mL (Table 2) because only about one in 10 viral particles is infectious. HCV patient samples rarely exceed 10 million IU/mL.

It should be noted that International Units (IU) are a different unit of measure than the previously mentioned “infectious particles” in Table 2. The HCV control showed the expected value.

TABLE 5

Estimation of BVDV-non-CP-7-HCV 5'NTR chimera titer using the Roche HCV ASR

| Samples | Ct | QS Ct | Dilution Factor | log IU/ml | Final Conc IU/ml |
|---|---|---|---|---|---|
| HCV-BVDV K8 | 20.3 | 31.4 | 10 | 7.46 | 2.9.E+08 |
| HCV-BVDV K4 | 20.2 | 31.4 | 10 | 7.49 | 3.1.E+08 |
| HCV control | 26.6 | 31.3 | 1 | 5.30 | 2.0.E+05 |

EXAMPLE 9

The HCV signal for BVDV-nonCP7-HCV 5'NTR chimera was from RNA

We tested whether the positive HCV signal in Example 6 was generated from RNA or an unlikely DNA contamination from the cDNA plasmid encoding the BVDV-non-CP7-HCV 5'NTR chimera RNA. The BVDV-nonCP7-HCV 5'NTR K4 and K8 chimera samples were extracted using a QIAamp Virus MinElute Kit (QIAGEN). PCR amplifications were performed using two separate preparations of the TaqMan One-Step RT-PCR Master Mix Reagents (ABI) and a reverse transcription PCR was performed using an HCV PCR assay based on real time detection. One master mix was prepared with no reverse transcriptase (RT), while the other master mix contained the reverse transcriptase enzyme. The RT enzyme is required for converting RNA into cDNA, which can be used during PCR by a thermostable DNA polymerase as substrate for amplification. RNA is no substrate for the DNA polymerase. Without the RT, it was expected if RNA were the source of the HCV signal, no DNA template would be made, and thus no amplification by DNA polymerase could occur. However without RT, if DNA were the source of the HCV signal, it would serve as the template for DNA polymerase and a HCV signal would be generated.

BVDV-non-CP7-HCV 5 NTR chimera samples were prepared with both master mixes, and run on the same 96-well plate on the ABI 7300. As shown in Table 6, the BVDV-non-CP7-HCV 5 NTR chimera samples and HCV samples only amplified when the reverse transcriptase (RT) was present. This allowed the conclusion that the BVDV-non-CP7-HCV 5 NTR chimera samples contain RNA, not DNA. Also, the HCV control signal originated as expected from RNA.

TABLE 6

BVDV-non-CP7-HCV 5'NTR chimera signal is derived from RNA

| sample | Ct with RT | Ct without RT |
|---|---|---|
| BVDV-non-CP7-HCV-5'NTR chimera, K8 | 26.5 | no signal |
| BVDV-non-CP7-HCV-5'NTR chimera, K4 | 26.7 | no signal |
| HCV control | 33.1 | no signal |

EXAMPLE 10

The BVDV-non-CP7-HCV 5'NTR Chimera is RNase Resistant

We tested to determine whether the BVDV-non-CP7-HCV 5'NTR chimera RNA was resistant to RNase degradation because its RNA was protected within an intact virion, or if it existed as non-encapsulated, free RNA vulnerable to enzymatic digestion with RNase.

The two BVDV-non-CP7-HCV 5'NTR chimeras K4 and K8 and an HCV control were tested under two conditions. In one experiment, an RNase digest was done prior to extraction (QIAamp Virus MinElute Kit (QIAGEN)). Loss of signal in PCR amplification would indicate free, unprotected RNA. In a second control condition, no RNase was added to the HCV-BVDV chimera samples before extraction. If the chimeric RNA was non-encapsulated, the RNase digest would degrade the free RNA. This degradation would either eliminate the HCV signal completely, or shift the Ct to a significantly higher value.

As shown in Table 7, the Ct values for the BVDV-non-CP7-HCV 5 NTR chimeras K4 and K8 did not significantly change after RNase treatment, indicating the RNA is encapsulated, and therefore protected from RNA degradation. To control RNase digestion was working, we extracted the HCV RNA and treated it with RNase prior to amplification. The HCV signal was eliminated completely, confirming the RNase digest was working as expected.

TABLE 7

Resistance of BVDV-non-CP7-HCV 5'NTR chimera RNA to RNase

| Sample | Ct: No RNase Treatment | Ct: RNase Digest Before Extraction | Ct: RNase Digest After Extraction |
|---|---|---|---|
| BVDV-non-CP7-HCV 5'NTR chimera K8 | 34.9 | 34.8 | Not tested |
| BVDV-non-CP7-HCV 5'NTR chimera K4 | 34.0 | 35.2 | Not tested |
| HCV | 38.1 | 37.7 | Negative |

EXAMPLE 11

Use of BVDV-non-CP7-HCV 5'NTR Chimera as an HCV Calibrator for HCV NAT Amplification Assays The performance of a known HCV calibrator (AcroMetrix OptiQuant HCV) consisting of intact naturally occurring HCV virions in plasma was compared with the performance of a BVDV-non-CP7-HCV 5 NTR chimeric HCV calibrator, which also consisted of intact virions in plasma. First, a value assignment of the 0.05% β-propiolactone inactivated BVDV-non-CP7-HCV 5 NTR stock material in plasma was conducted using an HCV Acrometrix Primary Standard (APS). The HCV APS is metrologically traceable to the Second HCV WHO Standard (NIBSC code: 96/798). The BVDV-non-CP7-HCV 5 NTR chimera sample was diluted to the same levels as the OptiQuant HCV panel members: 5E6, 5E5, 5E4, 5E3, 5E2, 5E1 IU/ml. The OptiQuant HCV panel had also been value assigned using the HCV APS. RNA extraction for the calibrators was performed using the QIAamp Virus MinElute Kit (QIAGEN) on the automated QIAcube instrument (QIAGEN). Real-time PCR was performed using a reverse transcription PCR HCV assay based on real time detection.

As shown in FIG. 12, the measured Ct values were plotted against the log of HCV IU/ml. The linear regression lines were equivalent for HCV and BVDV-non-CP7-HCV 5 NTR chimera panels within the measurement error: y=−3.80x+44.0 for BVDV-non-CP7-HCV 5 NTR chimera, and y=−3.82x+44.3 for OptiQuant HCV. The slopes of the two calibrators showed approximately equivalent PCR efficiencies: 87% for the BVDV-non-CP7-HCV 5 NTR chimera calibrator and 86% for the OptiQuant HCV calibrator. The coefficients of determination indicated a high degree of linearity: 0.98 for HCV-BVDV, and 0.99 for the OptiQuant HCV calibrator. The use of BVDV-non-CP7-HCV 5 NTRchimeric calibrator gave equivalent data compared to a known HCV calibrator that closely resembles patient samples, such as the AcroMetrix OptiQuant HCV panel.

EXAMPLE 12

Use of BVDV-non-CP7-HCV 5'NTR Chimera as an Internal Quantification Standard (QS)

In this experiment the HCV signal generated with the BVDV-non-CP7-HCV 5 NTR chimera functioned as QS for a quantitative West Nile Virus (WNV) assay. Four replicates of a WNV panel at 1E6, 1E5, 1E4, and 1E3 copies/ml were extracted using the Qiagen QIAcube with the Qiagen QIAamp MinElute Virus Spin Kit. 19.4 μl of BVDV at a concentration of 1E4 IU/ml was added as an internal quantification standard (QS) to the carrier RNA solution following the MinElute sample extraction protocol. 12.34 μl of the RNA eluate was amplified using WNV assay reagents, which also contained HCV-5'NTR primers and probes. The PCR reaction was run on an Applied Biosystems, ABI PRISM 7300. The data were analyzed using the Applied Biosystems Sequence Detection Software version 1.4.

The results of the linear regression analysis are shown in FIG. 13. A slope of 2.891 and a coefficient of determination of 0.996 was obtained from the equation of the line.

This experiment demonstrated usefulness of a BVDV chimera as an internal Quantification Standard (QS) in a quantitative NAT assay. The calibration curve for a quantitative WNV assay was generated by subtracting the WNV Ct value from the QS (BVDV-non-CP7-HCV 5 NTR) Ct and plotting the difference in Ct against the known WNV concentration in copies/mL (cp/mL).

EXAMPLE 13

Generation of a cDNA or Plasmid from Purified Chimeric Pesitvirus RNA

Donis and Vassilev described in U.S. Pat. No. 6,001,613 the generation of plasmid containing the cDNA of BVDV and producing infectious BVDV. The same methods and more recent methods known in the art can be used to purify viral RNA from the pestivirus-chimera and use the purified RNA to generate cDNA of this chimera. The cDNA can be cloned into a plasmid. The cDNA or plasmid would be useful as the starting point for generating new virus as described in Examples 3 and 4.

EXAMPLE 14

Generation of Chimeric BVDV-non-CP7 cDNAs Utilizing Various HCV Subtype 5'NTR Sequences (Subtypes 1-7)

Using similar techniques as detailed in Examples 1 and 2 (see FIGS. 8A-8C) for the insertion of 5'NTR of HCV subtype 1b into the 3'NTR of BVDV, HCV 5'NTR sequences from different known HCV subtypes (1a, 2a, 3a, 4a, 5a, 6p, and 7a) were successfully introduced into BVDV 3'NTR. As previously detailed in Example 2, synthetic DNA fragments were generated commercially for known sequences of various known subtypes of HCV 5'NTR regions (Sequences obtained from HCV Sequence Database, Los Alamos National Laboratory). The sequences of the HCV 5'NTR subtypes are shown in FIGS. 14A-14G (see SEQ ID NO: 13-19). Each of these HCV 5'NTR were introduced into the 3'NTR of BVDV using the methods detailed in Examples 1 and 2. Similar to the results obtained with HCV subtype 1b in Example 2, the BVDV-HCV hybrids obtained from the various HCV 5'NTR subtypes were stable, resistant to RNAse and were infectious (data not shown). The ability to utilize different subtypes of HCV allows the user to detect and quantify specific HCV genotypes, which vary in their geographic distribution.

EXAMPLE 15

Generation of Chimeric BVDV-ECMV IRES-EGFP (1325 bp) Containing Additional Open Reading Frame of the Enhanced Green Fluorescent Protein (EGFP) Gene An ECMV IRES-EGFP insertion sequence was prepared by amplification from a plasmid pIRES-EGFP, which was constructed to contain a 1325 bp sequence of an internal ribosome entry site (IRES) sequence from Encephalomyocarditis virus (ECMV) and additional open reading frame (ORF) of the EGFP gene. The ECMV IRES allows for translation of the EGFP reading frame from the BVDV 3'NTR, which is normally not translated. The plasmid pIRES-EGFP contained SnaBI (5') and PacI (3') restriction sites, respectively, as were utilized in Examples 1 and 2. The sequence of the ECMV IRES-EGFP ORF is shown in FIG. 15 (SEQ ID NO: 20). Using the same methodology as detailed in Examples 1 and 2, the ECMV IRES-EGFP sequence was successfully introduced into the 3'NTR of BVDV between the SnaBI and PacI restriction sites. FIG. 16 shows the genomic organization of the chimeric BVDV-ECMV-GFP virus with the ECMV IRES and EGFP open reading frame inserted 3'NTR of the BVDV following the NS5G gene. As with the other chimeric BVDV viruses in the above Examples, the chimeric BVDV-ECMV IRES-EGFP virus was stable, resistant to RNAse and was infectious (data not shown).

Histological analysis of MDBK cells infected with the chimeric BVDV-ECMV IRES-EGFP virus showed the inserted heterologous EGFP protein was expressed (FIGS. 17A-17C). FIG. 17A shows a culture of chimeric infected MDBK cells stained with DAPI stain, which stains nuclei of viable cells. FIG. 17B shows the results obtained when the MDBK cells were stained with antibody against BVDV NS3 protein, indicating the MDBK cells contained infectious BVDV virus. FIG. 17C shows the fluorescence of the EGFP protein obtained for chimeric BVDV-ECMV-EGFP infected MDBK cells, indicating the heterologous expression of EGFP protein in the infected MDBK cells. The EGFP fluorescence was clearly evident, indicating high levels of expression of the inserted EGFP.

This Example demonstrates: (1) that longer inserts than those previously shown in above Examples with HCV may be introduced into the 3'NTR of BVDV using the methods detailed in Examples 1 and 2. Here, a sequence of 1325 bp was successfully and stably introduced into the 3'NTR of BVDV, and (2) the longer insertion sequence may contain a heterologous additional open reading frame, as shown by the successful cellular expression of the open reading frame for the EGFP gene.

What is claimed is:

1. An in vitro method to replicate chimeric Pestivirus in a host cell comprising:

inserting into a Pestivirus RNA sequence a second RNA sequence within a variable region of a 3' non-translated region (NTR) of the Pestivirus RNA sequence downstream of a 5' UGA box to produce a chimeric Pestivirus RNA sequence, wherein the Pestivirus is bovine viral diarrhea virus (BVDV) and wherein the second RNA sequence is selected from the group consisting of Hepatitis C Virus (HCV), HCV genotypes 1-7, and combinations thereof;

transfecting the chimeric Pestivirus RNA sequence into a host cell; and stably replicating the chimeric Pestivirus in the host cell.

2. The method of claim 1 wherein the BVDV is non-CP7 clone.

3. The method of claim 1 wherein the second RNA sequence is located between the 5' UGA box and a 3' UGA-like box.

4. The method of claim 1 wherein the second RNA sequence is inserted between the $SL_{STOP}$ stem-loop and an SLII stem-loop.

5. The method of claim 1 wherein the second RNA sequence is located between a $UGA_{pos.cons}$ box and the SLII stem-loop.

6. The method of claim 1 wherein the second RNA sequence is a portion of a Hepatitis C virus (HCV).

7. The method of claim 6 wherein the portion of the HCV virus is comprised of at least 8 nucleotides.

8. The method of claim 6 wherein the second RNA sequence is at least a portion of a 5' NTR region of the HCV virus.

* * * * *

SEQUENCE LISTING

<160> NUMBER OF SEQ ID NOS: 20

<210> SEQ ID NO 1
<211> LENGTH: 12267
<212> TYPE: DNA
<213> ORGANISM: pestivirus type 1
<220> FEATURE:
<221> NAME/KEY: misc_feature
<223> OTHER INFORMATION: BVDV-non-CP7

<400> SEQUENCE: 1
gtatacgagg ttaggcaagt tctcgtatac atattggaca ctctaaaaat aattaggcct 60
aggggacaaa aatcctcctt agcgaaggcc gaaaagaggc taaccatgcc cttagtagga 120
ctagcaaaat aagggggta gcaacagtgg cgagttcgtt ggatggctga agccctgagt 180
acagggtagt cgtcagtggt tcgacgcttt ggaggacaag cctcgagatg ccacgtggac 240
gagggcatgc ccacagcaca tcttaacctg gacaggggtc gttcaggtga aaacggttta 300
accaaccgct acgaatacag tctgatagga tgctgcagag gcccactgta ttgctactga 360
aaatctctgc tgtacatggc acatggagtt gatcacaaat gaacttttat acaaaacata 420
caaacaaaaa cccgctggag tggaggaacc agtatacgac caagctggta accctttgtt 480
tggagaaaga ggagtgattc atccgcagtc aacgctaaaa cttccacata aaagagggga 540
gcgtgaagtc cccaccaatc tggcttcttt accaaaaaga ggtgactgca ggtcgggtaa 600
cagcaagggg cctgtgagtg gaatctactt aaaaccaggg ccgttattct accaagatta 660
taaaggacct gtctatcata gagccccatt ggagtttttt gaggaggcgt ctatgtgtga 720
gacaactaaa agaataggga gagtaactgg tagtgacagc agattatacc acatttacgt 780
gtgtattgat gggtgcataa tagtcaagag tgctacaaaa gaccgccaga aagtactcaa 840
gtgggtccac aacaagctaa actgcccct atgggtttca agctgctccg acacaaaaga 900
tgaaggggtg gtgaggaaga agcaacaaaa gccagatagg ttggaaaagg ggagaatgaa 960
gataacacct aaggagtcag agaaagacag taagaccaag ccgccagatg ctacgatagt 1020
ggtagatgga gtcaagtatc aggtaaagaa aaaaggaaaa gtcaagagca agaacaccca 1080
ggacggctta taccacaaca aaaataaacc tcaagagtcg cgcaagaaac tagagaaagc 1140
cctattggcc tgggcaataa tagccctggt tttctttcaa gtcacaatgg gagagaacat 1200
aacgcaatgg aacttacaag ataatggaac ggaaggcata caacgagcca tgtttcaaag 1260
aggagtgaat agaagtttac atgggatctg gccagagaaa atctgtacag gtgttccttc 1320
ccacctggcc actgacacag aattgaaggc aattcatggt atgatggatg caagtgagaa 1380
gacaaattat acgtgctgca gactccaacg ccatgaatgg aacaaacatg gttggtgcaa 1440
ctggtacaac attgaacctt ggatcctcct tatgaataaa actcaggcca accttactga 1500
gggtcagcca ctaagggagt gtgccgtcac atgccggtat gatcgagata gtgacctgaa 1560
tgtagtaaca caagccaggg atagccccac accattaaca ggttgcaaga aaggcaaaaa 1620
cttttccttt gcaggcatat tggtacaagg gccttgcaac tttgaaatag ccgtaagtga 1680
tgtgctgttc aaagagcatg attgcactag tgtgattcaa gacacagctc actacctcgt 1740
agacgggatg accaactccc tagagagtgc caggcaaggg accgcgaaac taacaacttg 1800
gctgggcagg cagcttggga tactaggaaa gaaactggaa aacaagagta agacatggtt 1860
tggggcatat gcagcctctc cctattgtga ggtagaacgg aagcttggtt acatctggta 1920
tacaaagaat tgcactccag cctgtttgcc taggaataca aagatcatcg gccccggtag 1980

-continued gtttgacacc aatgccgagg atggtaaaat actgcatgag atggggggtc acttgtcgga 2040
ggtgctacta ctctcagtgg tagtgctgtc cgatttcgct ccagagacag ccagtgtgat 2100
atacttgatt cttcatttct ccatcccaca aggacacact gatatacaag attgtgacaa 2160
aaaccaacta aacctcaccg tagaactcac aacagcagaa gtaataccag gctcagtttg 2220
gaacttgggt aaatatgttt gtgtaagacc agattggtgg ccttatgaga cagccacagt 2280
cctggtgatt gaagaggtgg gtcaagtaat taaggttgtc ttaagggcgt taaaagatct 2340
gacgcgcatt tggaccgctg ctacaaccac tgcattcttg gtttgtctgg tgaaggtagt 2400
gagaggccaa gtgttacaag gtatactgtg gctgatgctc ataacagggg cgcaagggta 2460
cccagactgc aaacccggct tttcatacgc catagccaaa aatgatgaga ttggcccact 2520
tggagctaca ggcctcacca ctcagtggta cgaatactcg gatgggatgc ggctgcagga 2580
ctcagtagtt gaagtttggt gtaaaaatgg agagatcaaa tatctaatca gatgcgggag 2640
ggaagccagg tatctggctg ttctacacac gagagccttg ccgacatctg tagtatttga 2700
aaaaattttt gatgggaaag aacaagagga catagtagaa atggatgaca actttgaatt 2760
cggtctttgc ccgtgtgatg ctagaccctt gataagggga aaatttaata caacacttct 2820
aaatgggcca gccttccaga tggtttgccc tataggatgg acagggactg taagctgtac 2880
actggccaat aaggatacgt tagccacaat cgttgtgaga acgtataaga gggtcaggcc 2940
ttttccatat aggcaggact gtgtcaccca gaaaaccatc ggggaagacc tctacgactg 3000
tgccttagga gggaattgga cttgtgtgcc gggggatgca ctacgatatg tagctgggcc 3060
cgttgagtct tgtgagtggt gtggttacaa gtttttaaaa agtgagggtc tgccgcattt 3120
cccaatcggc aaatgcaggc tgaagaatga gagtggctat agacaagtgg atgagacttc 3180
ttgcaacaga aacggcgtgg ctatagtgcc atctggcacg gtcaaatgca agatagggga 3240
cacggtggtg caagtcattg caatggatga taaactaggg cctatgcctt gcaaaccaca 3300
tgaaatcata tccagtgagg ggccagtgga aaagacggca tgcaccttca actacacaag 3360
aacattaaaa aacaagtact ttgagcccag ggataactat tttcaacaat acatgttaaa 3420
gggggagtac caatattggt ttgacctaga gatcactgac caccaccgag attacttcgc 3480
tgagtccctg ttggtgatag tagttgcact cctgggtggc aggtacgtgc tttggctgct 3540
ggtcacatac atgatcttat cagaacagat ggcctcgggt gtccagtatg gggcaggtga 3600
aatagtgatg atgggcaact tgttaacaca tgacagtgtt gaagtggtga catatttctt 3660
actactatac ctactactaa gagaggaaaa caccaaaaaa tgggtcatac ttatatacca 3720
catcatagta atgcatcctc taaaatcggt gacggtgata ttgctaatgg ttggggggat 3780
ggcaaaggct gaaccaggtg cccaggggta cctagagcag gtagacctta gttttacgat 3840
gattacgatc atcgtaatag gtctggttat agctaggcgt gatcccactg tggtgccact 3900
agtcactata gtcgcggcac tgaagatcac aggactaggc tttgggcccg gagtggatgc 3960
agctatggca gttctcacct taaccctact gatgactagt tatgtgacag actacttcag 4020
gtataaaagg tggatacaat gtatcctcag cttagtagcc ggggtgttcc ttatccggac 4080
cctcaaacat ctaggtgaac tcaaaacccc tgagctgacc ataccaaatt ggaggccact 4140
aaccttcata ctattatacc tgacttcagc aacagttgtt acaagatgga aaattgatat 4200
agctggcata ttcctgcaag ggcccctat cctttgatg atcgccaccc tatgggctga 4260
cttcttgact cttgttctga tcctacccac ctacgaatta gccaagctgt actacctaaa 4320
gaacgtcaag actgacgtgg agaagagttg gctggggggg ttagactaca ggacaattga 4380

-continued

```
ctctgtctat gatgtggatg aaagtggaga aggcgtgtac ctcttcccgt ccagacagaa   4440
gaaaaataag aatatcagca tactcttgcc cctcatcaga gctacgctaa taagttgtat   4500
tagcagcaaa tggcagatgg tgtatatggc ttacttaacc ctggacttta tgtactacat   4560
gcacagaaag gttattgaag agatatcagg gagtaccaat gtgatgtcta gagtgatagc   4620
agcacttata gaattaaact ggtccatgga agaagaagag agcaagggct taaagaagtt   4680
ttttatacta tctggaaggt tgaggaacct tataataaag cataaggtta ggaaccagac   4740
tgtggcaagc tggtatgggg aggaagaagt ctacggcatg ccaaaagtcg taaccataat   4800
aagggcctgc acgctaaaca agaacaaaca ttgcataata tgcacagtat gtgaggctag   4860
aaagtggaag ggaggcaact gccctaaatg cggccgccac gggaagccca tcatttgtgg   4920
gatgactcta gcggattttg aagaaaggca ctacaagaga atttttataa gggaaggtaa   4980
ctttgaagga cccttcaggc aggaatacaa tgggtttgta caatacaccg ctagggggca   5040
attgttcctg agaaatttac ccatattggc aaccaaagta aaaatgatca tggtaggcaa   5100
cctaggagag gaaatcggtg atctagaaca cctaggatgg atcctaaggg gacctgccgt   5160
gtgcaagaaa ataactgagc acgaaaaatg ccatgtcaac atactggaca agctgactgc   5220
gtttttgga gttatgccaa gagggactac accaagggct ccggtgagat tcccaacagc   5280
actactaaag gtaaggaggg gattggaaac cggttgggct tacacgcatc aaggtggcat   5340
aagctcagta gaccatgtga ccgctggcaa ggatctattg gtttgtgaca gtatgggtag   5400
aactagagtg gtttgccaaa gcaacaacaa gttaactgat gagacagaat atggtgtcaa   5460
gacggactcc ggatgtccag atggtgccag atgctatgta ttaaacccag aggcagtaaa   5520
tatatcaggg tccaagggag ctgtcgtaca cctccaaaaa acgggtgggg aatttacatg   5580
tgttactgca tcaggtacac cggccttctt cgacctgaaa aatttgaaag gatggtcggg   5640
tctacccata tttgaagcct ccagcggcag agtggttggc agagtcaaag tgggaaagaa   5700
tgaggaatcc aaacccacaa aattaatgag tggtatccaa actgtttcta aaaatacggc   5760
cgatttaaca gaaatggtca agaagataac cagcatgaac aggggggact ttaggcagat   5820
aacccttgca acaggggcag ggaagaccac tgagctccca aaagcagtga tagaggagat   5880
aggacgacac aaacgggtac tagtgctcat accattaaga gcagcagctg agtcagtcta   5940
tcaatacatg agattgaaac acccaagtat ctcctttaac ctgagaatag gggacatgaa   6000
agaaggggat atggcaaccg ggatcaccta cgcctcatat ggatattttt gccaaatgcc   6060
acaaccaaag ctcagagcag caatgataga gtattcatac atatttctgg atgagtatca   6120
ctgcgctact cctgagcagt tggctgttat aggaaaaatt cacagatttt ctgagagcat   6180
aagagtggtt gccatgactg ccaccccagc agggtcagta accacaacag ggcaaaaaca   6240
cccaatagaa gaattcatag cccctgaggt gatgaaaggg gaggaccttg gaagccagtt   6300
ccttgacata gcggggttaa agatccctgt agaggagatg aagggtaaca tgttggtttt   6360
cgtgcccacg aggaacatgg cagttgaagt agccaagaaa ctaaaagcca agggctacaa   6420
ctcagggtat tactacagtg gggaagaccc agctaacttg agagtggtaa catcacagtc   6480
cccatacgtc gtggtagcca ctaatgccat cgagtcaggg gtaacgctgc cagatttaga   6540
tacagttgtt gacacaggtc tgaaatgtga gaagagggtg agggtgtctt ccaaaatacc   6600
ctttatagta acaggcctta agagaatggc tgtcactgtg ggcgaacagg ctcagcggag   6660
aggcagggta ggtagagtga aacccggtag gtattataga agtcaggaaa cagcaaccgg   6720
```

-continued

```
gtcaaaggac taccactatg acttgttaca ggcacagagg tacgggatcg aagatgggat   6780
caacgtaaca aagtccttta gggagatgaa ttatgactgg agcctgtatg aggaagacag   6840
cttgctgata acccagctgg agatactgaa caatctactc atctctgaag atttaccagc   6900
agctgttaaa aacatcatgg caagaactga tcacccagag cctatccagc ttgcatataa   6960
cagttatgag gtccaagtcc ctgtgctgtt cccaaaaata aggaatgggg aggtcacaga   7020
cacttacgag aactactcat tcctaaatgc aaggaaacta ggggaagacg tgcccgtgta   7080
cgtttatgcc accgaagatg aagatctggc tgtggacctt ctaggcttgg actggccaga   7140
cccagggaat cagcaagtag tggagactgg gaaggcactg aagcaagtgg taggactgtc   7200
ctctgccgaa aatgccttgc tcatagccct atttgggtat gtaggatacc aagccttgtc   7260
aaaaagacac gtcccaatga tcacagacat atacactata gaagatcaaa gactagagga   7320
cacaacccac cttcaatatg cgcccaatgc cataagaact gaggggaagg agactgaact   7380
aaaggaatta gcagtgggtg acttggacaa aatcatgggt tccatctcgg actatgcatc   7440
agagggattg aatttcgtaa ggtcccaagc agaaaagatg agatctgccc ccgctttcaa   7500
agaaaacgtg gaagctgcta aagggtacgt ccaaaagttt attgattctc tcatagaaaa   7560
taaagaaacc ataatcagat atggcctgtg ggaacacac acggcactct acaagagtat   7620
tgccgcgaga ttgggtcatg aaactgcatt cgctacacta gtgataaagt ggctggcctt   7680
cgggggtgag tcggtgtcag accacatgag acaagcagct gtcgacctgg ttgtttatta   7740
tgtgatcaat aagccctcct tcccagggga ttctgaaacc caacaggaag gaaggcgatt   7800
cgtcgccagc ctgttcatct ccgctttggc aacctacaca tacaaaactt ggaattacaa   7860
caacctctcc aaggtagtag aaccagcctt agcatacctc ccctatgcta ccaatgcact   7920
aaaaatgttt accccgacca gactggagag cgtagttata cttagtacca caatatacaa   7980
aacttacctc tcaataagga agggaaagag tgatggactg ttgggtacag ggatcagtgc   8040
agcaatggag attctatcac agaacccagt gtcggtaggt atatctgtca tgctgggggt   8100
gggggcgatt gccgcgcaca atgccattga gtctagtgaa caaaaaagga ccctgttgat   8160
gaaagtgttt gtaaaaaact tcctggacca ggcggcaaca gatgagctgg taaaggaaaa   8220
cccagagaaa ataataatgg ccctatttga agcagtccag acaattggca accccttgag   8280
gctcatatat cacctgtatg gggtttacta caaaggctgg gaagcaaaag aactatcaga   8340
gagaacagca ggcaggaacc tgttcacctt gataatgttc gaagccttcg aactactagg   8400
gatggactct gaagggaaga taaggaacct gtctgggaat tatgtcctgg atttgatcta   8460
cagcctacat aaacagataa atagaggctt gaaaaaaata gtcttggggt gggctcccgc   8520
accatttagt tgcgactgga ctcctagtga tgagagaatt aggttaccca caaacaacta   8580
tctaagagta gaaactaagt gtccatgtgg ctatgagatg aaagcactaa ggaacgttgg   8640
tggcagtctt accaaagtgg aggagaaagg accttttctc tgcaggaaca ggcttggtag   8700
agggccggtc aactatagag tcacaaagta ctatgatgac aacctcaaag agataaaacc   8760
agttgctaaa ctagaaggat ttgtggatca ctattacaaa ggtgttacag caaggataga   8820
ttatggcaga gggaaaatgc tattagctac tgataaatgg gaggtggagc acggtgttgt   8880
cactaggttg gcaaagagat ataccggagt tggattcaag ggagcatacc tgggtgatga   8940
acccaaccac cgcgacctag tagaaagaga ctgtgcaact ataacaaaaa atacagtgca   9000
gtttttaaaa atgaagaaag gctgtgcatt tacctatgac ttaaccctgt ccaatttaac   9060
caggttaatt gaattggtac acaaaaataa cctagaagag aaagacatac cagcagccac   9120
```

```
agtaacgaca tggctggctt atacttttgt aaatgaagat attgggacta taaaaccagt   9180
actaggagag agagtggtca ccgacccagt ggtggatgtt aacttacaac cagaagtaca   9240
agtggataca tcagaggttg ggatcacttt agttggtagg gcagccttaa tgacgacagg   9300
tactacaccc gtagtcgaaa aaacagagcc caatgctgat ggtggtccaa gctccataaa   9360
gattgggttg gatgaaggaa gatacccagg acctggactg caagaccgca ccttgaccga   9420
tgaaatacat tctagggatg aaaggccctt tgttctagtc ctgggctcaa aaaattctat   9480
gtcaaataga gctaaaactg ctagaaacat caacttatac aaggggaata accccaggga   9540
gattagagat ctgatggcac aggggcgtat gctagttgtg gccttaaagg attttaaccc   9600
tgagttgtct gaactagttg atttcaaggg gactttctta gacagggaag ccttggaagc   9660
tctcagcctg ggcggccaa agtccaagca ggtgaccaca gccacagtta gggagttatt   9720
agagcaggag gtacaagttg agatccccag ttggtttgga gcaggtgatc cagtcttctt   9780
ggaagtgact ttgaagggtg acagatatca cttagtagga gatgtagata gagtgaaaga   9840
tcaagcgaag gagcttgggg ccacggacca gacaagaata gtgaaggaag tgggtgcaag   9900
aacctatacc atgaagctgt ctagttggtt tcttcaggca acaaataaac agatgagctt   9960
gaccccttta tttgaggagc tattgctacg ttgcccccct aaaataaaga gcaataaagg  10020
gcacatggca tcagcttacc aactagcaca gggaaactgg gagccccttg actgtggagt  10080
tcacctgggc accatacctg ccaggagggt aaaaatccac ccatatgaag cttacctgaa  10140
actgaaggat ttattggaag aagaagaaaa gaaaccaaag tgtagagaca cagtaataag  10200
agaacacaac aagtggatcc tcaaaaaagt gaggcaccag ggtaatctca atacaaagaa  10260
aatcctcaac cctggaaagc tatcagaaca gctagataga gaagggcata aaagaaacat  10320
ttataacaat cagattggca ccataatgac ggaagcagga agtaggttgg aaaaattacc  10380
agtcgtcaga gcccaaactg acactaaaag cttccatgag gcaatcagag ataagataga  10440
caagaatgaa aatcagcaga gcccaggact gcatgataaa ttgttagaga tctttcatac  10500
aatagcccaa cccagcctaa gacacaccta cagtgacgtg acgtgggagc aacttgaggc  10560
aggggttaat agaaaggggg ctgctggctt tctagagaag aagaatgttg gagaagtact  10620
ggactcagag aagcacctgg tggaacaact gatcagagat ttgaaaacag gaaggaagat  10680
aagatattat gagacagcaa taccaaaaaa tgagaagaga gatgtcagtg atgattggca  10740
atcaggggac ttagtagatg agaagaaacc aagggtgatt caataccctg aagctaaaac  10800
aagactagcc atcactaaag taatgtacaa ctgggtgaaa cagcagcccg tcgtgatccc  10860
agggtatgaa gggaagaccc cattatttaa cattttcaac aaggtgagga aggaatggga  10920
tttgttcaat gaaccagtag ctgtgagttt cgacactaag gcttgggaca cccaagtaac  10980
tagtagagat ctacggctta ttggtgaaat tcaaaaatat tactacagga aagagtggca  11040
caaattcatc gataccatta ctgaccatat ggtggaggtg cccgtcataa cggcagatgg  11100
tgaggtatac ataagaaatg gacaaagggg tagtggccag ccagacacaa gtgcaggcaa  11160
tagcatgcta aacgtgttaa caatgatgta tgccttctgt gaaagtacgg gggttccata  11220
caagagtttc aatagggttg caaggatcca tgtctgtggg gatgacggct tcctaataac  11280
agagaagggg ctgggattaa agtttgccaa caatgggatg caaattctgc acgaagcagg  11340
caagcctcaa aagataactg agggggaaag aatgaaagtt gcctataggt tcgaggacat  11400
agaattctgc tctcatacac cagtccccgt taggtggtct gataacacca gcagttacat  11460
```

```
ggccggcaga gacactgccg ttatattatc aaagatggca acaagattgg attcaagtgg  11520

agaaaggggt actatagcat atgaaaaagc agtggccttt agttttttgc tgatgtactc  11580

ctggaatcct cttgtgagga ggatctgtct actggtcctt tcacagcagc cagagacaac  11640

tccatcaacc cagaccactt actattataa aggagaccca ataggagcct acaaagatgt  11700

aataggtaag aatttgtgtg aattaaaaag gacgggtttt gaaaaattgg ccaatttaaa  11760

cctaagcctg tccacgttag gaatctggtc caaacataca agtaaaagaa tcatccaaga  11820

ctgtgtaacc atcgggaaag aggaaggcaa ttggctggtc aatgccgaca ggttgatatc  11880

tagcaaaact ggccatttgt acatacctga caaaggttat acattacaag ggaaacatta  11940

tgaacaactt caactgcagg caagaactag cccagtcacg ggagtaggga cggagagata  12000

taaactaggc cctatagtaa acctgctgct gaggaggttg agagttctgc ttatggcagc  12060

tgtcggtgcc agcagttgaa ataatgtatg tatatattgt atataaatct gtatttgtat  12120

atattatgtt taaatttagt tgagattagt agtgatatat agttatctac ctcaagctaa  12180

cactacactc aatgcacaca gcactttagc tgtatgaggg tacacccgac gtccacggtt  12240

ggactaggga aaacccttaa cagcccc                                      12267
```

```
<210> SEQ ID NO 2
<211> LENGTH: 341
<212> TYPE: DNA
<213> ORGANISM: Hepatitis C virus
<220> FEATURE:
<221> NAME/KEY: misc_feature
<223> OTHER INFORMATION: HCV 5' NTR

<400> SEQUENCE: 2

gccagccccc gattgggggc gacactccac catagatcac tcccctgtga ggaactactg     60

tcttcacgca gaaagcgtct agccatggcg ttagtatgag tgtcgtgcag cctccaggac    120

ccccctctc gggagagcca tagtggtctg cggaaccggt gagtacaccg gaattgccag    180

gacgaccggg tcctttcttg gatcaacccg ctcaatgcct ggagatttgg gcgtgccccc    240

gcgagactgc tagccgagta gtgttgggtc gcgaaaggcc ttgtggtact gcctgatagg    300

gtgcttgcga gtgcctcggg aggtctcgta gaccgtgcac c                        341
```

```
<210> SEQ ID NO 3
<211> LENGTH: 12625
<212> TYPE: DNA
<213> ORGANISM: pestivirus type 1
<220> FEATURE:
<221> NAME/KEY: misc_feature
<223> OTHER INFORMATION: BVDV non-CP7-HCV 5'NTR chimera

<400> SEQUENCE: 3

gtatacgagg ttaggcaagt tctcgtatac atattggaca ctctaaaaat aattaggcct     60

aggggacaaa aatcctcctt agcgaaggcc gaaaagaggc taaccatgcc cttagtagga    120

ctagcaaaat aagggggggta gcaacagtgg cgagttcgtt ggatggctga agccctgagt    180

acagggtagt cgtcagtggt tcgacgcttt ggaggacaag cctcgagatg ccacgtggac    240

gagggcatgc ccacagcaca tcttaacctg gacaggggtc gttcaggtga aaacggttta    300

accaaccgct acgaatacag tctgatagga tgctgcagag gcccactgta ttgctactga    360

aaatctctgc tgtacatggc acatggagtt gatcacaaat gaacttttat acaaaacata    420

caaacaaaaa cccgctggag tggaggaacc agtatacgac caagctggta accctttgtt    480

tggagaaaga ggagtgattc atccgcagtc aacgctaaaa cttccacata aaagagggga    540
```

-continued

```
gcgtgaagtc cccaccaatc tggcttcttt accaaaaaga ggtgactgca ggtcgggtaa    600
cagcaagggg cctgtgagtg gaatctactt aaaaccaggg ccgttattct accaagatta    660
taaaggacct gtctatcata gagccccatt ggagtttttt gaggaggcgt ctatgtgtga    720
gacaactaaa agaataggga gagtaactgg tagtgacagc agattatacc acatttacgt    780
gtgtattgat gggtgcataa tagtcaagag tgctacaaaa gaccgccaga aagtactcaa    840
gtgggtccac aacaagctaa actgccccct atgggtttca agctgctccg acacaaaaga    900
tgaaggggtg gtgaggaaga agcaacaaaa gccagatagg ttggaaaagg ggagaatgaa    960
gataacacct aaggagtcag agaaagacag taagaccaag ccgccagatg ctacgatagt   1020
ggtagatgga gtcaagtatc aggtaaagaa aaaaggaaaa gtcaagagca agaacaccca   1080
ggacggctta taccacaaca aaaataaacc tcaagagtcg cgcaagaaac tagagaaagc   1140
cctattggcc tgggcaataa tagccctggt tttctttcaa gtcacaatgg gagagaacat   1200
aacgcaatgg aacttacaag ataatggaac ggaaggcata caacgagcca tgtttcaaag   1260
aggagtgaat agaagtttac atgggatctg gccagagaaa atctgtacag gtgttccttc   1320
ccacctggcc actgacacag aattgaaggc aattcatggt atgatggatg caagtgagaa   1380
gacaaattat acgtgctgca gactccaacg ccatgaatgg aacaaacatg gttggtgcaa   1440
ctggtacaac attgaacctt ggatcctcct tatgaataaa actcaggcca accttactga   1500
gggtcagcca ctaagggagt gtgccgtcac atgccggtat gatcgagata gtgacctgaa   1560
tgtagtaaca caagccaggg atagccccac accattaaca ggttgcaaga aaggcaaaaa   1620
cttttccttt gcaggcatat tggtacaagg gccttgcaac tttgaaatag ccgtaagtga   1680
tgtgctgttc aaagagcatg attgcactag tgtgattcaa gacacagctc actacctcgt   1740
agacgggatg accaactccc tagagagtgc caggcaaggg accgcgaaac taacaacttg   1800
gctgggcagg cagcttggga tactaggaaa gaaactggaa aacaagagta agacatggtt   1860
tggggcatat gcagcctctc cctattgtga ggtagaacgg aagcttggtt acatctggta   1920
tacaaagaat tgcactccag cctgtttgcc taggaataca aagatcatcg gccccggtag   1980
gtttgacacc aatgccgagg atggtaaaat actgcatgag atggggggtc acttgtcgga   2040
ggtgctacta ctctcagtgg tagtgctgtc cgatttcgct ccagagacag ccagtgtgat   2100
atacttgatt cttcatttct ccatccccaca aggacacact gatatacaag attgtgacaa   2160
aaaccaacta aacctcaccg tagaactcac aacagcagaa gtaataccag gctcagtttg   2220
gaacttgggt aaatatgttt gtgtaagacc agattggtgg ccttatgaga cagccacagt   2280
cctggtgatt gaagaggtgg gtcaagtaat taaggttgtc ttaagggcgt taaaagatct   2340
gacgcgcatt tggaccgctg ctacaaccac tgcattcttg gtttgtctgg tgaaggtagt   2400
gagaggccaa gtgttacaag gtatactgtg gctgatgctc ataacagggg cgcaagggta   2460
cccagactgc aaacccggct tttcatacgc catagccaaa aatgatgaga ttggcccact   2520
tggagctaca ggcctcacca ctcagtggta cgaatactcg gatgggatgc ggctgcagga   2580
ctcagtagtt gaagtttggt gtaaaaatgg agagatcaaa tatctaatca gatgcgggag   2640
ggaagccagg tatctggctg ttctacacac gagagccttg ccgacatctg tagtatttga   2700
aaaaattttt gatgggaaag aacaagagga catagtagaa atggatgaca actttgaatt   2760
cggtctttgc ccgtgtgatg ctagaccctt gataaggggga aaatttaata caacacttct   2820
aaatgggcca gccttccaga tggtttgccc tataggatgg acagggactg taagctgtac   2880
```

-continued

```
actggccaat aaggatacgt tagccacaat cgttgtgaga acgtataaga gggtcaggcc   2940
ttttccatat aggcaggact gtgtcaccca gaaaaccatc ggggaagacc tctacgactg   3000
tgccttagga gggaattgga cttgtgtgcc gggggatgca ctacgatatg tagctgggcc   3060
cgttgagtct tgtgagtggt gtggttacaa gtttttaaaa agtgagggtc tgccgcattt   3120
cccaatcggc aaatgcaggc tgaagaatga gagtggctat agacaagtgg atgagacttc   3180
ttgcaacaga aacggcgtgg ctatagtgcc atctggcacg gtcaaatgca agatagggga   3240
cacggtggtg caagtcattg caatggatga taaactaggg cctatgcctt gcaaaccaca   3300
tgaaatcata tccagtgagg ggccagtgga aaagacggca tgcaccttca actacacaag   3360
aacattaaaa aacaagtact ttgagcccag ggataactat tttcaacaat acatgttaaa   3420
gggggagtac caatattggt ttgacctaga gatcactgac caccaccgag attacttcgc   3480
tgagtccctg ttggtgatag tagttgcact cctgggtggc aggtacgtgc tttggctgct   3540
ggtcacatac atgatcttat cagaacagat ggcctcgggt gtccagtatg ggcaggtga    3600
aatagtgatg atgggcaact tgttaacaca tgacagtgtt gaagtggtga catatttctt   3660
actactatac ctactactaa gagaggaaaa caccaaaaaa tgggtcatac ttatatacca   3720
catcatagta atgcatcctc taaaatcggt gacggtgata ttgctaatgg ttggggggat   3780
ggcaaaggct gaaccaggtg cccaggggta cctagagcag gtagacctta gttttacgat   3840
gattacgatc atcgtaatag gtctggttat agctaggcgt gatcccactg tggtgccact   3900
agtcactata gtcgcggcac tgaagatcac aggactaggc tttgggcccg gagtggatgc   3960
agctatggca gttctcacct taaccctact gatgactagt tatgtgacag actacttcag   4020
gtataaaagg tggatacaat gtatcctcag cttagtagcc ggggtgttcc ttatccggac   4080
cctcaaacat ctaggtgaac tcaaaacccc tgagctgacc ataccaaatt ggaggccact   4140
aaccttcata ctattatacc tgacttcagc aacagttgtt acaagatgga aaattgatat   4200
agctggcata ttcctgcaag ggcccctat ccttttgatg atcgccaccc tatgggctga    4260
cttcttgact cttgttctga tcctacccac ctacgaatta gccaagctgt actacctaaa   4320
gaacgtcaag actgacgtgg agaagagttg gctggggggg ttagactaca ggacaattga   4380
ctctgtctat gatgtggatg aaagtggaga aggcgtgtac ctcttcccgt ccagacagaa   4440
gaaaaataag aatatcagca tactcttgcc cctcatcaga gctacgctaa taagttgtat   4500
tagcagcaaa tggcagatgg tgtatatggc ttacttaacc ctggacttta tgtactacat   4560
gcacagaaag gttattgaag agatatcagg gagtaccaat gtgatgtcta gagtgatagc   4620
agcacttata gaattaaact ggtccatgga agaagaagag agcaagggct taaagaagtt   4680
ttttatacta tctggaaggt tgaggaacct tataataaag cataaggtta ggaaccagac   4740
tgtggcaagc tggtatgggg aggaagaagt ctacggcatg ccaaaagtcg taaccataat   4800
aagggcctgc acgctaaaca agaacaaaca ttgcataata tgcacagtat gtgaggctag   4860
aaagtggaag ggaggcaact gccctaaatg cggccgccac gggaagccca tcatttgtgg   4920
gatgactcta gcggattttg aagaaaggca ctacaagaga atttttataa gggaaggtaa   4980
ctttgaagga cccttcaggc aggaatacaa tgggtttgta caatacaccg ctagggggca   5040
attgttcctg agaaatttac ccatattggc aaccaaagta aaaatgatca tggtaggcaa   5100
cctaggagag gaaatcggtg atctagaaca cctaggatgg atcctaaggg gacctgccgt   5160
gtgcaagaaa ataactgagc acgaaaaatg ccatgtcaac atactggaca agctgactgc   5220
gttttttgga gttatgccaa gagggactac accaagggct ccggtgagat tcccaacagc   5280
```

```
actactaaag gtaaggaggg gattggaaac cggttgggct tacacgcatc aaggtggcat   5340
aagctcagta gaccatgtga ccgctggcaa ggatctattg gtttgtgaca gtatgggtag   5400
aactagagtg gtttgccaaa gcaacaacaa gttaactgat gagacagaat atggtgtcaa   5460
gacggactcc ggatgtccag atggtgccag atgctatgta ttaaacccag aggcagtaaa   5520
tatatcaggg tccaagggag ctgtcgtaca cctccaaaaa acgggtgggg aatttacatg   5580
tgttactgca tcaggtacac cggccttctt cgacctgaaa aatttgaaag gatggtcggg   5640
tctacccata tttgaagcct ccagcggcag agtggttggc agagtcaaag tgggaaagaa   5700
tgaggaatcc aaacccacaa aattaatgag tggtatccaa actgtttcta aaaatacggc   5760
cgatttaaca gaaatggtca agaagataac cagcatgaac agggggggact ttaggcagat   5820
aacccttgca acaggggcag ggaagaccac tgagctccca aaagcagtga tagaggagat   5880
aggacgacac aaacgggtac tagtgctcat accattaaga gcagcagctg agtcagtcta   5940
tcaatacatg agattgaaac acccaagtat ctcctttaac ctgagaatag gggacatgaa   6000
agaaggggat atggcaaccg ggatcaccta cgcctcatat ggatattttt gccaaatgcc   6060
acaaccaaag ctcagagcag caatgataga gtattcatac atatttctgg atgagtatca   6120
ctgcgctact cctgagcagt tggctgttat aggaaaaatt cacagatttt ctgagagcat   6180
aagagtggtt gccatgactg ccaccccagc agggtcagta accacaacag ggcaaaaaca   6240
cccaatagaa gaattcatag cccctgaggt gatgaaaggg gaggaccttg gaagccagtt   6300
ccttgacata gcggggttaa agatccctgt agaggagatg aagggtaaca tgttggtttt   6360
cgtgcccacg aggaacatgg cagttgaagt agccaagaaa ctaaaagcca agggctacaa   6420
ctcagggtat tactacagtg gggaagaccc agctaacttg agagtggtaa catcacagtc   6480
cccatacgtc gtggtagcca ctaatgccat cgagtcaggg gtaacgctgc cagatttaga   6540
tacagttgtt gacacaggtc tgaaatgtga gaagagggtg agggtgtctt ccaaaatacc   6600
ctttatagta acaggcctta agagaatggc tgtcactgtg ggcgaacagg ctcagcggag   6660
aggcagggta ggtagagtga aacccggtag gtattataga agtcaggaaa cagcaaccgg   6720
gtcaaaggac taccactatg acttgttaca ggcacagagg tacgggatcg aagatgggat   6780
caacgtaaca aagtccttta gggagatgaa ttatgactgg agcctgtatg aggaagacag   6840
cttgctgata acccagctgg agatactgaa caatctactc atctctgaag atttaccagc   6900
agctgttaaa aacatcatgg caagaactga tcacccagag cctatccagc ttgcatataa   6960
cagttatgag gtccaagtcc ctgtgctgtt cccaaaaata aggaatgggg aggtcacaga   7020
cacttacgag aactactcat tcctaaatgc aaggaaacta ggggaagacg tgcccgtgta   7080
cgtttatgcc accgaagatg aagatctggc tgtggacctt ctaggcttgg actggccaga   7140
cccagggaat cagcaagtag tggagactgg gaaggcactg aagcaagtgg taggactgtc   7200
ctctgccgaa aatgccttgc tcatagccct atttgggtat gtaggatacc aagccttgtc   7260
aaaaagacac gtcccaatga tcacagacat atacactata gaagatcaaa gactagagga   7320
cacaacccac cttcaatatg cgcccaatgc cataagaact gaggggaagg agactgaact   7380
aaaggaatta gcagtgggtg acttggacaa aatcatgggt tccatctcgg actatgcatc   7440
agagggattg aatttcgtaa ggtcccaagc agaaaagatg agatctgccc ccgctttcaa   7500
agaaaacgtg gaagctgcta aagggtacgt ccaaaagttt attgattctc tcatagaaaa   7560
taaagaaacc ataatcagat atggcctgtg gggaacacac acggcactct acaagagtat   7620
```

```
tgccgcgaga ttgggtcatg aaactgcatt cgctacacta gtgataaagt ggctggcctt   7680
cgggggtgag tcggtgtcag accacatgag acaagcagct gtcgacctgg ttgtttatta   7740
tgtgatcaat aagccctcct tcccagggga ttctgaaacc caacaggaag gaaggcgatt   7800
cgtcgccagc ctgttcatct ccgctttggc aacctacaca tacaaaactt ggaattacaa   7860
caacctctcc aaggtagtag aaccagcctt agcatacctc ccctatgcta ccaatgcact   7920
aaaaatgttt accccgacca gactggagag cgtagttata cttagtacca caatatacaa   7980
aacttacctc tcaataagga agggaaagag tgatggactg ttgggtacag ggatcagtgc   8040
agcaatggag attctatcac agaacccagt gtcggtaggt atatctgtca tgctgggggt   8100
gggggcgatt gccgcgcaca atgccattga gtctagtgaa caaaaaagga ccctgttgat   8160
gaaagtgttt gtaaaaaact tcctggacca ggcggcaaca gatgagctgg taaaggaaaa   8220
cccagagaaa ataataatgg ccctatttga agcagtccag acaattggca accccttgag   8280
gctcatatat cacctgtatg ggtttacta caaaggctgg gaagcaaaag aactatcaga   8340
gagaacagca ggcaggaacc tgttcacctt gataatgttc gaagccttcg aactactagg   8400
gatggactct gaagggaaga taaggaacct gtctgggaat tatgtcctgg atttgatcta   8460
cagcctacat aaacagataa atagaggctt gaaaaaaata gtcttggggt gggctcccgc   8520
accatttagt tgcgactgga ctcctagtga tgagagaatt aggttaccca caaacaacta   8580
tctaagagta gaaactaagt gtccatgtgg ctatgagatg aaagcactaa ggaacgttgg   8640
tggcagtctt accaaagtgg aggagaaagg accttttctc tgcaggaaca ggcttggtag   8700
agggccggtc aactatagag tcacaaagta ctatgatgac aacctcaaag agataaaacc   8760
agttgctaaa ctagaaggat ttgtggatca ctattacaaa ggtgttacag caaggataga   8820
ttatggcaga gggaaaatgc tattagctac tgataaatgg gaggtggagc acggtgttgt   8880
cactaggttg gcaaagagat ataccggagt tggattcaag ggagcatacc tgggtgatga   8940
acccaaccac cgcgacctag tagaaagaga ctgtgcaact ataacaaaaa atacagtgca   9000
gtttttaaaa atgaagaaag gctgtgcatt tacctatgac ttaaccctgt ccaatttaac   9060
caggttaatt gaattggtac acaaaaataa cctagaagag aaagacatac cagcagccac   9120
agtaacgaca tggctggctt atacttttgt aaatgaagat attgggacta taaaaccagt   9180
actaggagag agagtggtca ccgacccagt ggtggatgtt aacttacaac cagaagtaca   9240
agtggataca tcagaggttg ggatcacttt agttggtagg gcagccttaa tgacgacagg   9300
tactacaccc gtagtcgaaa aaacagagcc caatgctgat ggtggtccaa gctccataaa   9360
gattgggttg gatgaaggaa gatacccagg acctggactg caagaccgca ccttgaccga   9420
tgaaatacat tctagggatg aaaggccctt tgttctagtc ctgggctcaa aaaattctat   9480
gtcaaataga gctaaaactg ctagaaacat caacttatac aaggggaata accccaggga   9540
gattagagat ctgatggcac aggggcgtat gctagttgtg gccttaaagg attttaaccc   9600
tgagttgtct gaactagttg atttcaaggg gactttctta gacagggaag ccttggaagc   9660
tctcagcctg ggcggccaa agtccaagca ggtgaccaca gccacagtta gggagttatt   9720
agagcaggag gtacaagttg agatccccag ttggtttgga gcaggtgatc cagtcttctt   9780
ggaagtgact ttgaagggtg acagatatca cttagtagga gatgtagata gagtgaaaga   9840
tcaagcgaag gagcttgggg ccacggacca gacaagaata gtgaaggaag tgggtgcaag   9900
aacctatacc atgaagctgt ctagttggtt tcttcaggca acaaataaac agatgagctt   9960
gaccccttta tttgaggagc tattgctacg ttgcccccct aaaataaaga gcaataaagg  10020
```

gcacatggca tcagcttacc aactagcaca gggaaactgg gagccccttg actgtggagt 10080
tcacctgggc accatacctg ccaggagggt aaaaatccac ccatatgaag cttacctgaa 10140
actgaaggat ttattggaag aagaagaaaa gaaaccaaag tgtagagaca cagtaataag 10200
agaacacaac aagtggatcc tcaaaaaagt gaggcaccag ggtaatctca atacaaagaa 10260
aatcctcaac cctggaaagc tatcagaaca gctagataga gaagggcata aaagaaacat 10320
ttataacaat cagattggca ccataatgac ggaagcagga agtaggttgg aaaaattacc 10380
agtcgtcaga gcccaaactg acactaaaag cttccatgag gcaatcagag ataagataga 10440
caagaatgaa aatcagcaga gcccaggact gcatgataaa ttgttagaga tctttcatac 10500
aatagcccaa cccagcctaa gacacaccta cagtgacgtg acgtgggagc aacttgaggc 10560
aggggttaat agaaaggggg ctgctggctt tctagagaag aagaatgttg gagaagtact 10620
ggactcagag aagcacctgg tggaacaact gatcagagat ttgaaaacag gaaggaagat 10680
aagatattat gagacagcaa taccaaaaaa tgagaagaga gatgtcagtg atgattggca 10740
atcaggggac ttagtagatg agaagaaacc aagggtgatt caataccctg aagctaaaac 10800
aagactagcc atcactaaag taatgtacaa ctgggtgaaa cagcagcccg tcgtgatccc 10860
agggtatgaa gggaagaccc cattatttaa cattttcaac aaggtgagga aggaatggga 10920
tttgttcaat gaaccagtag ctgtgagttt cgacactaag gcttgggaca cccaagtaac 10980
tagtagagat ctacggctta ttggtgaaat tcaaaaatat tactacagga aagagtggca 11040
caaattcatc gataccatta ctgaccatat ggtggaggtg cccgtcataa cggcagatgg 11100
tgaggtatac ataagaaatg gacaaagggg tagtggccag ccagacacaa gtgcaggcaa 11160
tagcatgcta aacgtgttaa caatgatgta tgccttctgt gaaagtacgg gggttccata 11220
caagagtttc aatagggttg caaggatcca tgtctgtggg gatgacggct tcctaataac 11280
agagaagggg ctgggattaa agtttgccaa caatgggatg caaattctgc acgaagcagg 11340
caagcctcaa aagataactg agggggaaag aatgaaagtt gcctataggt tcgaggacat 11400
agaattctgc tctcatacac cagtccccgt taggtggtct gataacacca gcagttacat 11460
ggccggcaga gacactgccg ttatattatc aaagatggca acaagattgg attcaagtgg 11520
agaaaggggt actatagcat atgaaaaagc agtggccttt agtttttgc tgatgtactc 11580
ctggaatcct cttgtgagga ggatctgtct actggtcctt tcacagcagc cagagacaac 11640
tccatcaacc cagaccactt actattataa aggagaccca ataggagcct acaaagatgt 11700
aataggtaag aatttgtgtg aattaaaaag gacgggtttt gaaaaattgg ccaatttaaa 11760
cctaagcctg tccacgttag gaatctggtc caaacataca agtaaaagaa tcatccaaga 11820
ctgtgtaacc atcgggaaag aggaaggcaa ttggctggtc aatgccgaca ggttgatatc 11880
tagcaaaact ggccatttgt acatacctga caaaggttat acattacaag ggaaacatta 11940
tgaacaactt caactgcagg caagaactag cccagtcacg ggagtaggga cggagagata 12000
taaactaggc cctatagtaa acctgctgct gaggaggttg agagttctgc ttatggcagc 12060
tgtcggtgcc agcagttgaa ataatgtatg tatatattgt atataaatct gtatttgtat 12120
atattatgtt taaatacgta gccagccccc gattgggggc gacactccac catagatcac 12180
tcccctgtga ggaactactg tcttcacgca gaaagcgtct agccatggcg ttagtatgag 12240
tgtcgtgcag cctccaggac cccccctctc gggagagcca tagtggtctg cggaaccggt 12300
gagtacaccg gaattgccag gacgaccggg tcctttcttg gatcaacccg ctcaatgcct 12360

```
ggagatttgg gcgtgccccc gcgagactgc tagccgagta gtgttgggtc gcgaaaggcc  12420

ttgtggtact gcctgatagg gtgcttgcga gtgcctcggg aggtctcgta gaccgtgcac  12480

cttaattaat aatttagttg agattagtag tgatatatag ttatctacct caagctaaca  12540

ctacactcaa tgcacacagc actttagctg tatgagggta cacccgacgt ccacggttgg  12600

actagggaaa acccttaaca gcccc                                        12625


<210> SEQ ID NO 4
<211> LENGTH: 12281
<212> TYPE: DNA
<213> ORGANISM: pestivirus type 1
<220> FEATURE:
<221> NAME/KEY: misc_feature
<223> OTHER INFORMATION: BVDV-non-CP7 + cloning site; BVDV-non-CP7 with
      SnaBI, PacI restriction endonuclease insert

<400> SEQUENCE: 4

gtatacgagg ttaggcaagt tctcgtatac atattggaca ctctaaaaat aattaggcct     60

aggggacaaa aatcctcctt agcgaaggcc gaaaagaggc taaccatgcc cttagtagga    120

ctagcaaaat aagggggggta gcaacagtgg cgagttcgtt ggatggctga agccctgagt    180

acagggtagt cgtcagtggt tcgacgcttt ggaggacaag cctcgagatg ccacgtggac    240

gagggcatgc ccacagcaca tcttaacctg gacaggggtc gttcaggtga aaacggttta    300

accaaccgct acgaatacag tctgatagga tgctgcagag gcccactgta ttgctactga    360

aaatctctgc tgtacatggc acatggagtt gatcacaaat gaacttttat acaaaacata    420

caaacaaaaa cccgctggag tggaggaacc agtatacgac caagctggta accctttgtt    480

tggagaaaga ggagtgattc atccgcagtc aacgctaaaa cttccacata aaagagggga    540

gcgtgaagtc cccaccaatc tggcttcttt accaaaaaga ggtgactgca ggtcgggtaa    600

cagcaagggg cctgtgagtg gaatctactt aaaaccaggg ccgttattct accaagatta    660

taaaggacct gtctatcata gagccccatt ggagtttttt gaggaggcgt ctatgtgtga    720

gacaactaaa agaataggga gagtaactgg tagtgacagc agattatacc acatttacgt    780

gtgtattgat gggtgcataa tagtcaagag tgctacaaaa gaccgccaga aagtactcaa    840

gtgggtccac aacaagctaa actgcccccct atgggtttca agctgctccg acacaaaaga    900

tgaaggggtg gtgaggaaga agcaacaaaa gccagatagg ttggaaaagg ggagaatgaa    960

gataacacct aaggagtcag agaaagacag taagaccaag ccgccagatg ctacgatagt   1020

ggtagatgga gtcaagtatc aggtaaagaa aaaaggaaaa gtcaagagca agaacaccca   1080

ggacggctta taccacaaca aaaataaacc tcaagagtcg cgcaagaaac tagagaaagc   1140

cctattggcc tgggcaataa tagccctggt tttctttcaa gtcacaatgg gagagaacat   1200

aacgcaatgg aacttacaag ataatggaac ggaaggcata caacgagcca tgtttcaaag   1260

aggagtgaat agaagtttac atgggatctg gccagagaaa atctgtacag gtgttccttc   1320

ccacctggcc actgacacag aattgaaggc aattcatggt atgatggatg caagtgagaa   1380

gacaaattat acgtgctgca gactccaacg ccatgaatgg aacaaacatg gttggtgcaa   1440

ctggtacaac attgaacctt ggatcctcct tatgaataaa actcaggcca accttactga   1500

gggtcagcca ctaagggagt gtgccgtcac atgccggtat gatcgagata gtgacctgaa   1560

tgtagtaaca caagccaggg atagccccac accattaaca ggttgcaaga aaggcaaaaa   1620

cttttccttt gcaggcatat tggtacaagg gccttgcaac tttgaaatag ccgtaagtga   1680

tgtgctgttc aaagagcatg attgcactag tgtgattcaa gacacagctc actacctcgt   1740
```

```
agacgggatg accaactccc tagagagtgc caggcaaggg accgcgaaac taacaacttg   1800
gctgggcagg cagcttggga tactaggaaa gaaactggaa aacaagagta agacatggtt   1860
tggggcatat gcagcctctc cctattgtga ggtagaacgg aagcttggtt acatctggta   1920
tacaaagaat tgcactccag cctgtttgcc taggaataca aagatcatcg gccccggtag   1980
gtttgacacc aatgccgagg atggtaaaat actgcatgag atggggggtc acttgtcgga   2040
ggtgctacta ctctcagtgg tagtgctgtc cgatttcgct ccagagacag ccagtgtgat   2100
atacttgatt cttcatttct ccatcccaca aggacacact gatatacaag attgtgacaa   2160
aaaccaacta aacctcaccg tagaactcac aacagcagaa gtaataccag gctcagtttg   2220
gaacttgggt aaatatgttt gtgtaagacc agattggtgg ccttatgaga cagccacagt   2280
cctggtgatt gaagaggtgg gtcaagtaat taaggttgtc ttaagggcgt taaaagatct   2340
gacgcgcatt tggaccgctg ctacaaccac tgcattcttg gtttgtctgg tgaaggtagt   2400
gagaggccaa gtgttacaag gtatactgtg gctgatgctc ataacagggg cgcaagggta   2460
cccagactgc aaacccggct tttcatacgc catagccaaa aatgatgaga ttggcccact   2520
tggagctaca ggcctcacca ctcagtggta cgaatactcg gatgggatgc ggctgcagga   2580
ctcagtagtt gaagtttggt gtaaaaatgg agagatcaaa tatctaatca gatgcgggag   2640
ggaagccagg tatctggctg ttctacacac gagagccttg ccgacatctg tagtatttga   2700
aaaaattttt gatgggaaag aacaagagga catagtagaa atggatgaca actttgaatt   2760
cggtctttgc ccgtgtgatg ctagaccctt gataagggga aaatttaata caacacttct   2820
aaatgggcca gccttccaga tggtttgccc tataggatgg acagggactg taagctgtac   2880
actggccaat aaggatacgt tagccacaat cgttgtgaga acgtataaga gggtcaggcc   2940
ttttccatat aggcaggact gtgtcaccca gaaaaccatc ggggaagacc tctacgactg   3000
tgccttagga gggaattgga cttgtgtgcc gggggatgca ctacgatatg tagctgggcc   3060
cgttgagtct tgtgagtggt gtggttacaa gtttttaaaa agtgagggtc tgccgcattt   3120
cccaatcggc aaatgcaggc tgaagaatga gagtggctat agacaagtgg atgagacttc   3180
ttgcaacaga aacggcgtgg ctatagtgcc atctggcacg gtcaaatgca agatagggga   3240
cacggtggtg caagtcattg caatggatga taaactaggg cctatgcctt gcaaaccaca   3300
tgaaatcata tccagtgagg ggccagtgga aaagacggca tgcaccttca actacacaag   3360
aacattaaaa aacaagtact ttgagcccag ggataactat tttcaacaat acatgttaaa   3420
gggggagtac caatattggt ttgacctaga gatcactgac caccaccgag attacttcgc   3480
tgagtccctg ttggtgatag tagttgcact cctgggtggc aggtacgtgc tttggctgct   3540
ggtcacatac atgatcttat cagaacagat ggcctcgggt gtccagtatg ggcaggtga    3600
aatagtgatg atgggcaact tgttaacaca tgacagtgtt gaagtggtga catatttctt   3660
actactatac ctactactaa gagaggaaaa caccaaaaaa tgggtcatac ttatatacca   3720
catcatagta atgcatcctc taaaatcggt gacggtgata ttgctaatgg ttggggggat   3780
ggcaaaggct gaaccaggtg cccaggggta cctagagcag gtagacctta gttttacgat   3840
gattacgatc atcgtaatag gtctggttat agctaggcgt gatcccactg tggtgccact   3900
agtcactata gtcgcggcac tgaagatcac aggactaggc tttgggcccg gagtggatgc   3960
agctatggca gttctcacct taaccctact gatgactagt tatgtgacag actacttcag   4020
gtataaaagg tggatacaat gtatcctcag cttagtagcc ggggtgttcc ttatccggac   4080
```

-continued

```
cctcaaacat ctaggtgaac tcaaaacccc tgagctgacc ataccaaatt ggaggccact   4140

aaccttcata ctattatacc tgacttcagc aacagttgtt acaagatgga aaattgatat   4200

agctggcata ttcctgcaag gggcccctat ccttttgatg atcgccaccc tatgggctga   4260

cttcttgact cttgttctga tcctacccac ctacgaatta gccaagctgt actacctaaa   4320

gaacgtcaag actgacgtgg agaagagttg gctgggggg ttagactaca ggacaattga   4380

ctctgtctat gatgtggatg aaagtggaga aggcgtgtac ctcttcccgt ccagacagaa   4440

gaaaaataag aatatcagca tactcttgcc cctcatcaga gctacgctaa taagttgtat   4500

tagcagcaaa tggcagatgg tgtatatggc ttacttaacc ctggacttta tgtactacat   4560

gcacagaaag gttattgaag agatatcagg gagtaccaat gtgatgtcta gagtgatagc   4620

agcacttata gaattaaact ggtccatgga agaagaagag agcaagggct taaagaagtt   4680

ttttatacta tctggaaggt tgaggaacct tataataaag cataaggtta ggaaccagac   4740

tgtggcaagc tggtatgggg aggaagaagt ctacggcatg ccaaaagtcg taaccataat   4800

aagggcctgc acgctaaaca agaacaaaca ttgcataata tgcacagtat gtgaggctag   4860

aaagtggaag ggaggcaact gccctaaatg cggccgccac gggaagccca tcatttgtgg   4920

gatgactcta gcggattttg aagaaaggca ctacaagaga atttttataa gggaaggtaa   4980

ctttgaagga cccttcaggc aggaatacaa tgggtttgta caatacaccg ctagggggca   5040

attgttcctg agaaatttac ccatattggc aaccaaagta aaaatgatca tggtaggcaa   5100

cctaggagag gaaatcggtg atctagaaca cctaggatgg atcctaaggg gacctgccgt   5160

gtgcaagaaa ataactgagc acgaaaaatg ccatgtcaac atactggaca agctgactgc   5220

gtttttgga gttatgccaa gagggactac accaagggct ccggtgagat tcccaacagc   5280

actactaaag gtaaggaggg gattggaaac cggttgggct tacacgcatc aaggtggcat   5340

aagctcagta gaccatgtga ccgctggcaa ggatctattg gtttgtgaca gtatgggtag   5400

aactagagtg gtttgccaaa gcaacaacaa gttaactgat gagacagaat atggtgtcaa   5460

gacggactcc ggatgtccag atggtgccag atgctatgta ttaaacccag aggcagtaaa   5520

tatatcaggg tccaagggag ctgtcgtaca cctccaaaaa acgggtgggg aatttacatg   5580

tgttactgca tcaggtacac cggccttctt cgacctgaaa aatttgaaag gatggtcggg   5640

tctacccata tttgaagcct ccagcggcag agtggttggc agagtcaaag tgggaaagaa   5700

tgaggaatcc aaacccacaa aattaatgag tggtatccaa actgtttcta aaaatacggc   5760

cgatttaaca gaaatggtca agaagataac cagcatgaac agggggact ttaggcagat   5820

aacccttgca acaggggcag ggaagaccac tgagctccca aaagcagtga tagaggagat   5880

aggacgacac aaacgggtac tagtgctcat accattaaga gcagcagctg agtcagtcta   5940

tcaatacatg agattgaaac acccaagtat ctcctttaac ctgagaatag gggacatgaa   6000

agaaggggat atggcaaccg ggatcaccta cgcctcatat ggatattttt gccaaatgcc   6060

acaaccaaag ctcagagcag caatgataga gtattcatac atatttctgg atgagtatca   6120

ctgcgctact cctgagcagt tggctgttat aggaaaaatt cacagatttt ctgagagcat   6180

aagagtggtt gccatgactg ccaccccagc agggtcagta accacaacag ggcaaaaaca   6240

cccaatagaa gaattcatag cccctgaggt gatgaaaggg gaggaccttg gaagccagtt   6300

ccttgacata gcggggttaa agatccctgt agaggagatg aagggtaaca tgttggtttt   6360

cgtgcccacg aggaacatgg cagttgaagt agccaagaaa ctaaaagcca agggctacaa   6420

ctcagggtat tactacagtg ggaagaccc agctaacttg agagtggtaa catcacagtc   6480
```

-continued

```
cccatacgtc gtggtagcca ctaatgccat cgagtcaggg gtaacgctgc cagatttaga   6540
tacagttgtt gacacaggtc tgaaatgtga gaagagggtg agggtgtctt ccaaaatacc   6600
ctttatagta acaggcctta agagaatggc tgtcactgtg ggcgaacagg ctcagcggag   6660
aggcagggta ggtagagtga aacccggtag gtattataga agtcaggaaa cagcaaccgg   6720
gtcaaaggac taccactatg acttgttaca ggcacagagg tacgggatcg aagatgggat   6780
caacgtaaca aagtccttta gggagatgaa ttatgactgg agcctgtatg aggaagacag   6840
cttgctgata acccagctgg agatactgaa caatctactc atctctgaag atttaccagc   6900
agctgttaaa aacatcatgg caagaactga tcacccagag cctatccagc ttgcatataa   6960
cagttatgag gtccaagtcc ctgtgctgtt cccaaaaata aggaatgggg aggtcacaga   7020
cacttacgag aactactcat tcctaaatgc aaggaaacta ggggaagacg tgcccgtgta   7080
cgtttatgcc accgaagatg aagatctggc tgtggacctt ctaggcttgg actggccaga   7140
cccagggaat cagcaagtag tggagactgg gaaggcactg aagcaagtgg taggactgtc   7200
ctctgccgaa aatgccttgc tcatagccct atttgggtat gtaggatacc aagccttgtc   7260
aaaaagacac gtcccaatga tcacagacat atacactata gaagatcaaa gactagagga   7320
cacaacccac cttcaatatg cgcccaatgc cataagaact gaggggaagg agactgaact   7380
aaaggaatta gcagtgggtg acttggacaa aatcatgggt tccatctcgg actatgcatc   7440
agagggattg aatttcgtaa ggtcccaagc agaaaagatg agatctgccc ccgctttcaa   7500
agaaaacgtg gaagctgcta aagggtacgt ccaaaagttt attgattctc tcatagaaaa   7560
taaagaaacc ataatcagat atggcctgtg ggaacacac acggcactct acaagagtat    7620
tgccgcgaga ttgggtcatg aaactgcatt cgctacacta gtgataaagt ggctggcctt   7680
cgggggtgag tcggtgtcag accacatgag acaagcagct gtcgacctgg ttgtttatta   7740
tgtgatcaat aagccctcct tcccagggga ttctgaaacc caacaggaag gaaggcgatt   7800
cgtcgccagc ctgttcatct ccgctttggc aacctacaca tacaaaactt ggaattacaa   7860
caacctctcc aaggtagtag aaccagcctt agcatacctc ccctatgcta ccaatgcact   7920
aaaaatgttt accccgacca gactggagag cgtagttata cttagtacca caatatacaa   7980
aacttacctc tcaataagga agggaaagag tgatggactg ttgggtacag ggatcagtgc   8040
agcaatggag attctatcac agaacccagt gtcggtaggt atatctgtca tgctgggggt   8100
gggggcgatt gccgcgcaca atgccattga gtctagtgaa caaaaaagga ccctgttgat   8160
gaaagtgttt gtaaaaaact tcctggacca ggcggcaaca gatgagctgg taaaggaaaa   8220
cccagagaaa ataataatgg ccctatttga agcagtccag acaattggca accccttgag   8280
gctcatatat cacctgtatg ggtttacta caaaggctgg gaagcaaaag aactatcaga    8340
gagaacagca ggcaggaacc tgttcacctt gataatgttc gaagccttcg aactactagg   8400
gatggactct gaagggaaga taaggaacct gtctgggaat tatgtcctgg atttgatcta   8460
cagcctacat aaacagataa atagaggctt gaaaaaaata gtcttggggt gggctcccgc   8520
accatttagt tgcgactgga ctcctagtga tgagagaatt aggttaccca caaacaacta   8580
tctaagagta gaaactaagt gtccatgtgg ctatgagatg aaagcactaa ggaacgttgg   8640
tggcagtctt accaaagtgg aggagaaagg accttttctc tgcaggaaca ggcttggtag   8700
agggccggtc aactatagag tcacaaagta ctatgatgac aacctcaaag agataaaacc   8760
agttgctaaa ctagaaggat ttgtggatca ctattacaaa ggtgttacag caaggataga   8820
```

-continued

```
ttatggcaga gggaaaatgc tattagctac tgataaatgg gaggtggagc acggtgttgt   8880
cactaggttg gcaaagagat ataccggagt tggattcaag ggagcatacc tgggtgatga   8940
acccaaccac cgcgacctag tagaaagaga ctgtgcaact ataacaaaaa atacagtgca   9000
gtttttaaaa atgaagaaag gctgtgcatt tacctatgac ttaaccctgt ccaatttaac   9060
caggttaatt gaattggtac acaaaaataa cctagaagag aaagacatac cagcagccac   9120
agtaacgaca tggctggctt atacttttgt aaatgaagat attgggacta taaaaccagt   9180
actaggagag agagtggtca ccgacccagt ggtggatgtt aacttacaac cagaagtaca   9240
agtggataca tcagaggttg ggatcacttt agttggtagg gcagccttaa tgacgacagg   9300
tactacaccc gtagtcgaaa aaacagagcc caatgctgat ggtggtccaa gctccataaa   9360
gattgggttg gatgaaggaa gatacccagg acctggactg caagaccgca ccttgaccga   9420
tgaaatacat tctagggatg aaaggccctt tgttctagtc ctgggctcaa aaaattctat   9480
gtcaaataga gctaaaactg ctagaaacat caacttatac aaggggaata accccaggga   9540
gattagagat ctgatggcac aggggcgtat gctagttgtg gccttaaagg attttaaccc   9600
tgagttgtct gaactagttg atttcaaggg gactttctta gacagggaag ccttggaagc   9660
tctcagcctg gggcggccaa agtccaagca ggtgaccaca gccacagtta gggagttatt   9720
agagcaggag gtacaagttg agatccccag ttggtttgga gcaggtgatc cagtcttctt   9780
ggaagtgact ttgaagggtg acagatatca cttagtagga gatgtagata gagtgaaaga   9840
tcaagcgaag gagcttgggg ccacggacca gacaagaata gtgaaggaag tgggtgcaag   9900
aacctatacc atgaagctgt ctagttggtt tcttcaggca acaaataaac agatgagctt   9960
gaccccttta tttgaggagc tattgctacg ttgcccccct aaaataaaga gcaataaagg  10020
gcacatggca tcagcttacc aactagcaca gggaaactgg gagccccttg actgtggagt  10080
tcacctgggc accatacctg ccaggagggt aaaaatccac ccatatgaag cttacctgaa  10140
actgaaggat ttattggaag aagaagaaaa gaaaccaaag tgtagagaca cagtaataag  10200
agaacacaac aagtggatcc tcaaaaaagt gaggcaccag ggtaatctca atacaaagaa  10260
aatcctcaac cctggaaagc tatcagaaca gctagataga gaagggcata aaagaaacat  10320
ttataacaat cagattggca ccataatgac ggaagcagga agtaggttgg aaaaattacc  10380
agtcgtcaga gcccaaactg acactaaaag cttccatgag gcaatcagag ataagataga  10440
caagaatgaa aatcagcaga gcccaggact gcatgataaa ttgttagaga tctttcatac  10500
aatagcccaa cccagcctaa gacacaccta cagtgacgtg acgtgggagc aacttgaggc  10560
aggggttaat agaaaggggg ctgctggctt tctagagaag aagaatgttg gagaagtact  10620
ggactcagag aagcacctgg tggaacaact gatcagagat ttgaaaacag gaaggaagat  10680
aagatattat gagacagcaa taccaaaaaa tgagaagaga gatgtcagtg atgattggca  10740
atcaggggac ttagtagatg agaagaaacc aagggtgatt caataccctg aagctaaaac  10800
aagactagcc atcactaaag taatgtacaa ctgggtgaaa cagcagcccg tcgtgatccc  10860
agggtatgaa gggaagaccc cattatttaa cattttcaac aaggtgagga aggaatggga  10920
tttgttcaat gaaccagtag ctgtgagttt cgacactaag gcttgggaca cccaagtaac  10980
tagtagagat ctacggctta ttggtgaaat tcaaaaatat tactacagga aagagtggca  11040
caaattcatc gataccatta ctgaccatat ggtggaggtg cccgtcataa cggcagatgg  11100
tgaggtatac ataagaaatg gacaaagggg tagtggccag ccagacacaa gtgcaggcaa  11160
tagcatgcta aacgtgttaa caatgatgta tgccttctgt gaaagtacgg gggttccata  11220
```

```
caagagtttc aatagggttg caaggatcca tgtctgtggg gatgacggct tcctaataac  11280

agagaagggg ctgggattaa agtttgccaa caatgggatg caaattctgc acgaagcagg  11340

caagcctcaa aagataactg agggggaaag aatgaaagtt gcctataggt tcgaggacat  11400

agaattctgc tctcatacac cagtccccgt taggtggtct gataacacca gcagttacat  11460

ggccggcaga gacactgccg ttatattatc aaagatggca acaagattgg attcaagtgg  11520

agaaaggggt actatagcat atgaaaaagc agtggccttt agtttttttgc tgatgtactc  11580

ctggaatcct cttgtgagga ggatctgtct actggtcctt tcacagcagc cagagacaac  11640

tccatcaacc cagaccactt actattataa aggagaccca ataggagcct acaaagatgt  11700

aataggtaag aatttgtgtg aattaaaaag gacgggtttt gaaaaattgg ccaatttaaa  11760

cctaagcctg tccacgttag gaatctggtc caaacataca agtaaaagaa tcatccaaga  11820

ctgtgtaacc atcgggaaag aggaaggcaa ttggctggtc aatgccgaca ggttgatatc  11880

tagcaaaact ggccatttgt acatacctga caaaggttat acattacaag ggaaacatta  11940

tgaacaactt caactgcagg caagaactag cccagtcacg ggagtaggga cggagagata  12000

taaactaggc cctatagtaa acctgctgct gaggaggttg agagttctgc ttatggcagc  12060

tgtcggtgcc agcagttgaa ataatgtatg tatatattgt atataaatct gtatttgtat  12120

atattatgtt taaatacgta ttaattaatt tagttgagat tagtagtgat atatagttat  12180

ctacctcaag ctaacactac actcaatgca cacagcactt tagctgtatg agggtacacc  12240

cgacgtccac ggttggacta gggaaaaccc ttaacagccc c                     12281
```

<210> SEQ ID NO 5
<211> LENGTH: 355
<212> TYPE: DNA
<213> ORGANISM: pestivirus type 1
<220> FEATURE:
<221> NAME/KEY: misc_feature
<223> OTHER INFORMATION: BVDV-non-CP7 3' NTR

<400> SEQUENCE: 5

```
tacgtagcca gcccccgatt gggggcgaca ctccaccata gatcactccc ctgtgaggaa     60

ctactgtctt cacgcagaaa gcgtctagcc atggcgttag tatgagtgtc gtgcagcctc    120

caggaccccc cctctcggga gagccatagt ggtctgcgga accggtgagt acaccggaat    180

tgccaggacg accgggtcct ttcttggatc aacccgctca atgcctggag atttgggcgt    240

gcccccgcga gactgctagc cgagtagtgt tgggtcgcga aaggccttgt ggtactgcct    300

gatagggtgc ttgcgagtgc ctcgggaggt ctcgtagacc gtgcacctta attaa         355
```

<210> SEQ ID NO 6
<211> LENGTH: 205
<212> TYPE: DNA
<213> ORGANISM: pestivirus type 1
<220> FEATURE:
<221> NAME/KEY: misc_feature
<223> OTHER INFORMATION: BVDV-non-CP7 + cloning site chimera, 3'NTR, SnaBI and PacI restriction endonuclease insert

<400> SEQUENCE: 6

```
tgaaataatg tatgtatata ttgtatataa atctgtattt gtatatatta tgtttaaata     60

cgtattaatt aatttagttg agattagtag tgatatatag ttatctacct caagctaaca    120

ctacactcaa tgcacacagc actttagctg tatgagggta cacccgacgt ccacggttgg    180

actagggaaa acccttaaca gcccc                                           205
```

<210> SEQ ID NO 7
<211> LENGTH: 549
<212> TYPE: DNA
<213> ORGANISM: pestivirus type 1
<220> FEATURE:
<221> NAME/KEY: misc_feature
<223> OTHER INFORMATION: BVDV-non-CP7- HCV 5' NTR chimera, 3'NTR

<400> SEQUENCE: 7
tgaaataatg tatgtatata ttgtatataa atctgtattt gtatatatta tgtttaaata 60
cgtagccagc ccccgattgg gggcgacact ccaccataga tcactcccct gtgaggaact 120
actgtcttca cgcagaaagc gtctagccat ggcgttagta tgagtgtcgt gcagcctcca 180
ggaccccccc tctcgggaga gccatagtgg tctgcggaac cggtgagtac accggaattg 240
ccaggacgac cgggtccttt cttggatcaa cccgctcaat gcctggagat ttgggcgtgc 300
ccccgcgaga ctgctagccg agtagtgttg ggtcgcgaaa ggccttgtgg tactgcctga 360
tagggtgctt gcgagtgcct cgggaggtct cgtagaccgt gcaccttaat taataattta 420
gttgagatta gtagtgatat atagttatct acctcaagct aacactacac tcaatgcaca 480
cagcacttta gctgtatgag ggtacacccg acgtccacgg ttggactagg gaaaaccctt 540
aacagcccc 549

<210> SEQ ID NO 8
<211> LENGTH: 524
<212> TYPE: DNA
<213> ORGANISM: pestivirus type 1
<220> FEATURE:
<221> NAME/KEY: misc_feature
<223> OTHER INFORMATION: BVDV-non-CP7 - HCV 5' NTR chimera, BamHI / XbaI cloned PCR fragment, clone 1

<400> SEQUENCE: 8
ggatccgctg tcggtgccag cagttgaaat aatgtatgta tatattgtat ataaatctgt 60
atttgtatat attatgttta aatacgtagc cagcccccta ttgggggcga cactccacca 120
tagatcactc ccctgtgagg aactactgtc ttcacgcaga aagcgtctag ccatggcgtt 180
agtatgagtg tcgtgcagcc tccaggaccc cccctctcgg gagagccata gtggtctgcg 240
gaaccggtga gtacaccgga attgccagga cgaccgggtc ctttcttgga tcaacccgct 300
caatgcctgg agatttgggc gtgcccccgc gagactgcta gccgagtagt gttgggtcgc 360
gaaaggcctt gtggtactgc ctgatagggt gcttgcgagt gcctcgggag gtctcgtaga 420
ccgtgcacct taattaataa tttagttgag attagtagtg atatatagtt atctacctca 480
agctaacact acactcaatg cacacagcac tttagctgtc taga 524

<210> SEQ ID NO 9
<211> LENGTH: 524
<212> TYPE: DNA
<213> ORGANISM: pestivirus type 1
<220> FEATURE:
<221> NAME/KEY: misc_feature
<223> OTHER INFORMATION: BVDV non-CP7 - HCV 5'NTR chimera, BamHI / XbaI cloned PCR fragment, clone 2

<400> SEQUENCE: 9
ggatccgctg tcggtgccag cagttgaaat aatgtatgta tatattgtat ataaatctgt 60
atttgtatat attatgttta aatacgtagc cagcccccga ttgggggcga cactccacca 120
tagatcactc ccctgtgagg aactactgtc ttcacgcaga aagcgtctag ccatggcgtt 180

-continued

```
agtatgagtg tcgtgcagcc tccaggaccc cccctctcgg gagagccata gtggtctgcg    240

gaaccggtga gtacaccgga attgccagga cgaccgggtc ctttcttgga tcaacccgct    300

caatgcctgg agatttgggc gtgcccccgc gagactgcta gccgagtagt gttgggtcgc    360

gaaaggcctt gtggtactgt ctgatagggt gcttgcgagt gcctcgggag gtctcgtaga    420

ccgtgcacct taattaataa tttagttgag attagtagtg atatatagtt atctacctca    480

agctaacact acactcaatg cacacagcac tttagctgtc taga                     524


<210> SEQ ID NO 10
<211> LENGTH: 524
<212> TYPE: DNA
<213> ORGANISM: pestivirus type 1
<220> FEATURE:
<221> NAME/KEY: misc_feature
<223> OTHER INFORMATION: BVDV-non-CP7- HCV 5' NTR chimera, BamHI / Xba
      I cloned PCR fragment, clone 3

<400> SEQUENCE: 10

ggatccgctg tcggtgccag cagttgaaat aatgtatgta tatattgtat ataaatctgt     60

atttgtatat attatgttta aatacgtagc cagcccccga ttgggggcga cactccacca    120

tagatcactc ccctgtgagg aactactgtc ttcacgcaga aagcgtctag ccatggcgtt    180

agtatgagtg tcgtgcagcc tccaggaccc cccctctcgg gagagccata gtggtctgcg    240

gaaccggtga gtacaccgga attgccagga cgaccgggtc ctttcttgga tcaacccgct    300

caatgcctgg agatttgggc gtgcccccgc gagactgcta gccgagtagt gttgggtcgc    360

gaaaggcctt gtggtactgc ctgatagggt gcttgcgagt gcctcgggag gtctcgtaga    420

ccgtgcacct taattaataa tttagttgag attagtagtg atatatagtt atctacctca    480

agccaacact acactcaatg cacacagcac tttagctgtc taga                     524


<210> SEQ ID NO 11
<211> LENGTH: 524
<212> TYPE: DNA
<213> ORGANISM: pestivirus type 1
<220> FEATURE:
<221> NAME/KEY: misc_feature
<223> OTHER INFORMATION: BVDV-non-CP7 - HCV 5'NTR chimera, BamHI / XbaI
      cloned PCR fragment, clone 4

<400> SEQUENCE: 11

ggatccgctg tcggtgccag cagttgaaat aatgtatgta tatattgtat ataaatctgt     60

atttgtatat attatgttta aatacgtagc cagcccccga ttgggggcga cactccacca    120

tagatcactc ccctgtgagg aactactgtc ttcacgcaga aagcgtctag ccatggcgtt    180

agtatgagtg tcgtgcagcc tccaggaccc cccctctcgg gagagccata gtggtctgcg    240

gaaccggtga gtacaccgga attgccagga cgaccgggtc ctttcttgga tcaacccgct    300

caatgcctgg agatttgggc gtgcccccgc gagactgcta gccgagtagt gttgggtcgc    360

gaaaggcctt gtggtactgc ctgatagggt gcttgcgagt gcctcgggag gtctcgtaga    420

ccgtgcacct taattaataa tttagttgag attagtagtg atatatagtt atctacctca    480

agctaacact acactcaatg cacacagcac tttagctgtc taga                     524


<210> SEQ ID NO 12
<211> LENGTH: 523
<212> TYPE: DNA
<213> ORGANISM: pestivirus type 1
<220> FEATURE:
```

<221> NAME/KEY: misc_feature
<223> OTHER INFORMATION: BVDV-non-CP7 - HCV 5'NTR chimera, BamHI / XbaI
      cloned PCR fragment, clone 5

<400> SEQUENCE: 12

```
ggatccgctg tcgtgccagc agttgaaata atgtatgtat atattgtata taaatctgta     60
tttgtatata ttatgtttaa atacgtagcc agcccccgat tgggggcgac actccaccat    120
agatcactcc cctgtgagga actactgtct tcacgcagaa agcgtctagc catggcgtta    180
gtatgagtgt cgtgcagcct ccaggacccc ccctctcggg agagccatag tggtctgcgg    240
aaccggtgag tacaccggaa ttgccaggac gaccgggtcc tttcttggat caacccgctc    300
aatgcctgga gatttgggcg tgcccccgcg agactgctag ccgagtagtg ttgggtcgcg    360
aaaggccttg tggtactgcc tgatagggtg cttgcgagtg cctcgggagg tctcgtagac    420
cgtgcacctt aattaataat ttagttgaga ttagtagtga tatatagtta tctacctcaa    480
gctaacacta cactcaatgc acacagcact ttagctgtct aga                      523
```

<210> SEQ ID NO 13
<211> LENGTH: 351
<212> TYPE: DNA
<213> ORGANISM: Hepatitis C virus
<220> FEATURE:
<221> NAME/KEY: misc_feature
<223> OTHER INFORMATION: HCV subtype 1a, 5'NTR

<400> SEQUENCE: 13

```
gctaataata acagccccct gatgggggcg acactccacc atgaatcact cccctgtgag     60
gaactactgt cttcacgcag aaagcgtcta gccatggcgt tagtatgagt gtcgtacagc    120
ctccaggacc ccccctctcg ggagagccat agtggtctgc ggaaccggtg agtacaccgg    180
aattgccagg acgaccgggt cctttcttgg ataaaacccg ctcaatgcct ggagatttgg    240
gcgtgccccc gcaagactgc tggccgagta gtgttgggtc gcgaaaggcc ttgtggtact    300
gcctgatagg gtgcttgcga gtgcctcggg aggtctcgta gaccgtgcac c             351
```

<210> SEQ ID NO 14
<211> LENGTH: 349
<212> TYPE: DNA
<213> ORGANISM: Hepatitis C virus
<220> FEATURE:
<221> NAME/KEY: misc_feature
<223> OTHER INFORMATION: HCV subtype 2a, 5'NTR

<400> SEQUENCE: 14

```
actaataata accgccccta ataggggcga cactccgcca tgaatcactc ccctgtgagg     60
aactactgtc ttcacgcaga aagcgtctag ccatggcgtt agtatgagtg tcgtacagcc    120
tccaggcccc cccctctcgg gagagccata gtggtctgcg gaaccggtga gtacaccgga    180
attgccggga agaccgggtc ctttcttgga taaacccgct ctatgcccgg ccatttgggc    240
gtgcccccgc aagactgcta gccgagtagc gttgggttgc gaaaggcctt gtggtactgc    300
ctgatagggt gcttgcgagt gcctcgggag gtctcgtaga ccgtgcacc                349
```

<210> SEQ ID NO 15
<211> LENGTH: 348
<212> TYPE: DNA
<213> ORGANISM: Hepatitis C virus
<220> FEATURE:
<221> NAME/KEY: misc_feature
<223> OTHER INFORMATION: HCV subtype 3a, 5'NTR

<400> SEQUENCE: 15
actaataata actgcctctt acgaggcgac actccaccat ggatcactcc cctgtgagga 60
acttctgtct tcacgcggaa agcgcctagc catggcgtta gtacgagtgt cgtgcagcct 120
ccaggccccc ccctctcggg agagccatag tggtctgcgg aaccggtgag tacaccggaa 180
tcgctggggt gaccgggtcc tttcttggaa caacccgctc aatacccaga aatttgggcg 240
tgcccccgcg agatcactag ccgagtagtg ttgggtcgcg aaaggccttg tggtactgcc 300
tgatagggtg cttgcgagtg cctcgggagg tctcgtagac cgtgcaac 348

<210> SEQ ID NO 16
<211> LENGTH: 342
<212> TYPE: DNA
<213> ORGANISM: Hepatitis C virus
<220> FEATURE:
<221> NAME/KEY: misc_feature
<223> OTHER INFORMATION: HCV subtype 4a, 5'NTR

<400> SEQUENCE: 16
tttaataata agggggcgac actccaccat agatcactcc cctgtgaggt actactgtct 60
tcacgcagaa agcgtctagc catggcagtt agtatagagt gtcgtacagc ctccaggacc 120
ccccctctcg ggagagccat agtggtctgc ggaaccggtg agtacaccgg aatcgccagg 180
acgaccgggt cctttcttgg ataaacccgc tccatgcctg gaaatttggg cgtgcccccg 240
caagactgct aagcgagtag tgttgggtcg cgaaaggcct tgtggtactg cctgataagg 300
tgcttgcgag tcgccgggga ggtactcgta gacctgtgca cc 342

<210> SEQ ID NO 17
<211> LENGTH: 318
<212> TYPE: DNA
<213> ORGANISM: Hepatitis C virus
<220> FEATURE:
<221> NAME/KEY: misc_feature
<223> OTHER INFORMATION: HCV subtype 5a, 5'NTR

<400> SEQUENCE: 17
attaataata agatcactcc cctgtgagga actactgtct tcacgcagaa agcgtctagc 60
catggcgtta gtatgagtgt cgaacagcct ccaggacccc ccctctcggg agagccatag 120
tggtctgcgg aaccggtgag tacaccggaa ttgccgggat gaccgggtcc tttcttggat 180
aaacccgctc aatgcccgga gatttgggcg tgcccccgcg agactgctag ccgagtagtg 240
ttgggtcgcg aaaggccttg tggtactgcc tgatagggtg cttgcgagtg cctcgggagg 300
tctcgtagac cgtgcacc 318

<210> SEQ ID NO 18
<211> LENGTH: 348
<212> TYPE: DNA
<213> ORGANISM: Hepatitis C virus
<220> FEATURE:
<221> NAME/KEY: misc_feature
<223> OTHER INFORMATION: HCV subtype 6p, 5'NTR

<400> SEQUENCE: 18
gctaataata acagccccta atggggcgac actccaccat gatcactccc ctgtgaggaa 60
ctactgtctt cacgcagaaa gcgtctagcc atggcgttag tatgagtgtc gtgcagcctc 120
caggatcccc cctctcggga gagccatagt ggtctgcgga accggtgagt tcaccggaat 180
tgccaggacg accgggtcct ttcttggatc aaacccgctc aatgcctgga gatttgggcg 240
tgcccccgcg agactgctag ccgagtagtg ttgggtcgcg aaaggccttg tggtactgcc 300
tgatagggtg cttgcgagtg cctcgggagg tctcgtagac cgtgcatc 348

<210> SEQ ID NO 19
<211> LENGTH: 317
<212> TYPE: DNA
<213> ORGANISM: Hepatitis C virus
<220> FEATURE:
<221> NAME/KEY: misc_feature
<223> OTHER INFORMATION: HCV subtype 7a, 5'NTR

<400> SEQUENCE: 19
gataataata aatcactccc ctgcgaggaa ccactgtcct cacgcagaaa gcgtctagcc 60
atgacgttag tatgagtgtc gtacagcctc caggaccccc cctctcggga gagccatagt 120
ggtctgcgga accggtgagt acaccggaat tgccgggaag actgggtcct ttcttggatc 180
aacccactct atgcccggag atttgggcgt gcccccgcga gactgctagc cgagtagtgt 240
tgggtcgcga aaggccttgt ggtactgcct gatagggtgc ttgcgagtgc ctcgggaggt 300
ctcgtagacc gtgcacc 317

<210> SEQ ID NO 20
<211> LENGTH: 1325
<212> TYPE: DNA
<213> ORGANISM: Artificial Sequence
<220> FEATURE:
<223> OTHER INFORMATION: IRES-EGFP: Encephalomyocarditis virus IRES
and ORF for GFP

<400> SEQUENCE: 20
ccgcgggctc gggatccgcc cctctccctc ccccccccct aacgttactg gccgaagccg 60
cttggaataa ggccggtgtg cgtttgtcta tatgttattt tccaccatat tgccgtcttt 120
tggcaatgtg agggcccgga aacctggccc tgtcttcttg acgagcattc ctaggggtct 180
ttcccctctc gccaaaggaa tgcaaggtct gttgaatgtc gtgaaggaag cagttcctct 240
ggaagcttct tgaagacaaa caacgtctgt agcgaccctt tgcaggcagc ggaacccccc 300
acctggcgac aggtgcctct gcggccaaaa gccacgtgta taagatacac ctgcaaaggc 360
ggcacaaccc cagtgccacg ttgtgagttg gatagttgtg gaaagagtca aatggctctc 420
ctcaagcgta ttcaacaagg ggctgaagga tgcccagaag gtaccccatt gtatgggatc 480
tgatctgggg cctcggtgca catgctttac atgtgtttag tcgaggttaa aaaaacgtct 540
aggccccccg aaccacgggg acgtggtttt cctttgaaaa acacgatgat aatatggcca 600
caaccatggt gagcaagggc gaggagctgt tcaccggggt ggtgcccatc ctggtcgagc 660
tggacggcga cgtaaacggc cacaagttca gcgtgtccgg cgagggcgag ggcgatgcca 720
cctacggcaa gctgaccctg aagttcatct gcaccaccgg caagctgccc gtgccctggc 780
ccaccctcgt gaccaccctg acctacggcg tgcagtgctt cagccgctac cccgaccaca 840
tgaagcagca cgacttcttc aagtccgcca tgcccgaagg ctacgtccag gagcgcacca 900
tcttcttcaa ggacgacggc aactacaaga cccgcgccga ggtgaagttc gagggcgaca 960
ccctggtgaa ccgcatcgag ctgaagggca tcgacttcaa ggaggacggc aacatcctgg 1020
ggcacaagct ggagtacaac tacaacagcc acaacgtcta tatcatggcc gacaagcaga 1080
agaacggcat caaggtgaac ttcaagatcc gccacaacat cgaggacggc agcgtgcagc 1140
tcgccgacca ctaccagcag aacaccccca tcggcgacgg ccccgtgctg ctgcccgaca 1200
accactacct gagcacccag tccgccctga gcaaagaccc caacgagaag cgcgatcaca 1260

-continued

```
tggtcctgct ggagttcgtg accgccgccg ggatcactct cggcatggac gagctgtaca    1320

agtaa                                                                1325
```